(12) United States Patent
Cooper et al.

(10) Patent No.: US 11,905,252 B2
(45) Date of Patent: Feb. 20, 2024

(54) COMPOUNDS

(71) Applicant: INFLAZOME LIMITED, Dublin (IE)

(72) Inventors: Matthew Cooper, Cambridge (GB); David Miller, Cambridge (GB); Angus Macleod, Cambridge (GB); Jonathan Shannon, Nottingham (GB)

(73) Assignee: INFLAZOME LIMITED, Dublin (IE)

( * ) Notice: Subject to any disclaimer, the term of this patent is extended or adjusted under 35 U.S.C. 154(b) by 0 days.

(21) Appl. No.: 16/977,241

(22) PCT Filed: Mar. 1, 2019

(86) PCT No.: PCT/EP2019/055127
§ 371 (c)(1),
(2) Date: Sep. 1, 2020

(87) PCT Pub. No.: WO2019/166619
PCT Pub. Date: Sep. 6, 2019

(65) Prior Publication Data
US 2021/0347737 A1    Nov. 11, 2021

(30) Foreign Application Priority Data

Mar. 2, 2018  (GB) ...................................... 1803392
Aug. 15, 2018 (GB) ...................................... 1813284

(51) Int. Cl.
| C07D 231/18 | (2006.01) |
| C07D 401/12 | (2006.01) |
| C07D 213/04 | (2006.01) |
| C07D 333/04 | (2006.01) |
| C07D 307/34 | (2006.01) |

(52) U.S. Cl.
CPC ................................. C07D 231/18 (2013.01)

(58) Field of Classification Search
None
See application file for complete search history.

(56) References Cited

U.S. PATENT DOCUMENTS

| 4,723,991 | A  | 2/1988  | Holyoke, Jr. et al. |
| 4,741,760 | A  | 5/1988  | Meyer et al. |
| 4,795,486 | A  | 1/1989  | Bohner et al. |
| 4,802,908 | A  | 2/1989  | Hillemann |
| 5,169,860 | A  | 12/1992 | Mohamad et al. |
| 5,219,856 | A  | 6/1993  | Olson |
| 5,486,618 | A  | 1/1996  | Hagen et al. |
| 10,538,487 | B2 | 1/2020  | O'Neill et al. |
| 11,130,731 | B2 | 9/2021  | O'Neill et al. |
| 11,370,776 | B2 | 6/2022  | Cooper et al. |
| 2002/0034764 | A1 | 3/2002  | Gabel et al. |
| 2002/0077486 | A1 | 6/2002  | Scarborough et al. |
| 2006/0069093 | A1 | 3/2006  | Scarborough et al. |
| 2019/0119224 | A1 | 4/2019  | Glick et al. |
| 2019/0192478 | A1 | 6/2019  | Hacini-Rachinel |
| 2019/0337965 | A1 | 11/2019 | Stafford et al. |
| 2020/0207780 | A1 | 7/2020  | O'Neill et al. |
| 2020/0291003 | A1 | 9/2020  | Cooper et al. |
| 2020/0299284 | A1 | 9/2020  | O'Neill et al. |
| 2020/0317637 | A1 | 10/2020 | Cooper et al. |
| 2020/0354341 | A1 | 11/2020 | Cooper et al. |
| 2020/0361895 | A1 | 11/2020 | Cooper et al. |
| 2021/0122716 | A1 | 4/2021  | Cooper et al. |
| 2021/0122739 | A1 | 4/2021  | Cooper et al. |
| 2021/0130329 | A1 | 5/2021  | Cooper et al. |

(Continued)

FOREIGN PATENT DOCUMENTS

| CN | 104513239 A | 4/2015 |
| CN | 109432078 A | 3/2019 |
| CN | 110151749 A | 8/2019 |

(Continued)

OTHER PUBLICATIONS

Alsante, et al., "Pharmaceutical Impurity Identification: A Case Study Using a Multidisciplinary Approach," Journal of Pharmaceutical Sciences, 93(9): 2296-2309, (2004).
Baldwin, et al., "Inhibiting the inflammasome: a chemical perspective," Journal of Medicinal Chemistry, 59(5): 1691-1710, (2016).
Booth, et al., "A new and efficient approach to the synthesis of 6-amidino-2-oxopurines," Journal of the Chemical Society Perkin Transactions 1, 1(10): 1241-1251, (2001).
Braddock, et al., "Targeting IL-1 in Inflammatory Disease: New Opportunities for Therapeutic Intervention," Nature Reviews Drug Discovery, 3(4): 330-340, (2004).

(Continued)

*Primary Examiner* — Samantha L Shterengarts
(74) *Attorney, Agent, or Firm* — Alston & Bird LLP

(57) ABSTRACT

The present invention relates to sulfonylureas and sulfonylthioureas of formula (I) comprising a 5-membered heteroaryl ring attached to the sulfonyl group, wherein the heteroaryl ring is di-substituted at the 3- and 4-positions relative to the point of attachment of the sulfonyl group, and wherein the group attached to the terminal nitrogen atom of the urea group is either a 1,2,3,5,6,7-hexahydro-s-indacen-4-yl group substituted at the 8-position, or a heteroaryl group substituted at the alpha and alpha' positions. The present invention further relates to salts, solvates and prodrugs of such compounds, to pharmaceutical compositions comprising such compounds, and to the use of such compounds in the treatment and prevention of medical disorders and diseases, most especially by NLRP3 inhibition.

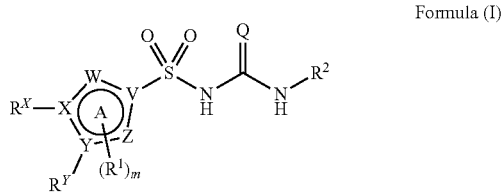

Formula (I)

22 Claims, No Drawings

(56) References Cited

U.S. PATENT DOCUMENTS

| | | | |
|---|---|---|---|
| 2021/0130359 A1 | 5/2021 | Cooper et al. | |
| 2021/0163412 A1 | 6/2021 | Shannon et al. | |

FOREIGN PATENT DOCUMENTS

| | | | |
|---|---|---|---|
| DK | 2006 00313 A | 3/2006 | |
| EP | 0125864 A1 | 11/1984 | |
| EP | 0176304 A1 | 4/1986 | |
| EP | 0177163 A2 | 4/1986 | |
| EP | 0189069 A2 | 7/1986 | |
| EP | 0204513 A2 | 12/1986 | |
| EP | 0224842 A2 | 6/1987 | |
| EP | 0249938 A2 | 12/1987 | |
| EP | 0318602 A1 | 6/1989 | |
| EP | 0610653 A1 | 8/1994 | |
| EP | 0795548 A1 | 9/1997 | |
| EP | 0885890 A1 | 12/1998 | |
| EP | 0976742 A1 | 2/2000 | |
| EP | 0987552 A2 | 3/2000 | |
| EP | 1236468 A1 | 9/2002 | |
| EP | 1270565 A1 | 1/2003 | |
| EP | 1670749 A1 | 2/2005 | |
| EP | 1995240 A1 | 11/2008 | |
| EP | 2543670 A1 | 1/2013 | |
| EP | 2781216 A1 | 9/2014 | |
| EP | 2962692 A1 | 1/2016 | |
| EP | 3272739 A1 | 1/2018 | |
| FR | 2068472 A1 | 8/1971 | |
| GB | 797474 A | 7/1958 | |
| GB | 1146979 A | 3/1969 | |
| GB | 1322980 A | 7/1973 | |
| GB | 1713082.4 | 8/2018 | |
| GB | 1718563.8 | 8/2018 | |
| JP | S6045573 A | 12/1985 | |
| JP | 62-148482 A | 7/1987 | |
| JP | 62-195376 A | 8/1987 | |
| JP | 06199053 A | 7/1994 | |
| JP | 06199054 A | 7/1994 | |
| JP | 2000053649 A | 2/2000 | |
| PL | 221813 B1 | 5/2016 | |
| RU | 2022963 C1 | 11/1994 | |
| WO | WO 91/10668 A1 | 7/1991 | |
| WO | WO 92/04319 A1 | 3/1992 | |
| WO | WO 93/04045 A1 | 3/1993 | |
| WO | WO 93/04046 A1 | 3/1993 | |
| WO | WO 97/11057 A1 | 3/1997 | |
| WO | WO 98/032733 A1 | 7/1998 | |
| WO | WO 00/55126 A2 | 9/2000 | |
| WO | WO 01/19390 A1 | 3/2001 | |
| WO | WO 01/57037 A1 | 8/2001 | |
| WO | WO 02/06246 A1 | 1/2002 | |
| WO | WO 02/094176 A2 | 11/2002 | |
| WO | WO 03/031194 A1 | 4/2003 | |
| WO | WO 03/045400 A1 | 6/2003 | |
| WO | WO 03/099805 A1 | 12/2003 | |
| WO | WO 2004/039376 A1 | 5/2004 | |
| WO | WO 2005/032488 A2 | 4/2005 | |
| WO | WO 2005/035520 A1 | 4/2005 | |
| WO | WO 2006/039212 A2 | 4/2006 | |
| WO | WO 2006-085815 A1 | 8/2006 | |
| WO | WO 2008/090382 A1 | 7/2008 | |
| WO | WO 2009/065096 A1 | 5/2009 | |
| WO | WO 2011/041694 A2 | 4/2011 | |
| WO | WO 2015/069666 A1 | 5/2015 | |
| WO | WO 2016/127924 A1 | 8/2016 | |
| WO | WO 2016/131098 A1 | 8/2016 | |
| WO | WO 2016/131098 A8 | 8/2016 | |
| WO | WO 2016/138473 A1 | 9/2016 | |
| WO | WO 2017/106957 A1 | 6/2017 | |
| WO | WO 2017/129897 A1 | 8/2017 | |
| WO | WO 2017/140778 A1 | 8/2017 | |
| WO | WO 2017/184604 A1 | 10/2017 | |
| WO | WO 2017/184624 A1 | 10/2017 | |
| WO | WO 2017/189652 A1 | 11/2017 | |
| WO | WO 2018/015445 A1 | 1/2018 | |
| WO | WO 2018/136890 A1 | 7/2018 | |
| WO | WO 2018/152396 A1 | 8/2018 | |
| WO | WO 2018/215818 A1 | 11/2018 | |
| WO | WO 2019/008025 A1 | 1/2019 | |
| WO | WO 2019/008029 A1 | 1/2019 | |
| WO | WO 2019/023147 A1 | 1/2019 | |
| WO | WO 2019/034686 A1 | 2/2019 | |
| WO | WO 2019/034688 A1 | 2/2019 | |
| WO | WO 2019/034690 A1 | 2/2019 | |
| WO | WO 2019/034692 A1 | 2/2019 | |
| WO | WO 2019/034693 A1 | 2/2019 | |
| WO | WO 2019/034696 A1 | 2/2019 | |
| WO | WO 2019/034697 A1 | 2/2019 | |
| WO | WO 2019/068772 A1 | 4/2019 | |
| WO | WO 2019/092170 A1 | 5/2019 | |
| WO | WO 2019/092171 A1 | 5/2019 | |
| WO | WO 2019/092172 A1 | 5/2019 | |
| WO | WO 2019/166619 A1 | 9/2019 | |
| WO | WO 2019/166621 A1 | 9/2019 | |
| WO | WO 2019/166623 A1 | 9/2019 | |
| WO | WO 2019/166624 A1 | 9/2019 | |
| WO | WO 2019/166627 A1 | 9/2019 | |
| WO | WO 2019/166628 A1 | 9/2019 | |
| WO | WO 2019/166629 A1 | 9/2019 | |
| WO | WO 2019/166632 A1 | 9/2019 | |
| WO | WO 2019/166633 A1 | 9/2019 | |
| WO | WO 2019/206871 A1 | 10/2019 | |
| WO | WO 2019/211463 A1 | 11/2019 | |
| WO | WO 2020/010118 A1 | 1/2020 | |
| WO | WO 2020/010143 A1 | 1/2020 | |
| WO | WO 2020/018970 A1 | 1/2020 | |
| WO | WO 2020/035464 A1 | 2/2020 | |
| WO | WO 2020/035465 A1 | 2/2020 | |
| WO | WO 2020/035466 A1 | 2/2020 | |
| WO | WO 2020/079207 A1 | 4/2020 | |
| WO | WO 2020/086732 A1 | 4/2020 | |
| WO | WO 2020/102096 A1 | 5/2020 | |
| WO | WO 2020/104657 A1 | 5/2020 | |
| WO | WO 2020/208249 A1 | 10/2020 | |
| WO | WO 2021/032588 A1 | 2/2021 | |
| WO | WO 2021/032591 A1 | 2/2021 | |
| WO | WO 2021/043966 A1 | 3/2021 | |
| WO | WO 2021/165245 A1 | 8/2021 | |

OTHER PUBLICATIONS

Brown, "Bioisosteres in Medicinai Chemistry" Published by Wiiey-VCH Veriag GmbH & Co. KGaA, Weinheim, Germany, (2012).
CAS 1026500-66-2; STN Entry Date: Jun. 8, 2008; CN Compound Name: 2-Thiophenesulfonamide, 5-chloro-N-[[[2-ethyl-4-[7-fluoro-6-(methylamino)-1-oxo-2(1H)-isoquinolinyl]-6-methylphenyl]amino]carbonyl]—(CA Index Name).
CAS 1026685-26-6; STN Entry Date: Jun. 9, 2008; CN Compound Name: 2-Thiophenesulfonamide, 5-chloro-N-[[[5-[6-(ethylamino)-7-fluoro-1-oxo-2(1H)-isoquinolinyl]-3-methyl-2-pyridinyl]amino]carbonyl]—(CA Index Name).
CAS 1026892-76-1; STN Entry Date: Jun. 16, 2008; CN Compound Name: Benzamide, 2,3,4,5,6-pentafluoro-N-[2-[4-[[[[(2,3,4-trifluorophenyl)amino]carbonyl]amino]sulfonyl]phenyl]ethyl]—(CA Index Name).
CAS 1027977-57-6; STN Entry Date: Jun. 13, 2008; CN Compound Name: 2-Thiophenesulfonamide, 5-chloro-N-[[[4-[6-(ethylamino)-7-fluoro-1-oxo-2(1H)-isoquinolinyl]-2-(2-hydroxyethoxy)-6-methylphenyl]amino]carbonyl]—(CA Index Name).
CAS1104843-72-3 STN Entry Date:1986; CN Compound Name: 1H-Pyrazole-4-carboxylic acid, 5-[[[[(4,6-dimethyl-1-oxido-2-pyrimidinyl)amino]carbonyl]amino]sulfonyl]-1-(2-pyridinyl)-, ethyl ester (CA Index Name).
CAS 123807-74-8; STN Entry Date: 1995; CN Compound Name: 2H-1,2,5-Thiadiazino[5,6-a]indole-10-sulfonamide, N-[[(3-cyano-4,6-dimethyl-2-pyridinyl)amino]carbonyl]-2-methyl-1,1-dioxide (CA Index Name).
CAS 1332606-77-5; STN Entry Date: Sep. 16, 2011; CN Compound Name: 2-(3-(3-Amino-4-(tert-butoxycarbonyl)phenylsulfonyl)ureido)-4-chlorobenzoic acid.

(56) References Cited

OTHER PUBLICATIONS

CAS 1347649-72-2; STN Entry Date: Dec. 2, 2001; CN Compound Name: 2-Thiophenesulfonamide, 5-chloro-N-[[[4-[7-fluoro-6-(methylamino)-1-oxo-2(1H)-isoquinolinyl]-2-(methoxymethoxy)phenyl]amino]carbonyl]—(CA Index Name).
CAS 170648-58-5; STN Entry Date: 1995; CN Compound Name: Acetamide, N-[5-[[[[(2,3-dihydro-1,5-dimethyl-3-oxo-2-phenyl-1H-pyrazol-4-yl)amino]carbonyl]amino]sulfonyl]-1,3,4-thiadiazol-2-yl]—(CA Index Name).
CAS 210826-40-7; STN Entry Date: Sep. 3, 1998; CN Compound Name: 2-Furansulfonamide, N-[[(1,2,3,5,6,7-hexahydro-s-indacen-4-yl)amino]carbonyl]-4-(1-hydroxy-1-methylethyl)—(CA Index Name).
CAS 36628-63-4; STN Entry Date: 1972; CN Compound Name: Benzamide, N-[2-[5-[[[(bicyclo[2 .2]oct-5-en-2-ylamino)carbonyl]amino]sulfonyl]-2-thienyl]ethyl]-5-chloro-2-methoxy—(CA Index Name).
CAS 438013-57-1; STN Entry Date: Jul. 10, 2002; CN Compound Name: 2-Thiophenesulfonamide, 5-methyl-N-[(1-naphthalenylamino)carbonyl]—(CA Index Name).
CAS 663215-37-0; STN Entry Date: Mar. 15, 2004; CN Compound Name: 1H-1,2,4-Triazole-1-carboxamide, N-(2-chlorophenyl)-5-[[[[(2-chlorophenyl)amino]carbonyl]amino]sulfonyl]—(CA Index Name).
CAS 84884-90-2; STN Entry Date: 1983; CN Compound Name: Acetamide, N-15-[[[[(2-methylphenyl)amino)thioxomethyl]amino]sulfonyl]-1,3,4-thiadiazol-2-yl]—(CA Index Name).
CAS 907958-32-1; STN Entry Date: Sep. 20, 2006; CN Compound Name: Acetamide, N-[5-[[[[(2,5-dioxo-4-imidazolidinyl)amino]carbonyl]amino]sulfonyl]-4-methyl-2-thiazolyl]—(CA Index Name).
CAS 959378-15-5; STN Entry Date: Dec. 21, 2007; CN Compound Name: Benzo[b]thiophene-3-carboxylic acid,4,5,6,7-tetrahydro-6,6-dimethyl-2-[[[[(2-methyl-1H-imidazol-1-yl)sulfonyl]amino]carbonyl]amino]-, ethyl ester (CA Index Name).
CAS 959664-76-7; STN Entry Date: Dec. 28, 2007; CN Compound Name: Benzo[b]thiophene-3-carboxylic acid,4,5,6,7-tetrahydro-6,6-dimethyl-2-[[[[(5-methyl-1H-pyrazol-1-yl)sulfonyl]amino]carbonyl]amino]-, ethyl ester (CA Index Name).
CAS RN 1026469-15-7; STN Entry Date: Jun. 8, 2008; CN Compound Name: 2-Thiophenesulfonamide, 5-chloro-N-[[[2-(cyclopropyloxy)-4-[7-fluoro-6- (methylamino)-1-oxo-2(1H)-isoquinolinyl]phenyl]amino]carbonyl]—(CA Index Name).
CAS RN 84884-72-0; STN Entry Date: 1983; CN Compound Name: Acetamide, N-[5-[[[[(2-chlorophenyl)amino]carbonyl]amino]sulfonyl]-1,3,4-thiadiazol-2-yl]—(CA Index Name).
CAS RN 84884-75-3; STN Entry Date:1983; CN Compound Name: Acetamide, N-(5-[[[[(2-bromophenyl)amino]carbonyl]amino]sulfonyl]-1,3,4-thiadiazol-2-yl]—(CA Index Name).
CAS RN 84884-76-4; STN Entry Date: 1983; CN Compound Name: Acetamide, N-[5-[[[[(2-methylphenyl)amino]carbonyl]amino]sulfonyl]-1,3,4-thiadiazol-2-yl]—(CA Index Name).
CAS RN 84884-82-2; STN Entry Date: 1983; CN Compound Name: Acetamide, N-[5-[[[1-naphthalenylamino)carbonyl]amino]sulfonyl]-1,3,4-thiadiazol-2-yl]—(CA Index Name).
Coll, "in their own words . . . 2012 IEIIS Young Investigator Awardees," Endotoxin Newsletter, vol. 19, No. 1, Editor Jerold Weiss, PhD, Dept. of Internal Medicine, University of Iowa, (Oct. 2013).
Coll, et al., "A small-molecule inhibitor of the NLRP3 inflammasome for the treatment of inflammatory diseases," Nature Medicine, 21(3): 248-255, (2015).
Coll, et al., "Correction: The Cytokine Release inhibitory Drug CRID3 Targets ASC Oligomerisation in the NLRP3 and AIM2 Inflammasomes," PloS ONE, vol. 6, Issue 12, e29539, (Feb. 27, 2013).

Coll, et al., "Supporting Information: The Cytokine Release inhibitory Drug CRID3 Targets ASC Oligomerisation in the NLRP3 and AIM2 Inflammasomes," PloS ONE, vol. 6, Issue 12, e29539, (Feb. 27, 2013).
Coll, et al., "The Cytokine Release Inhibitory Drug CRID3 Targets ASC Oligomerisation in the NLRP3 and AIM2 Inflammasomes," PloS ONE, vol. 6, Issue 12, e29539, (Dec. 2011).
Cubrilovic, et al., "Determination of Protein—Ligand Binding Constants of a Cooperatively Regulated Tetrameric Enzyme Using Electrospray Mass Spectrometry," ACS Chemical Biology, 9(1): 218-226, (2014).
Dalvie, et al., "Biotransformation Reactions of Five-Membered Aromatic Heterocyclic Rings," Chem. Res. Toxicol., vol. 15, No. 3, pp. 269-299 (2002).
Dempsey, et al., "Cytokine release inhibitor drug, CRID3, inhibits the NLRP3 inflammasome in glia," Journal of Neuroimmunology, vol. 275(1-2), p. 147, (2014).
Dias, et al., "Synthesis of new imidazo[4,5-d][1,3]diazepine derivatives from 5-amino-4-(cyanoformimidoyl)imidazoles," Journal of Heterocyclic Chemistry, 33(3): 855-862, (1996).
El-Telbany, et al., "Synthesis of Thiophenesulphonylureas and Thioureas Structurally Related to Certain Oral Hypoglycemic drugs. Part I," Egypt Journal of Pharmaceutical Science, 16(4): 397-401, (1975).
Email from CAS Customer Center <help@cas.org>, Subject: RE: Case #66345503: question of indexing, 218-Sent: Oct. 9, 2020.
Febbraio, "Role of interleukins in obesity: implications for metabolic disease," Trends in Endocrinology and Metabolism, vol. 25, No. 6, pp. 312-319, (Jun. 2014).
Fleming, et al., "Novel axially chiral bis-arylthiourea-based organocatalysts for asymmetric Friedel-Crafts type reactions," Tetrahedron Letters, 47(39): 7037-7042, (2006).
Groß, et al. "K+ Efflux-Independent NLRP3 Inflammasome Activation by Small Molecules Targeting Mitochondria," Immunity, 45(4):761-773, (2016).
Guo, et al., "Inflammasomes: mechanism of action, role in disease, and therapeutics," Nature Medicine, vol. 21, No. 7, pp. 677-687, (Jul. 2015).
Haneklaus, et al., "Modulatory mechanisms controlling the NLRP3 inflammasome in inflammation: recent developments," Current opinion in immunology, 25, (1), pp. 40-45, (2013).
Hebeisen, et al., "Orally active aminopyridines as inhibitors of tetrameric fructose-1,6-bisphosphatase," Bioorganic & Medicinal Chemistry Letters, 21(11): 3237-3242, (2011).
Hill, et al., "Dual Action Suifonyiureas: NLRP3 Inhibition and Insulin Secretion," 1st Queensland Annual Chemistry Symposium, Poster P20, Nov. 25, 2016 (and accompanying programme).
Hill, et al., "Sulfonylureas as Concomitant Insulin Secretagogues and NLRP3 Inflammasome Inhibitors," Chem Med Chem, 12(17): 1449-1457, (2017).
Holland, "Preparation of some additionai suifonyiureas," Journal of Organic Chemistry, 26(5): 1662-1665, (1961).
Hutton, et al., "The NLRP3 inflammasome in kidney disease and autoimmunity," Nephrology, 21(9): 736-744, (2016).
Kazuto, et al., "Design, synthesis and biological activity of novel non-peptidyi endothelin converting enzyme inhibitors, 1-phenyltetrazole-formazan analogues," Bioorganic & Medicinal Chemistry Letters, 12(9): 1275-1278, (2002).
Khelili, et al., "Synthesis and vasodilator effects of 3- and 7-sulfonylurea-1,2,4-benzothiadiazin-1,1-dioxides on rat aorta," Bioorganic & Medicinal Chemistry, 3(5): 495-503, (1995).
Khuntwal, et al., "Credential role of van der waal volumes and atomic masses in modeling Hepatitis C virus NS5B polymerase inhibition by tetrahydrobenzo-thiophenes using SVM and MLR aided QSAR studies," Current Bioinformatics, 8(4): 465-471, (2013).
Kim, et al., "Role for NLRP3 Inflammasome-mediated, IL-1β-Dependent Responses in Severe, Steroid-Resistant Asthma," 196(3): 283-297, (2017).
Krishnan, et al., "Inflammasome activity is essential for one kidney/deoxycorticosterone acetate/salt-induced hypertension in mice," British Journal of Pharmacology, 173(4): 752-765, (2016).
Laliberte, et al., "Glutathione S-transferase omega 1-1 is a target of cytokine release inhibitory drugs and may be responsible for their

(56) References Cited

OTHER PUBLICATIONS effect on interleukin-1B posttranslational processing," Journal of Biological Chemistry, 278(19): 16567-16578, (2003).
Laporte, et al., "Tetrahydrobenzothiophene inhibitors of hepatitis C virus NS5B polymerase," Bioorganic & Medicinal Chemistry Letters, 16(1): 100-103, (2006).
Lerner, et al. "*Mycobacterium tuberculosis* replicates within necrotic human macrophages," Journal of Cell Biology, 216(3): 583-594, (2017).
Li, et al., "Discovery of the first SecA inhibitors using structure-based virtual screening," Biochemical and Biophysical Research Communications, 368(4): 839-845, (2008).
Luckhurst, et al., "A convenient synthesis of suifonyiureas from carboxylic acids and sulfonamides via an in situ Curtius rearrangement," Tetrahedron Letters, 48(50): 8878-8882, (2007).
Ludwig-Porfugall, et al., "An NLRP3-specific inflammasome inhibitor attenuates crystal-induced kidney fibrosis in mice," Kidney International, 90(3): 525-539, (2016).
Mokhtar, et al., "Synthesis of nitrogenous compounds. Part III," Pakistan Journal of Scientific and Industrial Research, 34(1): pp. 9-15, (1991).
Monnerat, et al., "Macrophage-dependent IL-1β production induces cardiac arrhythmias in diabetic mice," Nature Communications, 7(13344): 1-15, (2016).
Mridha, et al., "NLRP3 infiammasome blockade reduces liver inflammation and fibrosis in experimental NASH in mice," Journal of Hepatology, 66(5): 1037-1046, (2017).
Mullen, et al., "Pattern recognition receptors as potential therapeutic targets in inflammatory rheumatic disease," Arthritis Research & Therapy, 17:122, (2015).
Ouf, et al., "Sulphonyl Ureas and Thioureas of 1,3,4-Thiodiazole to be Tested as Hypoglycomic Agents," Egyptian Journal of Pharmaceutical Sciences, 21(3-4): 189-198, (1980).
Ouf, et al., "Thiophene sulphonylureas structurally related to antidiabetic drugs," Journal of Drug Research Egypt, 6(2): 123-129, (1974).
Pacini, et al., "2-(3-Thienyl)-5,6-dihydroxypyrimidine-4-carboxylic acids as inhibitors of HCV NS5B RdRp," Bioorganic & Medicinal Chemistry Letters, 19(21): 6245-6249, (2009).
Pinar, et al., "PB1-F2 Peptide Derived from Avian influenza A Virus H7N9 Induces Inflammation via Activation of the NLRP3 Inflammasome," Journal of Biological Chemistry, 292(3): 826-836, (2017).
Proks, et al., "Sulfonylurea stimuiation of insulin secretion," Diabetes, 51(3): S368-S376, (2002).
Rotroff, et al., "Predictive Endocrine Testing in the 21st Century Using in Vitro Assays of Estrogen Receptor Signaling Responses," Environmental Science & Technology, 48(15): 8706-8716, (2014).
Saczewski, et al., "Synthesis of Novel Aryl(heteroaryl)sulfonyl Ureas of Possible Biological Interest," Molecules, 15(3): 1113-1126, (2010).
Salla, et al., "Identification, Synthesis, and Biological Evaluation of the Major Human Metabolite of NLRP3 Inflammasome Inhibitor MCC950," ACS Medicinal Chemistry Letters, 7(12): 1034-1038, (2016).
Sarges, et al., "Suifamylurea hypoglycemic agents. 6. High potency derivatives," Journal of Medicinal Chemistry, 19(5): 695-709, (1976).
Shah, et al., "Analysis of Pfizer Compounds in EPA's ToxCast Chemicals-Assay Space," Chemical Research in Toxicology, 2014, 27(1), 86-98: (2014).
Shah, et al., "Setting Clinical Exposure Levels of Concern for Drug-Induced Liver injury (DILI) Using Mechanistic in vitro Assays," Toxicological Sciences, 147(2): 500-514, (2015).
Sipes, et al., "Profiling 976 ToxCast Chemicals across 331 Enzymatic and Receptor Signaling Assays," Chemical Research in Toxicology, 26(6): 878-895, (2013).
St Jean, et al., "Mitigating Heterocycle Metabolism in Drug Discovery," Journal of Medicinal Chemistry, 55, pp. 6002-6020, (2012).
Stocks, et al., "On Chemistry, On Medical Chemistry," Published in Great Britain by Sci-Ink Limited, ISBN 978-0-9550072-3-1, pp. 214-215, (2007).

Urban, et al., "Novel Synthesis of 1-(1,2,3,5,6,7-Hexahydro-s-indacen-4-yl)-3-[4-(1-hydroxy-1-methyl-ethyl)-furan-2-sulfonyl]urea, an Anti-inflammatory Agent," Synthetic Communications, 33(12): 2029-2043, (2003).
Wambaugh, et al., "High-Throughput Models for Exposure-Based Chemical Prioritization in the ExpoCast Project," Environmental Science & Technology, 47(15): 8479-8488, (2013).
Waterman, et al. "Improved Protocol and Data Analysis for Accelerated Shelf-Life Estimation of Solid Dosage Forms," Pharmaceutical Research, 24(4): 780-790, (2007).
Youssef, et al., "N1,N3-Diaryl sulfonylureas as possible anticancer agents," Alexandria Journal of Pharmaceutical Sciences, 8(3): 223-225, (1994).
Youssef, et al., "Synthesis of sulofenur analogues as antitumour agents: part II," Medicinal Chemistry Research, 11(9): 481-503, (2002).
Zhen, et al., "Recent advances in discovery and development of promising therapeutics against Hepatitis C virus NS5B RNA-dependent RNA polymerase," Mini Reviews in Medicinal Chemistry, 5(12): 1103-1112, (2005).
GB Application No. GB1713082.4 Search Report under Section 17(5) dated Apr. 30, 2018.
GB Application No. GB1721727.4 Search Report under Section 17(5) dated Sep. 17, 2018.
GB Application No. GB1721729.0 Search Report under Section 17(5) dated Aug. 30, 2018.
GB Application No. GB1721731.6 Search Report under Section 17(5) dated Sep. 3, 2018.
GB Application No. GB1721732.4 Search Report under Section 17(5) dated Sep. 3, 2018.
GB Application No. GB1721735.7 Search Report under Section 17(5) dated Aug. 30, 2018.
GB Application No. GB1721736.5 Search Report under Section 17(5) dated Aug. 30, 2018.
GB Application No. GB1803391.0 Search Report under Section 17(5) dated Oct. 16, 2018.
GB Application No. GB1803392.8 Search Report under Section 17(5) dated Oct. 16, 2018.
U.S. Appl. No. 16/638,648, Requirement for Restriction/Election dated Apr. 20, 2021.
U.S. Application No. 16/7611,993, Requirement for Restriction/Election dated Apr. 9, 2021.
WIPO Application No. PCT/EP2018/072111, PCT International Preliminary Report on Patentability dated Feb. 27, 2020.
WIPO Application No. PCT/EP2018/072111, PCT International Search Report and Written Opinion of the International Searching Authority dated Nov. 6, 2018.
WIPO Application No. PCT/EP2018/072115, PCT International Preliminary Report on Patentability dated Feb. 27, 2020.
WIPO Application No. PCT/EP2018/072115, PCT International Search Report and Written Opinion of the International Searching Authority dated Oct. 24, 2018.
WIPO Application No. PCT/EP2018/072119, PCT International Preliminary Report on Patentability dated Feb. 27, 2020.
WIPO Application No. PCT/EP2018/072119, PCT International Search Report and Written Opinion of the International Searching Authority dated Dec. 11, 2018.
WIPO Application No. PCT/EP2018/072123, PCT International Preliminary Report on Patentability dated Feb. 27, 2020.
WIPO Application No. PCT/EP2018/072123, PCT International Search Report and Written Opinion of the International Searching Authority dated Nov. 14, 2018.
WIPO Application No. PCT/EP2018/072125, PCT International Preliminary Report on Patentability dated Feb. 27, 2020.
WIPO Application No. PCT/EP2018/072125, PCT International Search Report and Written Opinion of the International Searching Authority dated Oct. 22, 2018.
WIPO Application No. PCT/EP2018/080737, PCT International Preliminary Report on Patentability dated May 22, 2020.
WIPO Application No. PCT/EP2018/080737, PCT International Search Report and Written Opinion of the International Searching Authority dated Jan. 30, 2019.

(56) References Cited

OTHER PUBLICATIONS

WIPO Application No. PCT/EP2018/080739, PCT International Preliminary Report on Patentability dated May 22, 2020.
WIPO Application No. PCT/EP2018/080739, PCT International Search Report and Written Opinion of the International Searching Authority dated Jan. 25, 2019.
WIPO Application No. PCT/EP2018/080746, PCT International Preliminary Report on Patentability dated May 22, 2020.
WIPO Application No. PCT/EP2018/080746, PCT International Search Report and Written Opinion of the International Searching Authority dated Jan. 25, 2019.
WIPO Application No. PCT/EP2019/055127, PCT International Preliminary Report on Patentability dated Sep. 17, 2020.
WIPO Application No. PCT/EP2019/055127, PCT International Search Report and Written Opinion of the International Searching Authority dated Apr. 24, 2019.
WIPO Application No. PCT/IB2017/053059, PCT International Preliminary Report on Patentability dated Dec. 5, 2019.
WIPO Application No. PCT/IB2017/053059, PCT International Search Report and Written Opinion of the International Searching Authority dated Aug. 8, 2017.
Balant, et al., "Metabolic Considerations in Prodrug Design," Burger's Medicinal Chemistry and Drug Discovery, 5th Edition, vol. 1; Principles and Practice, pp. 949-982, Editied by Manfred E. Wolff, © 1995 John Wiley & Sons, Inc.
Banker, et al., Prodrugs, Modern Pharmaceutics, 3rd edition, Revised and Expanded, pp. 451 and 596, (1995).
Bundgaard, "Design of Prodrugs," Chapter1, p. 1, (1985).
Ettmayer, et al., "Perspective, Lessons Learned from Marketed and Investigational Prodrugs," Journal of Medicinal Chemistry, vol. 47, No. 10, 2393-2404, (May 6, 2004).
Himiceskij, Chemical Encyclopedia, (1983), p. 130-131, Brief statement of relevance.
Jordan, "Tamoxifen: A Most Unlikely Pioneering Medicine," Nature Reviews, Drug Discovery, vol. 2, 205-213, (Mar. 2003).
Silverman, "The Organic Chemistry of Drug Design and Drug Action," Prodrugs and Drug Delivery Stystem, The Organic Chemistry of Drug Design and Drug Action, Chapter 8, pp. 352-400, (1992).
Stella, "Prodrugs as therapeutics," Xpert Opin. Ther. Patients, 14(3): 277-280, (2664).
Tesfa, "Prodrug research: futile or fertile," Biochemical Pharmacology, 68, 2697-2106, (2004).
U.S. Appl. No. 16/638,648, Non-Final Office Action dated Dec. 16, 2021.
U.S. Appl. No. 16/638,700, Non-Final Office Action dated Sep. 10, 2021.
U.S. Appl. No. 16/638,700, Requirement for Restriction/Election dated May 3, 2021.
U.S. Appl. No. 16/638,704, Requirement for Restriction/Election dated Apr. 29, 2021.
U.S. Appl. No. 16/638,707, Non-Final Office Action dated Oct. 15, 2021.
U.S. Appl. No. 16/638,707, Requirement for Restriction/Election dated May 13, 2021.
U.S. Appl. No. 16/761,993, Non-Final Office Action dated Aug. 16, 2021.
U.S. Appl. No. 16/762,000, Requirement for Restriction/Election dated Nov. 1, 2021.
Belikov, et aL., "MEDpress-inform," Pharmaceuticai chemistry, Text Book, 4th Edition, Moscow, 622 pages, 11, 27-29, (2007), Brief statement of relevance.
Belikov, et al., "The interconnection between chemical structure, properties of substances and their effect on the body", MEDpress-inform, Pharmaceutical Chemistry, Text Book, 4th Edition, Moscow, Chap. 2.6, 27-29, (2007), Brief statement of relevance.
Disease—Wikipedia, retrieved from the internet on Jan. 5, 2022 at: https://en.wikipedia.org/wiki/Disease.
Gavrilov, et al., Pharmaceutical Technology, Preparation of Medicaments, Text Book, Moscow Publishing group "GEOTAR-Media", 2010, 624, p. 20, Brief statement of relevance.
Guidelines for Conducting Preclinical Drug Studies. Part one. M.: Grifand K, 2012, 944 p., ed. Mironova A.N, Brief statement of relevance.
Han, "Targeted Prodrug Design to Optimize Drug Delivery," AAPS Pharmsci, 2 (1) article 6, 1-11, (2000).
Mashkovskly, "Medicaments," Moscow, "Medicine", 1993, chapter 1, p. 8, Brief statement of relevance.
Parajuli, et al., "Prodrug as a novel approach of drug delivery—a review," Journal of Drug Delivery & Therapeutics, 5(3), pp. 5-9, (2015).
Solvation—Wikipedia, retrieved from the internet on Jan. 5, 2022 at: https://en.wikipedia.org/wiki/Solvation.
Zawilska, et al., "Prodrugs: a challenge for the drug development," Pharmacological reports: PR, vol. 65, No. 1, pp. 1-14, (Apr. 2013).
Zhulenko, et al., "Pharmacology", Moscow: KolosS, p. 34-35, (2608), Brief statement of relevance.
RU Application No. 2626116219/04(017079) Office Action and Search Report dated Feb. 15, 2022, English tranlsation of office action.
U.S. Appl. No. 16/638,648, Final Office Action dated May 27, 2022.
U.S. Appl. No. 16/638,766, Final Office Action dated May 16, 2022.
U.S. Appl. No. 16/638,707, Notice of Allowance and interview Summary dated Apr. 21, 2022.
U.S. Appl. No. 16/761,993, Non-Final Office Action dated Apr. 6, 2022.
U.S. Appl. No. 16/762,000, Non-Final Office Action dated Apr. 4, 2022.
U.S. Appl. No. 16/638,764, Final Office Action dated Jul. 8, 2022.
Dorwald, "Side Reactions in Organic Synthesis, a Guide to Successful Synthesis Design," Wiley-VCH, 11 pages, (2005).
Hamarsheh, et al., "NLPR3 Inflammasome Activation in Cancer: A Double-edged Sword," Frontiers in Immunology, 11:1444, (Jul. 2020).
Kim, et al., "NLPR3 Inflammasome and Host Protection against Bacterial Infection," J. Korean Med Sci, 28: 1415-1423, (Oct. 2013).
Meanwell, "Fluorine and Fluorinated Motifs in the Design and Application of Bioisosteres for Drug Design," J. Med. Chem, 61, 5822-5880, (Feb. 2018).
Moossavi, et al., "Role of the NLRP3 inflammasome in cancer," Molecular Cancer, 17:158, (2018).
Mortimer, et al., "NLRP3 inflammasome inhibition is disrupted in a group of auto-inflammatory disease CAPS mutations," Nature Immunology, vol. 17, No. 10, 1176-1186, (Oct. 2016).
Shao, et al,. "Targeting NLRP3 Inflammasome in the Treatment fo CNS Diseases," Front. Mol Neurosci, 11:320, (Sep. 2018).
Sita, et al., "NLRP3 and Infections: β-Amyloid in Inflammasome beyond Neurodegeneration," Int. J. Mol. Sci, 22, 6984, (Jun. 2021).
Song, et al., "NLRP3 Inflammasome in Neurological Diseases, from Functions to Therapies," Front. Cell. Neurosci 11:63, doi: 10.3389/Incel.2017.00063, (Mar. 2017).
Zhao, et al., "NLRP3 Inflammasome—A Key Player in Antiviral Responses," Frontiers in Immunology, vol. 11, Article 211, (Feb. 2020).
EP 19708309.0 Commuication pursuant to Article 94(3) dated Mar. 23, 2023.
U.S. Appl. No. 16/638,648, Notice of Allowance dated Oct. 18, 2022.
U.S. Appl. No. 16/638,648, Supplemental Notice of Allowance dated Jan. 20, 2023.
U.S. Appl. No. 16/638,700, Non-Final Office Action dated Oct. 19, 2022.
U.S. Appl. No. 16/638,704, Non-Final Office Action dated Dec. 30, 2022.
U.S. Appl. No. 16/638,707, Notice of Allowance dated Sep. 7, 2022.
U.S. Appl. No. 16/761, 993, Non-Final Office Action dated Oct. 12, 2022.
U.S. Appl. No. 16/762,000, Final Office Action dated Nov. 15, 2022.
U.S. Appl. No. 16/638,700, Final Office Action dated Mar. 20, 2023.
U.S. Appl. No. 16/761,993, Final Office Action dated Feb. 28, 2023.

(56) References Cited

OTHER PUBLICATIONS

U.S. Appl. No. 16/761,993, Non-Final Office Action dated Jul. 17, 2023.
U.S. Appl. No. 16/762,000, Non-Final Office Action dated Apr. 26, 2023.
U.S. Appl. No. 16/638,700, Notice of Allowance and Interview Summary dated Sep. 29, 2023.
U.S. Appl. No. 16/638,704, Final Office Action dated Oct. 3, 2023.
U.S. Appl. No. 16/762,000, Non-Final Office Action dated Dec. 26, 2023.

COMPOUNDS

CROSS-REFERENCE TO RELATED APPLICATIONS

This application is a national stage entry of PCT/EP2019/055127 filed Mar. 1, 2019, which claims the benefit of GB Patent Application No. 1803392.8 filed, Mar. 2, 2018 and GB Patent Application No. 1813284.5 filed, Aug. 15, 2018.

FIELD OF THE INVENTION

The present invention relates to sulfonylureas and sulfonylthioureas comprising a 5-membered heteroaryl ring attached to the sulfonyl group, wherein the heteroaryl ring is di-substituted at the 3- and 4-positions relative to the point of attachment of the sulfonyl group, and wherein the group attached to the terminal nitrogen atom of the urea group is either a 1,2,3,5,6,7-hexahydro-s-indacen-4-yl group substituted at the 8-position, or a heteroaryl group substituted at the $\alpha$ and $\alpha'$ positions. The present invention further relates to salts, solvates and prodrugs of such compounds, to pharmaceutical compositions comprising such compounds, and to the use of such compounds in the treatment and prevention of medical disorders and diseases, most especially by NLRP3 inhibition.

BACKGROUND

The NOD-like receptor (NLR) family, pyrin domain-containing protein 3 (NLRP3) inflammasome is a component of the inflammatory process, and its aberrant activity is pathogenic in inherited disorders such as cryopyrin-associated periodic syndromes (CAPS) and complex diseases such as multiple sclerosis, type 2 diabetes, Alzheimer's disease and atherosclerosis.

NLRP3 is an intracellular signalling molecule that senses many pathogen-derived, environmental and host-derived factors. Upon activation, NLRP3 binds to apoptosis-associated speck-like protein containing a caspase activation and recruitment domain (ASC). ASC then polymerises to form a large aggregate known as an ASC speck. Polymerised ASC in turn interacts with the cysteine protease caspase-1 to form a complex termed the inflammasome. This results in the activation of caspase-1, which cleaves the precursor forms of the proinflammatory cytokines IL-1β and IL-18 (termed pro-IL-1β and pro-IL-18 respectively) to thereby activate these cytokines. Caspase-1 also mediates a type of inflammatory cell death known as pyroptosis. The ASC speck can also recruit and activate caspase-8, which can process pro-IL-1β and pro-IL-18 and trigger apoptotic cell death.

Caspase-1 cleaves pro-IL-1β and pro-IL-18 to their active forms, which are secreted from the cell. Active caspase-1 also cleaves gasdermin-D to trigger pyroptosis. Through its control of the pyroptotic cell death pathway, caspase-1 also mediates the release of alarmin molecules such as IL-33 and high mobility group box 1 protein (HMGB1). Caspase-1 also cleaves intracellular IL-1R2 resulting in its degradation and allowing the release of IL-1α. In human cells caspase-1 may also control the processing and secretion of IL-37. A number of other caspase-1 substrates such as components of the cytoskeleton and glycolysis pathway may contribute to caspase-1-dependent inflammation.

NLRP3-dependent ASC specks are released into the extracellular environment where they can activate caspase-1, induce processing of caspase-1 substrates and propagate inflammation.

Active cytokines derived from NLRP3 inflammasome activation are important drivers of inflammation and interact with other cytokine pathways to shape the immune response to infection and injury. For example, IL-1β signalling induces the secretion of the pro-inflammatory cytokines IL-6 and TNF. IL-1β and IL-18 synergise with IL-23 to induce IL-17 production by memory CD4 Th17 cells and by γδ T cells in the absence of T cell receptor engagement. IL-18 and IL-12 also synergise to induce IFN-γ production from memory T cells and NK cells driving a Th1 response.

The inherited CAPS diseases Muckle-Wells syndrome (MWS), familial cold autoinflammatory syndrome (FCAS) and neonatal-onset multisystem inflammatory disease (NOMID) are caused by gain-of-function mutations in NLRP3, thus defining NLRP3 as a critical component of the inflammatory process. NLRP3 has also been implicated in the pathogenesis of a number of complex diseases, notably including metabolic disorders such as type 2 diabetes, atherosclerosis, obesity and gout.

A role for NLRP3 in diseases of the central nervous system is emerging, and lung diseases have also been shown to be influenced by NLRP3. Furthermore, NLRP3 has a role in the development of liver disease, kidney disease and aging. Many of these associations were defined using Nlrp3−/− mice, but there have also been insights into the specific activation of NLRP3 in these diseases. In type 2 diabetes mellitus (T2D), the deposition of islet amyloid polypeptide in the pancreas activates NLRP3 and IL-1β signaling, resulting in cell death and inflammation.

Several small molecules have been shown to inhibit the NLRP3 inflammasome. Glyburide inhibits IL-1β production at micromolar concentrations in response to the activation of NLRP3 but not NLRC4 or NLRP1. Other previously characterised weak NLRP3 inhibitors include parthenolide, 3,4-methylenedioxy-β-nitrostyrene and dimethyl sulfoxide (DMSO), although these agents have limited potency and are nonspecific.

Current treatments for NLRP3-related diseases include biologic agents that target IL-1. These are the recombinant IL-1 receptor antagonist anakinra, the neutralizing IL-1β antibody canakinumab and the soluble decoy IL-1 receptor rilonacept. These approaches have proven successful in the treatment of CAPS, and these biologic agents have been used in clinical trials for other IL-1β-associated diseases.

Some diarylsulfonylurea-containing compounds have been identified as cytokine release inhibitory drugs (CRIDs) (Perregaux et al.; J. Pharmacol. Exp. Ther. 299, 187-197, 2001). CRIDs are a class of diarylsulfonylurea-containing compounds that inhibit the post-translational processing of IL-1β. Post-translational processing of IL-1β is accompanied by activation of caspase-1 and cell death. CRIDs arrest activated monocytes so that caspase-1 remains inactive and plasma membrane latency is preserved.

Certain sulfonylurea-containing compounds are also disclosed as inhibitors of NLRP3 (see for example, Baldwin et al., J. Med. Chem., 59(5), 1691-1710, 2016; and WO 2016/131098 A1, WO 2017/129897 A1, WO 2017/140778 A1, WO 2017/184604 A1, WO 2017/184623 A1, WO 2017/184624 A1, WO 2018/136890 A1 and WO 2018/015445A1).

There is a need to provide compounds with improved pharmacological and/or physiological and/or physicochemical properties and/or those that provide a useful alternative to known compounds.

SUMMARY OF THE INVENTION

A first aspect of the invention provides a compound of formula (I):

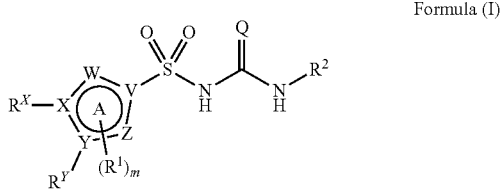

Formula (I)

wherein:
Q is selected from O or S;
V, X and Y are each independently selected from C and N, and W and Z are each independently selected from N, O, S, NH and CH, provided that at least one of V, W, X, Y and Z is N, O, S or NH;
$R^X$ and $R^Y$ are each independently a halo, —OH, —NO$_2$, —NH$_2$, —N$_3$, —SH, —SO$_2$H, —SO$_2$NH$_2$, or a saturated or unsaturated hydrocarbyl group, wherein the hydrocarbyl group may be straight-chained or branched, or be or include cyclic groups, wherein the hydrocarbyl group may optionally be substituted, and wherein the hydrocarbyl group may optionally include one or more heteroatoms N, O or S in its carbon skeleton;
optionally $R^X$ and $R^Y$ together with the atoms X and Y to which they are attached may form a 4- to 12-membered saturated or unsaturated cyclic group fused to ring A, wherein the cyclic group fused to ring A may optionally be substituted;
m is 0, 1 or 2;
each $R^1$ is independently a halo, —OH, —NO$_2$, —NH$_2$, —N$_3$, —SH, —SO$_2$H, —SO$_2$NH$_2$, or a saturated or unsaturated hydrocarbyl group, wherein the hydrocarbyl group may be straight-chained or branched, or be or include cyclic groups, wherein the hydrocarbyl group may optionally be substituted, and wherein the hydrocarbyl group may optionally include one or more heteroatoms N, O or S in its carbon skeleton;
optionally $R^X$ and any $R^1$ attached to W may together with the atoms W and X to which they are attached form a 4- to 12-membered saturated or unsaturated cyclic group fused to ring A, wherein the cyclic group fused to ring A may optionally be substituted;
optionally $R^Y$ and any $R^1$ attached to Z may together with the atoms Y and Z to which they are attached form a 4- to 12-membered saturated or unsaturated cyclic group fused to ring A, wherein the cyclic group fused to ring A may optionally be substituted; and
$R^2$ is selected from:
(i) a group having the formula:

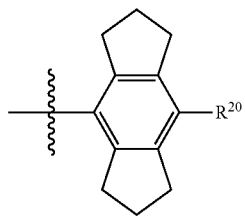

wherein $R^{20}$ is a halo, —OH, —NO$_2$, —NH$_2$, —N$_3$, —SH, —SO$_2$H, —SO$_2$NH$_2$, or a saturated or unsaturated hydrocarbyl group, wherein the hydrocarbyl group may be straight-chained or branched, or be or include cyclic groups, wherein the hydrocarbyl group may optionally be substituted, and wherein the hydrocarbyl group may optionally include one or more heteroatoms N, O or S in its carbon skeleton; or
(ii) a heteroaryl group substituted at the α and α' positions, wherein $R^2$ may optionally be further substituted.

In the context of the present specification, a "hydrocarbyl" substituent group or a hydrocarbyl moiety in a substituent group only includes carbon and hydrogen atoms but, unless stated otherwise, does not include any heteroatoms, such as N, O or S, in its carbon skeleton. A hydrocarbyl group/moiety may be saturated or unsaturated (including aromatic), and may be straight-chained or branched, or be or include cyclic groups wherein, unless stated otherwise, the cyclic group does not include any heteroatoms, such as N, O or S, in its carbon skeleton. Examples of hydrocarbyl groups include alkyl, alkenyl, alkynyl, cycloalkyl, cycloalkenyl and aryl groups/moieties and combinations of all of these groups/moieties. Typically a hydrocarbyl group is a $C_1$-$C_{20}$ hydrocarbyl group. More typically a hydrocarbyl group is a $C_1$-$C_{15}$ hydrocarbyl group. More typically a hydrocarbyl group is a $C_1$-$C_{10}$ hydrocarbyl group. A "hydrocarbylene" group is similarly defined as a divalent hydrocarbyl group.

An "alkyl" substituent group or an alkyl moiety in a substituent group may be linear (i.e. straight-chained) or branched. Examples of alkyl groups/moieties include methyl, ethyl, n-propyl, i-propyl, n-butyl, i-butyl, t-butyl and n-pentyl groups/moieties. Unless stated otherwise, the term "alkyl" does not include "cycloalkyl". Typically an alkyl group is a $C_1$-$C_{12}$ alkyl group. More typically an alkyl group is a $C_1$-$C_6$ alkyl group. An "alkylene" group is similarly defined as a divalent alkyl group.

An "alkenyl" substituent group or an alkenyl moiety in a substituent group refers to an unsaturated alkyl group or moiety having one or more carbon-carbon double bonds. Examples of alkenyl groups/moieties include ethenyl, propenyl, 1-butenyl, 2-butenyl, 1-pentenyl, 1-hexenyl, 1,3-butadienyl, 1,3-pentadienyl, 1,4-pentadienyl and 1,4-hexadienyl groups/moieties. Unless stated otherwise, the term "alkenyl" does not include "cycloalkenyl". Typically an alkenyl group is a $C_2$-$C_{12}$ alkenyl group. More typically an alkenyl group is a $C_2$-$C_6$ alkenyl group. An "alkenylene" group is similarly defined as a divalent alkenyl group.

An "alkynyl" substituent group or an alkynyl moiety in a substituent group refers to an unsaturated alkyl group or moiety having one or more carbon-carbon triple bonds. Examples of alkynyl groups/moieties include ethynyl, propargyl, but-1-ynyl and but-2-ynyl groups/moieties. Typically an alkynyl group is a $C_2$-$C_{12}$ alkynyl group. More typically an alkynyl group is a $C_2$-$C_6$ alkynyl group. An "alkynylene" group is similarly defined as a divalent alkynyl group.

A "cyclic" substituent group or a cyclic moiety in a substituent group refers to any hydrocarbyl ring, wherein the hydrocarbyl ring may be saturated or unsaturated (including aromatic) and may include one or more heteroatoms, e.g. N, O or S, in its carbon skeleton. Examples of cyclic groups include cycloalkyl, cycloalkenyl, heterocyclic, aryl and heteroaryl groups as discussed below. A cyclic group may be monocyclic, bicyclic (e.g. bridged, fused or spiro), or polycyclic. Typically, a cyclic group is a 3- to 12-membered cyclic group, which means it contains from 3 to 12 ring atoms. More typically, a cyclic group is a 3- to 7-membered monocyclic group, which means it contains from 3 to 7 ring atoms.

A "heterocyclic" substituent group or a heterocyclic moiety in a substituent group refers to a cyclic group or moiety including one or more carbon atoms and one or more (such as one, two, three or four) heteroatoms, e.g. N, O or S, in the ring structure. Examples of heterocyclic groups include heteroaryl groups as discussed below and non-aromatic heterocyclic groups such as azetinyl, azetidinyl, oxetanyl, thietanyl, pyrrolidinyl, tetrahydrofuranyl, tetrahydrothiophenyl, pyrazolidinyl, imidazolidinyl, dioxolanyl, oxathiolanyl, piperidinyl, tetrahydropyranyl, thianyl, piperazinyl, dioxanyl, morpholinyl and thiomorpholinyl groups.

A "cycloalkyl" substituent group or a cycloalkyl moiety in a substituent group refers to a saturated hydrocarbyl ring containing, for example, from 3 to 7 carbon atoms, examples of which include cyclopropyl, cyclobutyl, cyclopentyl and cyclohexyl. Unless stated otherwise, a cycloalkyl substituent group or moiety may include monocyclic, bicyclic or polycyclic hydrocarbyl rings.

A "cycloalkenyl" substituent group or a cycloalkenyl moiety in a substituent group refers to a non-aromatic unsaturated hydrocarbyl ring having one or more carbon-carbon double bonds and containing, for example, from 3 to 7 carbon atoms, examples of which include cyclopent-1-en-1-yl, cyclohex-1-en-1-yl and cyclohex-1,3-dien-1-yl. Unless stated otherwise, a cycloalkenyl substituent group or moiety may include monocyclic, bicyclic or polycyclic hydrocarbyl rings.

An "aryl" substituent group or an aryl moiety in a substituent group refers to an aromatic hydrocarbyl ring. The term "aryl" includes monocyclic aromatic hydrocarbons and polycyclic fused ring aromatic hydrocarbons wherein all of the fused ring systems (excluding any ring systems which are part of or formed by optional substituents) are aromatic. Examples of aryl groups/moieties include phenyl, naphthyl, anthracenyl and phenanthrenyl. Unless stated otherwise, the term "aryl" does not include "heteroaryl".

A "heteroaryl" substituent group or a heteroaryl moiety in a substituent group refers to an aromatic heterocyclic group or moiety. The term "heteroaryl" includes monocyclic aromatic heterocycles and polycyclic fused ring aromatic heterocycles wherein all of the fused ring systems (excluding any ring systems which are part of or formed by optional substituents) are aromatic. Examples of heteroaryl groups/moieties include the following:

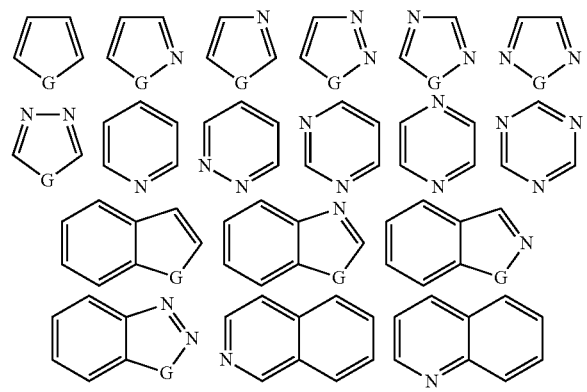

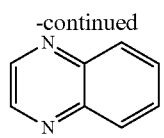

wherein G=O, S or NH.

For the purposes of the present specification, where a combination of moieties is referred to as one group, for example, arylalkyl, arylalkenyl, arylalkynyl, alkylaryl, alkenylaryl or alkynylaryl, the last mentioned moiety contains the atom by which the group is attached to the rest of the molecule. An example of an arylalkyl group is benzyl.

For the purposes of the present specification, in an optionally substituted group or moiety:

(i) each hydrogen atom may optionally be replaced by a group independently selected from halo; —CN; —NO$_2$; —N$_3$; —R$^\beta$; —OH; —OR$^\beta$; —R$^\alpha$-halo; —R$^\alpha$—CN; —R$^\alpha$—NO$_2$; —R$^\alpha$—N$_3$; —R$^\alpha$—R$^\beta$; —R$^\alpha$—OH; —R$^\alpha$—OR$^\beta$; —SH; —SR$^\beta$; —SOR$^\beta$; —SO$_2$H; —SO$_2$R$^\beta$; —SO$_2$NH$_2$; —SO$_2$NHR$^\beta$; —SO$_2$N(R$^\beta$)$_2$; —R$^\alpha$—SH; —R$^\alpha$—SR$^\beta$; —R$^\alpha$—SOR$^\beta$; —R$^\alpha$—SO$_2$H; —R$^\alpha$—SO$_2$R$^\beta$; —R$^\alpha$—SO$_2$NH$_2$; —R$^\alpha$—SO$_2$NHR$^\beta$; —R$^\alpha$—SO$_2$N(R$^\beta$)$_2$; —Si(R$^\beta$)$_3$; —O—Si(R$^\beta$)$_3$; —R$^\alpha$—Si(R$^\beta$)$_3$; —R$^\alpha$—O—Si(R$^\beta$)$_3$; —NH$_2$; —NHR$^\beta$; —N(R$^\beta$)$_2$; —N(O)(R$^\beta$)$_2$; —N$^+$(R$^\beta$)$_3$; —R$^\alpha$—NH$_2$; —R$^\alpha$—NHR$^\beta$; —R$^\alpha$—N(R$^\beta$)$_2$; —R$^\alpha$—N(O)(R$^\beta$)$_2$; —R$^\alpha$—N$^+$(R$^\beta$)$_3$; —CHO; —COR$^\beta$; —COOH; —COOR$^\beta$; —OCOR$^\beta$; —R$^\alpha$—CHO; —R$^\alpha$—COR$^\beta$; —R$^\alpha$—COOH; —R$^\alpha$—COOR$^\beta$; —R$^\alpha$—OCOR$^\beta$; —C(=NH)R$^\beta$; —C(=NH)NH$_2$; —C(=NH)NHR$^\beta$; —C(=NH)N(R$^\beta$)$_2$; —C(=NR$^\beta$)R$^\beta$; —C(=NR$^\beta$)NHR$^\beta$; —C(=NR$^\beta$)N(R$^\beta$)$_2$; —C(=NOH)R$^\beta$; —C(N$_2$)R$^\beta$; —R$^\alpha$—C(=NH)R$^\beta$; —R$^\alpha$—C(=NH)NH$_2$; —R$^\alpha$—C(=NH)NHR$^\beta$; —R$^\alpha$—C(=NH)N(R$^\beta$)$_2$; —R$^\alpha$—C(=NR$^\beta$)R$^\beta$; —R$^\alpha$—C(=NR$^\beta$)NHR$^\beta$; —R$^\alpha$—C(=NR$^\beta$)N(R$^\beta$)$_2$; —R$^\alpha$—C(=NOH)R$^\beta$; —R$^\alpha$—C(N$_2$)R$^\beta$; —NH—CHO; —NR$^\beta$—CHO; —NH—COR$^\beta$; —NR$^\beta$—COR$^\beta$; —CONH$_2$; —CONHR$^\beta$; —CON(R$^\beta$)$_2$; —R$^\alpha$—NH—CHO; —R$^\alpha$—NR$^\beta$—CHO; —R$^\alpha$—NH—COR$^\beta$; —R$^\alpha$—NR$^\beta$—COR$^\beta$; —R$^\alpha$—CONH$_2$; —R$^\alpha$—CONHR$^\beta$; —R$^\alpha$—CON(R$^\beta$)$_2$; —O—R$^\alpha$—OH; —O—R$^\alpha$—OR$^\beta$; —O—R$^\alpha$—NH$_2$; —O—R$^\alpha$—NHR$^\beta$; —O—R$^\alpha$—N(R$^\beta$)$_2$; —O—R$^\alpha$—N(O)(R$^\beta$)$_2$; —O—R$^\alpha$—N$^+$(R$^\beta$)$_3$; —NH—R$^\alpha$—OH; —NH—R$^\alpha$—OR$^\beta$; —NH—R$^\alpha$—NH$_2$; —NH—R$^\alpha$—NHR$^\beta$; —NH—R$^\alpha$—N(R$^\beta$)$_2$; —NH—R$^\alpha$—N(O)(R$^\beta$)$_2$; —NH—R$^\alpha$—N$^+$(R$^\beta$)$_3$; —NR$^\beta$—R$^\alpha$—OH; —NR$^\beta$—R$^\alpha$—OR$^\beta$; —NR$^\beta$—R$^\alpha$—NH$_2$; —NR$^\beta$—R$^\alpha$—NHR$^\beta$; —NR$^\beta$—R$^\alpha$—N(R$^\beta$)$_2$; —NR$^\beta$—R$^\alpha$—N(O)(R$^\beta$)$_2$; —NR$^\beta$—R$^\alpha$—N$^+$(R$^\beta$)$_3$; —N(O)R$^\beta$—R$^\alpha$—OH; —N(O)R$^\beta$—R$^\alpha$—OR$^\beta$; —N(O)R$^\beta$—R$^\alpha$—NH$_2$; —N(O)R$^\beta$—R$^\alpha$—NHR$^\beta$; —N(O)R$^\beta$—R$^\alpha$—N(R$^\beta$)$_2$; —N(O)R$^\beta$—R$^\alpha$—N(O)(R$^\beta$)$_2$; —N(O)R$^\beta$—R$^\alpha$—N$^+$(R$^\beta$)$_3$; —N$^+$(R$^\beta$)$_2$—R$^\alpha$—OH; —N$^+$(R$^\beta$)$_2$—R$^\alpha$—OR$^\beta$; —N$^+$(R$^\beta$)$_2$—R$^\alpha$—NH$_2$; —N$^+$(R$^\beta$)$_2$—R$^\alpha$—NHR$^\beta$; —N$^+$(R$^\beta$)$_2$—R$^\alpha$—N(R$^\beta$)$_2$; or —N$^+$(R$^\beta$)$_2$—R$^\alpha$—N(O)(R$^\beta$)$_2$; and/or (ii) any two hydrogen atoms attached to the same atom may optionally be replaced by a π-bonded substituent independently selected from oxo (=O), =S, =NH or =NR$^\beta$; and/or (iii) any two hydrogen atoms attached to the same or different atoms, within the same optionally substituted group or moiety, may optionally be replaced by a bridging substituent independently selected from —O—, —S—, —NH—, —N=N—, —N(R$^\beta$)—, —N(O)(R$^\beta$)—, —N$^+$(R$^\beta$)$_2$— or —R$^\alpha$—;

wherein each —$R^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, wherein one or more —$CH_2$— groups in the backbone of the alkylene, alkenylene or alkynylene group may optionally be replaced by one or more —N(O)($R^\beta$)— or —$N^+(R^\beta)_2$— groups, and wherein the alkylene, alkenylene or alkynylene group may optionally be substituted with one or more halo and/or —$R^\beta$ groups; and wherein each —$R^\beta$ is independently selected from a $C_1$-$C_6$ alkyl, $C_2$-$C_6$ alkenyl, $C_2$-$C_6$ alkynyl or $C_2$-$C_6$ cyclic group, or wherein any two or three —$R^\beta$ attached to the same nitrogen atom may, together with the nitrogen atom to which they are attached, form a $C_2$-$C_7$ cyclic group, and wherein any —$R^\beta$ may optionally be substituted with one or more $C_1$-$C_4$ alkyl, $C_1$-$C_4$ haloalkyl, $C_3$-$C_7$ cycloalkyl, $C_3$-$C_7$ halocycloalkyl, —O($C_1$-$C_4$ alkyl), —O($C_1$-$C_4$ haloalkyl), —O($C_3$-$C_7$ cycloalkyl), —O($C_3$-$C_7$ halocycloalkyl), —CO($C_1$-$C_4$ alkyl), —CO($C_1$-$C_4$ haloalkyl), —COO($C_1$-$C_4$ alkyl), —COO($C_1$-$C_4$ haloalkyl), halo, —OH, —$NH_2$, —CN, —C≡CH, oxo (=O), or 4- to 6-membered heterocyclic group.

Typically, the compounds of the present invention comprise at most one quaternary ammonium group such as —$N^+(R^\beta)_3$ or —$N^+(R^\beta)_2$—.

Where reference is made to a —$R^\alpha$—C($N_2$)$R^\beta$ group, what is intended is:

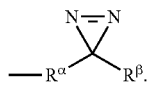

Typically, in an optionally substituted group or moiety:
(i) each hydrogen atom may optionally be replaced by a group independently selected from halo; —CN; —$NO_2$; —$N_3$; —$R^\beta$; —OH; —$OR^\beta$; —$R^\alpha$-halo; —$R^\alpha$—CN; —$R^\alpha$—$NO_2$; —$R^\alpha$—$N_3$; —$R^\alpha$—$R^\beta$; —$R^\alpha$—OH; —$R^\alpha$—$OR^\beta$; —SH; —$SR^\beta$; —$SOR^\beta$; —$SO_2H$; —$SO_2R^\beta$; —$SO_2NH_2$; —$SO_2NHR^\beta$; —$SO_2N(R^\beta)_2$; —$R^\alpha$—SH; —$R^\alpha$—$SR^\beta$; —$R^\alpha$—$SOR^\beta$; —$R^\alpha$—$SO_2H$; —$R^\alpha$—$SO_2R^\beta$; —$R^\alpha$—$SO_2NH_2$; —$R^\alpha$—$SO_2NHR^\beta$; —$R^\alpha$—$SO_2N(R^\beta)_2$; —$NH_2$; —$NHR^\beta$; —$N(R^\beta)_2$; —$R^\alpha$—$NH_2$; —$R^\alpha$—$NHR^\beta$; —$R^\alpha$—$N(R^\beta)_2$; —CHO; —$COR^\beta$; —COOH; —$COOR^\beta$; —$OCOR^\beta$; —$R^\alpha$—CHO; —$R^\alpha$—$COR^\beta$; —$R^\alpha$—COOH; —$R^\alpha$—$COOR^\beta$; —$R^\alpha$—$OCOR^\beta$; —NH—CHO; —$NR^\beta$—CHO; —NH—$COR^\beta$; —$NR^\beta$—$COR^\beta$; —$CONH_2$; —$CONHR^\beta$; —$CON(R^\beta)_2$; —$R^\alpha$—NH—CHO; —$R^\alpha$—$NR^\beta$—CHO; —$R^\alpha$—NH—$COR^\beta$; —$R^\alpha$—$NR^\beta$—$COR^\beta$; —$R^\alpha$—$CONH_2$; —$R^\alpha$—$CONHR^\beta$; —$R^\alpha$—$CON(R^\beta)_2$; —O—$R^\alpha$—OH; —O—$R^\alpha$—OR; —O—$R^\alpha$—$NH_2$; —O—$R^\alpha$—$NHR^\beta$; —O—$R^\alpha$—$N(R^\beta)_2$; —NH—$R^\alpha$—OH; —NH—$R^\alpha$—$OR^\beta$; —NH—$R^\alpha$—$NH_2$; —NH—$R^\alpha$—$NHR^\beta$; —NH—$R^\alpha$—$N(R^\beta)_2$; —$NR^\beta$—$R^\alpha$—OH; —$NR^\beta$—$R^\alpha$—$OR^\beta$; —$NR^\beta$—$R^\alpha$—$NH_2$; —$NR^\beta$—$R^\alpha$—$NHR^\beta$; or —$NR^\beta$—$R^\alpha$—$N(R^\beta)_2$; and/or
(ii) any two hydrogen atoms attached to the same carbon atom may optionally be replaced by a π-bonded substituent independently selected from oxo (=O), =S, =NH or =$NR^\beta$; and/or (iii) any two hydrogen atoms attached to the same or different atoms, within the same optionally substituted group or moiety, may optionally be replaced by a bridging substituent independently selected from —O—, —S—, —NH—, —N($R^\beta$)— or —$R^\alpha$—;
wherein each —$R^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —$R^\beta$ groups; and
wherein each —$R^\beta$ is independently selected from a $C_1$-$C_6$ alkyl, $C_2$-$C_6$ alkenyl, $C_2$-$C_6$ alkynyl or $C_2$-$C_6$ cyclic group, and wherein any —$R^\beta$ may optionally be substituted with one or more $C_1$-$C_4$ alkyl, $C_1$-$C_4$ haloalkyl, $C_3$-$C_7$ cycloalkyl, —O($C_1$-$C_4$ alkyl), —O($C_1$-$C_4$ haloalkyl), —O($C_3$-$C_7$ cycloalkyl), halo, —OH, —$NH_2$, —CN, —C≡CH, oxo (=O), or 4- to 6-membered heterocyclic group.

Alternately in the optionally substituted groups or moieties defined immediately above, each —$R^\beta$ may be independently selected from a $C_1$-$C_6$ alkyl, $C_2$-$C_6$ alkenyl, $C_2$-$C_6$ alkynyl or $C_2$-$C_6$ cyclic group, or any two —$R^\beta$ attached to the same nitrogen atom may, together with the nitrogen atom to which they are attached, form a $C_2$-$C_7$ cyclic group, wherein any —$R^\beta$ may optionally be substituted with one or more $C_1$-$C_4$ alkyl, $C_1$-$C_4$ haloalkyl, $C_3$-$C_7$ cycloalkyl, $C_3$-$C_7$ halocycloalkyl, —O($C_1$-$C_4$ alkyl), —O($C_1$-$C_4$ haloalkyl), —O($C_3$-$C_7$ cycloalkyl), —O($C_3$-$C_7$ halocycloalkyl), halo, —OH, —$NH_2$, —CN, —C≡CH, oxo (=O), or 4- to 6-membered heterocyclic group.

More typically, in an optionally substituted group or moiety:
(i) each hydrogen atom may optionally be replaced by a group independently selected from halo; —CN; —$NO_2$; —$N_3$; —$R^\beta$; —OH; —$OR^\beta$; —$R^\alpha$-halo; —$R^\alpha$—CN; —$R^\alpha$—$NO_2$; —$R^\alpha$—$N_3$; —$R^\alpha$—$R^\beta$; —$R^\alpha$—OH; —$R^\alpha$—$OR^\beta$; —SH; —$SR^\beta$; —$SOR^\beta$; —$SO_2H$; —$SO_2R^\beta$; —$SO_2NH_2$; —$SO_2NHR^\beta$; —$SO_2N(R^\beta)_2$; —$R^\alpha$—SH; —$R^\alpha$—$SR^\beta$; —$R^\alpha$—$SOR^\beta$; —$R^\alpha$—$SO_2H$; —$R^\alpha$—$SO_2R^\beta$; —$R^\alpha$—$SO_2NH_2$; —$R^\alpha$—$SO_2NHR^\beta$; —$R^\alpha$—$SO_2N(R^\beta)_2$; —$NH_2$; —$NHR^\beta$; —$N(R^\beta)_2$; —$R^\alpha$—$NH_2$; —$R^\alpha$—$NHR^\beta$; —$R^\alpha$—$N(R^\beta)_2$; —CHO; —$COR^\beta$; —COOH; —$COOR^\beta$; —$OCOR^\beta$; —$R^\alpha$—CHO; —$R^\alpha$—$COR^\beta$; —$R^\alpha$—COOH; —$R^\alpha$—$COOR^\beta$; or —$R^\alpha$—$OCOR^\beta$; and/or
(ii) any two hydrogen atoms attached to the same carbon atom may optionally be replaced by a π-bonded substituent independently selected from oxo (=O), =S, =NH or =$NR^\beta$; and/or
(iii) any two hydrogen atoms attached to the same or different atoms, within the same optionally substituted group or moiety, may optionally be replaced by a bridging substituent independently selected from —O—, —S—, —NH—, —N($R^\beta$)— or —$R^\alpha$—;
wherein each —$R^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —$R^\beta$ groups; and
  wherein each —$R^\beta$ is independently selected from a $C_1$-$C_6$ alkyl, $C_2$-$C_6$ alkenyl, $C_2$-$C_6$ alkynyl or $C_2$-$C_6$ cyclic group, and wherein any —$R^\beta$ may optionally be substituted with one or more $C_1$-$C_4$ alkyl, $C_1$-$C_4$ haloalkyl, $C_3$-$C_7$ cycloalkyl, —O($C_1$-$C_4$ alkyl), —O($C_1$-$C_4$ haloalkyl), —O($C_3$-$C_7$ cycloalkyl), halo, —OH, —$NH_2$, —CN, —C≡CH, oxo (=O), or 4- to 6-membered heterocyclic group.

Alternately in the optionally substituted groups or moieties defined immediately above, each —$R^\beta$ may be independently selected from a $C_1$-$C_6$ alkyl, $C_2$-$C_6$ alkenyl, $C_2$-$C_6$ alkynyl or $C_2$-$C_6$ cyclic group, or any two —$R^\beta$ attached to the same nitrogen atom may, together with the nitrogen atom to which they are attached, form a $C_2$-$C_7$ cyclic group, wherein any —$R^\beta$ may optionally be substituted with one or more $C_1$-$C_4$ alkyl, $C_1$-$C_4$ haloalkyl, $C_3$-$C_7$ cycloalkyl, $C_3$-$C_7$ halocycloalkyl, —O($C_1$-$C_4$ alkyl), —O($C_1$-$C_4$ haloalkyl), —O($C_3$-$C_7$ cycloalkyl), —O($C_3$-$C_7$ halocycloalkyl), halo, —OH, —$NH_2$, —CN, —C≡CH, oxo (=O), or 4- to 6-membered heterocyclic group.

More typically, in an optionally substituted group or moiety:

(i) each hydrogen atom may optionally be replaced by a group independently selected from halo; —CN; —$NO_2$; —$N_3$; —$R^\beta$; —OH; —$OR^\beta$; —$R^\alpha$-halo; —$R^\alpha$—CN; —$R^\alpha$—$NO_2$; —$R^\alpha$—$N_3$; —$R^\alpha$—$R^\beta$; —$R^\alpha$—OH; —$R^\alpha$—$OR^\beta$; —SH; —$SR^\beta$; —$SOR^\beta$; —$SO_2H$; —$SO_2R^\beta$; —$SO_2NH_2$; —$SO_2NHR^\beta$; —$SO_2N(R^\beta)_2$; —$R^\alpha$—SH; —$R^\alpha$—$SR^\beta$; —$R^\alpha$—$SOR^\beta$; —$R^\alpha$—$SO_2H$; —$R^\alpha$—$SO_2R^\beta$; —$R^\alpha$—$SO_2NH_2$; —$R^\alpha$—$SO_2NHR^\beta$; —$R^\alpha$—$SO_2N(R^\beta)_2$; —$NH_2$; —$NHR^\beta$; —$N(R^\beta)_2$; —$R^\alpha$—$NH_2$; —$R^\alpha$—$NHR^\beta$; —$R^\alpha$—$N(R^\beta)_2$; —CHO; —$COR^\beta$; —COOH; —$COOR^\beta$; —$OCOR^\beta$; —$R^\alpha$—CHO; —$R^\alpha$—$COR^\beta$; —$R^\alpha$—COOH; —$R^\alpha$—$COOR^\beta$; or —$R^\alpha$—$OCOR^\beta$; and/or (ii) any two hydrogen atoms attached to the same carbon atom may optionally be replaced by a π-bonded substituent independently selected from oxo (=O), =S, =NH or =$NR^\beta$; and/or (iii) any two hydrogen atoms attached to the same or different atoms, within the same optionally substituted group or moiety, may optionally be replaced by a bridging substituent independently selected from —O—, —S—, —NH—, —N($R^\beta$)— or —$R^\alpha$—;
  wherein each —$R^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —$R^\beta$ groups; and
  wherein each —$R^\beta$ is independently selected from a $C_1$-$C_6$ alkyl, $C_2$-$C_6$ alkenyl, $C_2$-$C_6$ alkynyl or $C_2$-$C_6$ cyclic group, and wherein any —$R^\beta$ may optionally be substituted with one or more $C_1$-$C_4$ alkyl, halo, —OH, or —O($C_1$-$C_4$ alkyl) groups.

Alternately in the optionally substituted groups or moieties defined immediately above, each —$R^\beta$ may be independently selected from a $C_1$-$C_6$ alkyl, $C_2$-$C_6$ alkenyl, $C_2$-$C_6$ alkynyl or $C_2$-$C_6$ cyclic group, or any two —$R^\beta$ attached to the same nitrogen atom may, together with the nitrogen atom to which they are attached, form a $C_2$-$C_7$ cyclic group, wherein any —$R^\beta$ may optionally be substituted with one or more $C_1$-$C_4$ alkyl, $C_1$-$C_4$ haloalkyl, halo, —OH, or 4- to 6-membered heterocyclic group.

Typically a substituted group comprises 1, 2, 3 or 4 substituents, more typically 1, 2 or 3 substituents, more typically 1 or 2 substituents, and more typically 1 substituent.

Unless stated otherwise, any divalent bridging substituent (e.g. —O—, —S—, —NH—, —N($R^\beta$)—, so —N(O)($R^\beta$)—, —$N^+$($R^\beta$)_2$— or —$R^\alpha$—) of an optionally substituted group or moiety (e.g. $R^1$) must only be attached to the specified group or moiety and may not be attached to a second group or moiety (e.g. $R^2$), even if the second group or moiety can itself be optionally substituted.

The term "halo" includes fluoro, chloro, bromo and iodo.

Unless stated otherwise, where a group is prefixed by the term "halo", such as a haloalkyl or halomethyl group, it is to be understood that the group in question is substituted with one or more halo groups independently selected from fluoro, chloro, bromo and iodo. Typically, the maximum number of halo substituents is limited only by the number of hydrogen atoms available for substitution on the corresponding group without the halo prefix. For example, a halomethyl group may contain one, two or three halo substituents. A haloethyl or halophenyl group may contain one, two, three, four or five halo substituents. Similarly, unless stated otherwise, where a group is prefixed by a specific halo group, it is to be understood that the group in question is substituted with one or more of the specific halo groups. For example, the term "fluoromethyl" refers to a methyl group substituted with one, two or three fluoro groups.

Unless stated otherwise, where a group is said to be "halo-substituted", it is to be understood that the group in question is substituted with one or more halo groups independently selected from fluoro, chloro, bromo and iodo. Typically, the maximum number of halo substituents is limited only by the number of hydrogen atoms available for substitution on the group said to be halo-substituted. For example, a halo-substituted methyl group may contain one, two or three halo substituents. A halo-substituted ethyl or halo-substituted phenyl group may contain one, two, three, four or five halo substituents.

Unless stated otherwise, any reference to an element is to be considered a reference to all isotopes of that element. Thus, for example, unless stated otherwise any reference to hydrogen is considered to encompass all isotopes of hydrogen including deuterium and tritium.

Where reference is made to a hydrocarbyl or other group including one or more heteroatoms N, O or S in its carbon skeleton, or where reference is made to a carbon atom of a hydrocarbyl or other group being replaced by an N, O or S atom, what is intended is that:

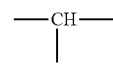

is replaced by

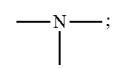

—CH$_2$— is replaced by —NH—, —O— or —S—;
—CH$_3$ is replaced by —NH$_2$, —OH or —SH;
—CH= is replaced by —N=;
CH$_2$= is replaced by NH=, O= or S=; or
CH≡ is replaced by N≡;
provided that the resultant group comprises at least one carbon atom. For example, methoxy, dimethylamino and aminoethyl groups are considered to be hydrocarbyl groups including one or more heteroatoms N, O or S in their carbon skeleton.

Where reference is made to a —CH$_2$— group in the backbone of a hydrocarbyl or other group being replaced by a —N(O)(R$^\beta$)— or —N$^+$(R$^\beta$)$_2$— group, what is intended is that:

—CH$_2$— is replaced by

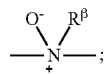

or
—CH$_2$— is replaced by

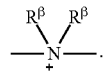

In the context of the present specification, unless otherwise stated, a C$_x$-C$_y$ group is defined as a group containing from x to y carbon atoms. For example, a C$_1$-C$_4$ alkyl group is defined as an alkyl group containing from 1 to 4 carbon atoms. Optional substituents and moieties are not taken into account when calculating the total number of carbon atoms in the parent group substituted with the optional substituents and/or containing the optional moieties. For the avoidance of doubt, replacement heteroatoms, e.g. N, O or S, are not to be counted as carbon atoms when calculating the number of carbon atoms in a C$_x$-C$_y$ group. For example, a morpholinyl group is to be considered a C$_4$ heterocyclic group, not a C$_6$ heterocyclic group.

As will be understood, ring A is a 5-membered heteroaryl group.

In one embodiment, at least one of R$^X$ and R$^Y$ is monovalent.

In a further embodiment, ring A is monocyclic. In such an embodiment, the groups R$^X$, R$^Y$ and, if present, R$^1$ are monovalent, but may be or include cyclic groups. Examples of monocyclic 5-membered heteroaryl groups include furanyl, thiophenyl, pyrrolyl, imidazolyl, pyrazolyl, triazolyl, tetrazolyl, oxazolyl, isoxazolyl, oxadiazolyl, thiazolyl, isothiazolyl and thiadiazolyl groups.

As stated, V, X and Y are each independently selected from C and N, and W and Z are each independently selected from N, O, S, NH and CH, provided that at least one of V, W, X, Y and Z is N, O, S or NH. For the purposes of the present specification, where it is stated that W or Z may be NH or CH, it is to be understood that this refers to W and Z before possible substitution with R$^1$ is considered. Thus, where it is stated that W or Z may be NH, it is to be understood that W or Z may be NH or N—R$^1$ after substitution is considered. Similarly, where it is stated that W or Z may be CH, it is to be understood that W or Z may be CH or C—R$^1$ after substitution is considered.

In one embodiment, at least one of W and Z is O or S. It will be understood that in such an embodiment ring A is a 5-membered heteroaryl group containing at least one oxygen or sulphur atom in the 5-membered ring structure. Examples of such 5-membered heteroaryl groups include furanyl, oxazolyl, thiophenyl and thiazolyl groups. Typically, one of W and Z is O or S and one of W and Z is CH or N. Typically in such an embodiment, V, X and Y are each C. Most typically, W is O or S, V, X and Y are each C, and Z is CH.

In another embodiment, at least one of V, W, X, Y and Z is N or NH. It will be understood that in such an embodiment ring A is a 5-membered heteroaryl group containing at least one nitrogen atom in the 5-membered ring structure. Examples of such 5-membered heteroaryl groups include pyrrolyl, imidazolyl, pyrazolyl, triazolyl, tetrazolyl, oxazolyl, isoxazolyl, oxadiazolyl, thiazolyl, isothiazolyl and thiadiazolyl groups. Typically, one of X and Y is N and one of X and Y is C.

In a further embodiment, V is C, X and Y are each independently selected from C and N, and W and Z are each independently selected from N, O, S, NH and CH, provided that at least one of W, X, Y and Z is N, O, S or NH. Typically, V is C, X and Y are each independently selected from C and N, and W and Z are each independently selected from N, O, S, NH and CH, provided that at least one of W, X, Y and Z is N or NH. More typically in such an embodiment, one of X and Y is N and one of X and Y is C.

In another embodiment, V, X and Y are each independently selected from C and N, and W and Z are each independently selected from N, O, S, NH and CH, provided that at least two of V, W, X, Y and Z are N or NH. Typically in such an embodiment, two of V, W, X, Y and Z are N or NH, and three of V, W, X, Y and Z are C or CH. Typically in such an embodiment, V is C. Typically, one of X and Y is N and one of X and Y is C.

In yet another embodiment, V, X and Y are each independently selected from C and N, and W and Z are each independently selected from N, NH and CH, provided that at least one of V, W, X, Y and Z is N or NH. Typically in such an embodiment, V is C. Typically, at least two of V, W, X, Y and Z are N or NH. More typically, two of V, W, X, Y and Z are N or NH, and three of V, W, X, Y and Z are C or CH. Typically, one of X and Y is N and one of X and Y is C. Most typically, ring A is an imidazolyl or pyrazolyl group. For example, in one embodiment V is C, X is C, Y is N, one of W and Z is CH and one of W and Z is N. In an alternative embodiment, V is C, X is N, Y is C, one of W and Z is CH and one of W and Z is N.

Typically, both R$^X$ and R$^Y$ are monovalent. Typically, any monovalent R$^X$ or R$^Y$ contains from 1 to 12 atoms other than hydrogen. More typically, any monovalent R$^X$ or R$^Y$ contains from 1 to 8 atoms other than hydrogen. Most typically, any monovalent R$^X$ or R$^Y$ contains from 1 to 6 atoms other than hydrogen.

In one embodiment, R$^X$ and R$^Y$ are each independently a halo group or a saturated or unsaturated hydrocarbyl group, wherein the hydrocarbyl group may be straight-chained or branched, or be or include cyclic groups, wherein the hydrocarbyl group may optionally be substituted, and wherein the hydrocarbyl group may optionally include one or more heteroatoms N, O or S in its carbon skeleton. Where the hydrocarbyl group of R$^X$ or R$^Y$ is optionally substituted, typically it is substituted with one or more groups independently selected from halo, —CN, —OH, —NH$_2$, oxo (=O) and =NH.

In a further embodiment, R$^X$ and R$^Y$ are each independently a halo group or a saturated hydrocarbyl group, wherein the saturated hydrocarbyl group may be straight-chained or branched, or be or include cyclic groups, wherein the saturated hydrocarbyl group may optionally be substituted with one or more groups independently selected from halo, —CN, —OH, —NH$_2$ and oxo (=O), and wherein the saturated hydrocarbyl group may optionally include one or two heteroatoms independently selected from N and O in its carbon skeleton.

In another embodiment, $R^X$ and $R^Y$ are each independently a halo group or a saturated hydrocarbyl group, wherein the saturated hydrocarbyl group may be straight-chained or branched, or be or include cyclic groups, wherein the saturated hydrocarbyl group may optionally be substituted with one or more groups independently selected from halo, —CN and —OH.

Typically, where $R^X$ or $R^Y$ is a hydrocarbyl group, the hydrocarbyl group contains from 1 to 8 carbon atoms. More typically, the hydrocarbyl group contains from 1 to 6 carbon atoms. Most typically, the hydrocarbyl group contains from 1 to 4 carbon atoms.

In one embodiment, $R^X$ is selected from a halo, $C_1$-$C_6$ alkyl, $C_1$-$C_6$ haloalkyl $C_3$-$C_6$ cycloalkyl or $C_3$-$C_6$ halocycloalkyl group. More typically, $R^X$ is selected from a fluoro, chloro, $C_1$-$C_3$ alkyl or cyclopropyl group, wherein the $C_1$-$C_3$ alkyl or cyclopropyl group may optionally be substituted with one or more fluoro and/or chloro groups. More typically still, $R^X$ is selected from a chloro, methyl, ethyl, isopropyl or cyclopropyl group.

Typically, where one of $R^X$ and $R^Y$ is a halo group, the other of $R^X$ and $R^Y$ is not a halo group.

In one embodiment, $R^Y$ is not a halo group.

In one embodiment, $R^Y$ is selected from a $C_1$-$C_6$ alkyl or a $C_3$-$C_6$ cycloalkyl group, wherein the $C_1$-$C_6$ alkyl or $C_3$-$C_6$ cycloalkyl group may optionally be substituted with one or more substituents independently selected from halo, —CN and —OH. More typically, $R^Y$ is selected from a $C_1$-$C_4$ alkyl or a $C_3$-$C_6$ cycloalkyl group, wherein the $C_1$-$C_4$ alkyl or $C_3$-$C_6$ cycloalkyl group is substituted with one or two —OH groups. More typically still, $R^Y$ is selected from a branched $C_3$-$C_4$ alkyl group, wherein the branched $C_3$-$C_4$ alkyl group is substituted with a single —OH group.

In one embodiment, neither of $R^X$ and $R^Y$ are halo groups. Typically in such an embodiment, $R^X$ is selected from $C_1$-$C_6$ alkyl, $C_1$-$C_6$ haloalkyl, $C_3$-$C_6$ cycloalkyl or $C_3$-$C_6$ halocycloalkyl group, and $R^Y$ is selected from a $C_1$-$C_6$ alkyl or a $C_3$-$C_6$ cycloalkyl group, wherein the $C_1$-$C_6$ alkyl or $C_3$-$C_6$ cycloalkyl group of $R^Y$ may optionally be substituted with one or more substituents independently selected from halo, —CN and —OH. More typically, $R^X$ is selected from a $C_1$-$C_3$ alkyl or cyclopropyl group, wherein the $C_1$-$C_3$ alkyl or cyclopropyl group may optionally be substituted with one or more fluoro and/or chloro groups, and $R^Y$ is selected from a $C_1$-$C_4$ alkyl or $C_3$-$C_6$ cycloalkyl group, wherein the $C_1$-$C_4$ alkyl or $C_3$-$C_6$ cycloalkyl group is substituted with one or two —OH groups.

More typically, $R^X$ is selected from a methyl, ethyl, isopropyl or cyclopropyl group, and $R^Y$ is selected from a branched $C_3$-$C_4$ alkyl group, wherein the branched $C_3$-$C_4$ alkyl group is substituted with a single —OH group.

In an alternative embodiment, $R^X$ and $R^Y$ together with the atoms X and Y to which they are attached may form a 4- to 12-membered saturated or unsaturated cyclic group fused to ring A, wherein the cyclic group fused to ring A may optionally be substituted. Typically in such an embodiment, $R^X$ and $R^Y$ together with the atoms X and Y to which they are attached form a 5- or 6-membered saturated or unsaturated cyclic group, wherein the cyclic group may optionally be substituted.

In one embodiment, for example where $R^X$ and $R^Y$ together with the atoms X and Y to which they are attached form a saturated or unsaturated cyclic group as discussed above, $R^X$ and $R^Y$ together form a divalent group —$R^{XY}$—, wherein —$R^{XY}$— is directly attached to the ring atoms X and Y.

For the purposes of the present specification, where it is stated that a first atom or group is "directly attached" to a second atom or group it is to be understood that the first atom or group is covalently bonded to the second atom or group with no intervening atom(s) or groups being present. So, for example, for the group —(C=O)N(CH$_3$)$_2$, the carbon atom of each methyl group is directly attached to the nitrogen atom and the carbon atom of the carbonyl group is directly attached to the nitrogen atom, but the carbon atom of the carbonyl group is not directly attached to the carbon atom of either methyl group.

Typically, —$R^{XY}$— contains from 1 to 12 atoms other than hydrogen or halogen. More typically, —$R^{XY}$— contains from 3 to 10 atoms other than hydrogen or halogen. Most typically, —$R^{XY}$— contains from 4 to 8 atoms other than hydrogen or halogen.

In one embodiment, —$R^{XY}$— is a saturated or unsaturated hydrocarbylene group, wherein the hydrocarbylene group may be straight-chained or branched, or be or include cyclic groups, wherein the hydrocarbylene group may optionally be substituted, and wherein the hydrocarbylene group may optionally include one or more heteroatoms N, O or S in its carbon skeleton. Where the hydrocarbylene group of —$R^{XY}$— is optionally substituted, typically it is substituted with one or more groups independently selected from halo, —CN, —OH, —NH$_2$, oxo (=O) and =NH.

More typically, —$R^{XY}$— is a saturated hydrocarbylene group, wherein the saturated hydrocarbylene group is straight-chained or branched, wherein the saturated hydrocarbylene group may optionally be substituted with one or more groups independently selected from halo, —CN, —OH, —NH$_2$ and oxo (=O), and wherein the saturated hydrocarbylene group may optionally include one or two heteroatoms N or O in its carbon skeleton.

Typically, the group —$R^{XY}$—, including any optional substituents, comprises at least one oxygen or nitrogen atom. More typically, the group —$R^{XY}$—, including any optional substituents, comprises at least one oxygen atom.

In one embodiment, $R^X$ and $R^Y$ contain only atoms selected from the group consisting of carbon, hydrogen, nitrogen, oxygen and halogen atoms. In a further embodiment, $R^X$ and $R^Y$ contain only atoms selected from the group consisting of carbon, hydrogen, oxygen and halogen atoms.

As stated above, m is 0, 1 or 2. More typically, m is 0 or 1. Most typically, m is 0, i.e. the compound has the formula (Ia):

Formula (Ia)

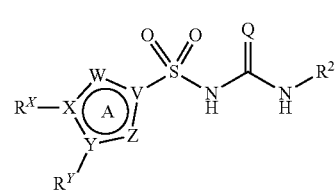

wherein Q, V, W, X, Y, Z, $R^2$, $R^X$ and $R^Y$ are as defined herein.

As will be understood, each $R^1$ where present may be directly attached to either ring atom W or Z.

Typically, each $R^1$ where present is monovalent.

In any of the above embodiments, any monovalent $R^1$ may be independently selected from halo; —CN; —NO$_2$; —N$_3$; —R$^\beta$; —OH; —OR$^\beta$; —R$^\alpha$-halo; —R$^\alpha$—CN; —R$^\alpha$—NO$_2$; —R$^\alpha$—N$_3$; —R$^\alpha$—R$^\beta$; —R$^\alpha$—OH; —R$^\alpha$—OR$^\beta$; —SH; —SR$^\beta$; —SOR$^\beta$; —SO$_2$H; —SO$_2$R$^\beta$; —SO$_2$NH$_2$; —SO$_2$NHR$^\beta$; —SO$_2$N(R$^\beta$)$_2$; —R$^\alpha$—SH; —R$^\alpha$—SR$^\beta$; —R$^\alpha$—SOR$^\beta$; —R$^\alpha$—SO$_2$H; —R$^\alpha$—SO$_2$R$^\beta$; —R$^\alpha$—SO$_2$NH$_2$; —R$^\alpha$—SO$_2$NHR$^\beta$; —R$^\alpha$—SO$_2$N(R$^\beta$)$_2$; —Si(R$^\beta$)$_3$; —O—Si(R$^\beta$)$_3$; —R$^\alpha$—Si(R$^\beta$)$_3$; —R$^\alpha$—O—Si(R$^\beta$)$_3$; —NH$_2$; —NHR$^\beta$; —N(R$^\beta$)$_2$; —N(O)(R$^\beta$)$_2$; —N$^+$(R$^\beta$)$_3$; —R$^\alpha$—NH$_2$; —R$^\alpha$—NHR$^\beta$; —R$^\alpha$—N(R$^\beta$)$_2$; —R$^\alpha$—N(O)(R$^\beta$)$_2$; —R$^\alpha$—N$^+$(R$^\beta$)$_3$; —CHO; —COR$^\beta$; —COOH; —COOR$^\beta$; —OCOR$^\beta$; —R$^\alpha$—CHO; —R$^\alpha$—COR$^\beta$; —R$^\alpha$—COOH; —R$^\alpha$—COOR$^\beta$; —R$^\alpha$—OCOR$^\beta$; —C(=NH)R$^\beta$; —C(=NH)NH$_2$; —C(=NH)NHR$^\beta$; —C(=NH)N(R$^\beta$)$_2$; —C(=NR$^\beta$)R$^\beta$; —C(=NR$^\beta$)NHR$^\beta$; —C(=NR$^\beta$)N(R$^\beta$)$_2$; —C(=NOH)R$^\beta$; —C(N$_2$)R$^\beta$; —R$^\alpha$—C(=NH)R$^\beta$; —R$^\alpha$—C(=NH)NH$_2$; —R$^\alpha$—C(=NH)NHR$^\beta$; —R$^\alpha$—C(=NH)N(R$^\beta$)$_2$; —R$^\alpha$—C(=NR$^\beta$)R$^\beta$; —R$^\alpha$—C(=NR$^\beta$)NHR$^\beta$; —R$^\alpha$—C(=NR$^\beta$)N(R$^\beta$)$_2$; —R$^\alpha$—C(=NOH)R$^\beta$; —R$^\alpha$—C(N$_2$)R$^\beta$; —NH—CHO; —NR$^\beta$—CHO; —NH—COR$^\beta$; —NR$^\beta$—COR$^\beta$; —CONH$_2$; —CONHR$^\beta$; —CON(R$^\beta$)$_2$; —R$^\alpha$—NH—CHO; —R$^\alpha$—NR$^\beta$—CHO; —R$^\alpha$—NH—COR$^\beta$; —R$^\alpha$—NR$^\beta$—COR$^\beta$; —R$^\alpha$—CONH$_2$; —R$^\alpha$—CONHR$^\beta$; —R$^\alpha$—CON(R$^\beta$)$_2$; —O—R$^\alpha$—OH; —O—R$^\alpha$—OR$^\beta$; —O—R$^\alpha$—NH$_2$; —O—R$^\alpha$—NHR$^\beta$; —O—R$^\alpha$—N(R$^\beta$)$_2$; —O—R$^\alpha$—N(O)(R$^\beta$)$_2$; —O—R$^\alpha$—N$^+$(R$^\beta$)$_3$; —NH—R$^\alpha$—OH; —NH—R$^\alpha$—OR$^\beta$; —NH—R$^\alpha$—NH$_2$; —NH—R$^\alpha$—NHR$^\beta$; —NH—R$^\alpha$—N(R$^\beta$)$_2$; —NH—R$^\alpha$—N(O)(R$^\beta$)$_2$; —NH—R$^\alpha$—N$^+$(R$^\beta$)$_3$; —NR$^\beta$—R$^\alpha$—OH; —NR$^\beta$—R$^\alpha$—OR$^\beta$; —NR$^\beta$—R$^\alpha$—NH$_2$; —NR$^\beta$—R$^\alpha$—NHR$^\beta$; —NR$^\beta$—R$^\alpha$—N(R$^\beta$)$_2$; —NR$^\beta$—R$^\alpha$—N(O)(R$^\beta$)$_2$; —NR$^\beta$—R$^\alpha$—N$^+$(R$^\beta$)$_3$; —N(O)R$^\beta$—R$^\alpha$—OH; —N(O)R$^\beta$—R$^\alpha$—OR$^\beta$; —N(O)R$^\beta$—R$^\alpha$—NH$_2$; —N(O)R$^\beta$—R$^\alpha$—NHR$^\beta$; —N(O)R$^\beta$—R$^\alpha$—N(R$^\beta$)$_2$; —N(O)R$^\beta$—R$^\alpha$—N(O)(R$^\beta$)$_2$; —N(O)R$^\beta$—R$^\alpha$—N$^+$(R$^\beta$)$_3$; —N$^+$(R$^\beta$)$_2$—R$^\alpha$—OH; —N$^+$(R$^\beta$)$_2$—R$^\alpha$—OR$^\beta$; —N$^+$(R$^\beta$)$_2$—R$^\alpha$—NH$_2$; —N$^+$(R$^\beta$)$_2$—R$^\alpha$—NHR$^\beta$; —N$^+$(R$^\beta$)$_2$—R$^\alpha$—N(R$^\beta$)$_2$; or —N$^+$(R$^\beta$)$_2$—R$^\alpha$—N(O)(R$^\beta$)$_2$;

wherein each —R$^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, wherein one or more —CH$_2$— groups in the backbone of the alkylene, alkenylene or alkynylene group may optionally be replaced by one or more —N(O)(R$^\beta$)— or —N$^+$(R$^\beta$)$_2$— groups, and wherein the alkylene, alkenylene or alkynylene group may optionally be substituted with one or more halo and/or —R$^\beta$ groups; and wherein each —R$^\beta$ is independently selected from a C$_1$-C$_6$ alkyl, C$_2$-C$_6$ alkenyl, C$_2$-C$_6$ alkynyl or C$_2$-C$_6$ cyclic group, or wherein any two or three —R$^\beta$ attached to the same nitrogen atom may, together with the nitrogen atom to which they are attached, form a C$_2$-C$_7$ cyclic group, and wherein any —R$^\beta$ may optionally be substituted with one or more C$_1$-C$_4$ alkyl, C$_1$-C$_4$ haloalkyl, C$_3$-C$_7$ cycloalkyl, C$_3$-C$_7$ halocycloalkyl, —O(C$_1$-C$_4$ alkyl), —O(C$_1$-C$_4$ haloalkyl), —O(C$_3$-C$_7$ cycloalkyl), —O(C$_3$-C$_7$ halocycloalkyl), —CO(C$_1$-C$_4$ alkyl), —CO(C$_1$-C$_4$ haloalkyl), —COO(C$_1$-C$_4$ alkyl), —COO(C$_1$-C$_4$ haloalkyl), halo, —OH, —NH$_2$, —CN, —C≡CH, oxo (=O), or 4- to 6-membered heterocyclic group.

In one embodiment, each $R^1$ is independently selected from halo; —CN; —NO$_2$; —N$_3$; —R$^\beta$; —OH; —OR$^\beta$; —R$^\alpha$-halo; —R$^\alpha$—CN; —R$^\alpha$—NO$_2$; —R$^\alpha$—N$_3$; —R$^\alpha$—R$^\beta$; —R$^\alpha$—OH; —R$^\alpha$—OR$^\beta$; —SH; —SR$^\beta$; —SOR$^\beta$; —SO$_2$H; —SO$_2$R$^\beta$; —SO$_2$NH$_2$; —SO$_2$NHR$^\beta$; —SO$_2$N(R$^\beta$)$_2$; —R$^\alpha$—SH; —R$^\alpha$—SR$^\beta$; —R$^\alpha$—SOR$^\beta$; —R$^\alpha$—SO$_2$H; —R$^\alpha$—SO$_2$R$^\beta$; —R$^\alpha$—SO$_2$NH$_2$; —R$^\alpha$—SO$_2$NHR$^\beta$; —R$^\alpha$—SO$_2$N(R$^\beta$)$_2$; —NH$_2$; —NHR$^\beta$; —N(R$^\beta$)$_2$; —R$^\alpha$—NH$_2$; —R$^\alpha$—NHR$^\beta$; —R$^\alpha$—N(R$^\beta$)$_2$; —CHO; —COR$^\beta$; —COOH; —COOR$^\beta$; —OCOR$^\beta$; —R$^\alpha$—CHO; —R$^\alpha$—COR$^\beta$; —R$^\alpha$—COOH; —R$^\alpha$—COOR$^\beta$; —R$^\alpha$—OCOR$^\beta$; —NH—CHO; —NR$^\beta$—CHO; —NH—COR$^\beta$; —NR$^\beta$—COR$^\beta$; —CONH$_2$; —CONHR$^\beta$; —CON(R$^\beta$)$_2$; —R$^\alpha$—NH—CHO; —R$^\alpha$—NR$^\beta$—CHO; —R$^\alpha$—NH—COR$^\beta$; —R$^\alpha$—NR$^\beta$—COR$^\beta$; —R$^\alpha$—CONH$_2$; —R$^\alpha$—CONHR$^\beta$; —R$^\alpha$—CON(R$^\beta$)$_2$; —O—R$^\alpha$—OH; —O—R$^\alpha$—OR$^\beta$; —O—R$^\alpha$—NH$_2$; —O—R$^\alpha$—NHR$^\beta$; —O—R$^\alpha$—N(R$^\beta$)$_2$; —NH—R$^\alpha$—OH; —NH—R$^\alpha$—OR$^\beta$; —NH—R$^\alpha$—NH$_2$; —NH—R$^\alpha$—NHR$^\beta$; —NH—R$^\alpha$—N(R$^\beta$)$_2$; —NR$^\beta$—R$^\alpha$—OH; —NR$^\beta$—R$^\alpha$—OR$^\beta$; —NR$^\beta$—R$^\alpha$—NH$_2$; —NR$^\beta$—R$^\alpha$—NHR$^\beta$; or —NR$^\beta$—R$^\alpha$—N(R$^\beta$)$_2$;

wherein each —R$^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —R$^\beta$ groups; and wherein each —R$^\beta$ is independently selected from a C$_1$-C$_6$ alkyl, C$_2$-C$_6$ alkenyl, C$_2$-C$_6$ alkynyl or C$_2$-C$_6$ cyclic group, and wherein any —R$^\beta$ may optionally be substituted with one or more C$_1$-C$_4$ alkyl, C$_1$-C$_4$ haloalkyl, C$_3$-C$_7$ cycloalkyl, —O(C$_1$-C$_4$ alkyl), —O(C$_1$-C$_4$ haloalkyl), —O(C$_3$-C$_7$ cycloalkyl), halo, —OH, —NH$_2$, —CN, —C≡CH, oxo (=O), or 4- to 6-membered heterocyclic group.

In another embodiment, each $R^1$ is independently selected from halo; —CN; —NO$_2$; —N$_3$; —R$^\beta$; —OH; —OR$^\beta$; —R$^\alpha$-halo; —R$^\alpha$—CN; —R$^\alpha$—NO$_2$; —R$^\alpha$—N$_3$; —R$^\alpha$—R$^\beta$; —R$^\alpha$—OH; —R$^\alpha$—OR$^\beta$; —SH; —SR$^\beta$; —SOR$^\beta$; —SO$_2$H; —SO$_2$R$^\beta$; —SO$_2$NH$_2$; —SO$_2$NHR$^\beta$; —SO$_2$N(R$^\beta$)$_2$; —R$^\alpha$—SH; —R$^\alpha$—SR$^\beta$; —R$^\alpha$—SOR$^\beta$; —R$^\alpha$—SO$_2$H; —R$^\alpha$—SO$_2$R$^\beta$; —R$^\alpha$—SO$_2$NH$_2$; —R$^\alpha$—SO$_2$NHR$^\beta$; —R$^\alpha$—SO$_2$N(R$^\beta$)$_2$; —NH$_2$; —NHR$^\beta$; —N(R$^\beta$)$_2$; —R$^\alpha$—NH$_2$; —R$^\alpha$—NHR$^\beta$; —R$^\alpha$—N(R$^\beta$)$_2$; —CHO; —COR$^\beta$; —COOH; —COOR$^\beta$; —OCOR$^\beta$; —R$^\alpha$—CHO; —R$^\alpha$—COR$^\beta$; —R$^\alpha$—COOH; —R$^\alpha$—COOR$^\beta$; or —R$^\alpha$—OCOR$^\beta$;

wherein each —R$^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —R$^\beta$ groups; and wherein each —R$^\beta$ is independently selected from a C$_1$-C$_6$ alkyl, C$_2$-C$_6$ alkenyl, C$_2$-C$_6$ alkynyl or C$_2$-C$_6$ cyclic group, and wherein any —$R^\beta$ may optionally be substituted with one or more $C_1$-$C_4$ alkyl, $C_1$-$C_4$ haloalkyl, $C_3$-$C_7$ cycloalkyl, —O($C_1$-$C_4$ alkyl), —O($C_1$-$C_4$ haloalkyl), —O($C_3$-$C_7$ cycloalkyl), halo, —OH, —$NH_2$, —CN, —C≡CH, oxo (═O), or 4- to 6-membered heterocyclic group.

Alternatively, each $R^1$ may be independently selected from halo; —CN; —$NO_2$; —$N_3$; —$R^\beta$; —OH; —$OR^\beta$; —$R^\alpha$-halo; —$R^\alpha$—CN; —$R^\alpha$—$NO_2$; —$R^\alpha$—$N_3$; —$R^\alpha$—$R^\beta$; —$R^\alpha$—OH; —$R^\alpha$—$OR^\beta$; —SH; —$SR^\beta$; —$SOR^\beta$; —$SO_2H$; —$SO_2R^\beta$; —$SO_2NH_2$; —$SO_2NHR^\beta$; —$SO_2N(R^\beta)_2$; —$R^\alpha$—SH; —$R^\alpha$—$SR^\beta$; —$R^\alpha$—$SOR^\beta$; —$R^\alpha$—$SO_2H$; —$R^\alpha$—$SO_2R^\beta$; —$R^\alpha$—$SO_2NH_2$; —$R^\alpha$—$SO_2NHR^\beta$; —$R^\alpha$—$SO_2N(R^\beta)_2$; —$NH_2$; —$NHR^\beta$; —$N(R^\beta)_2$; —$R^\alpha$—$NH_2$; —$R^\alpha$—$NHR^\beta$; —$R^\alpha$—$N(R^\beta)_2$; —CHO; —$COR^\beta$; —COOH; —$COOR^\beta$; —$OCOR^\beta$; —$R^\alpha$—CHO; —$R^\alpha$—$COR^\beta$; —$R^\alpha$—COOH; —$R^\alpha$—$COOR^\beta$; or —$R^\alpha$—$OCOR^\beta$;

wherein each —$R^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —$R^\beta$ groups; and wherein each —$R^\beta$ is independently selected from a $C_1$-$C_6$ alkyl, $C_2$-$C_6$ alkenyl, $C_2$-$C_6$ alkynyl or $C_2$-$C_6$ cyclic group, and wherein any —$R^\beta$ may optionally be substituted with one or more $C_1$-$C_4$ alkyl, halo, —OH, or —O($C_1$-$C_4$ alkyl) groups.

Typically, each $R^1$ where present is a halo group or contains from 1 to 6 atoms other than hydrogen or halogen. Typically, where any $R^1$ contains from 1 to 6 atoms other than hydrogen or halogen, the $R^1$ is a saturated hydrocarbyl group, wherein the saturated hydrocarbyl group may be straight-chained or branched, or be or include cyclic groups, wherein the saturated hydrocarbyl group may optionally be substituted with one or more groups independently selected from halo, —CN, —OH, —$NH_2$ and oxo (═O), and wherein the saturated hydrocarbyl group may optionally include one or two heteroatoms N or O in its carbon skeleton.

More typically, each $R^1$ where present is independently selected from a fluoro, chloro, $C_1$-$C_4$ alkyl or $C_3$-$C_4$ cycloalkyl group, wherein any $C_1$-$C_4$ alkyl or $C_3$-$C_4$ cycloalkyl group may optionally be substituted with one or more fluoro and/or chloro groups.

In one embodiment, the group:

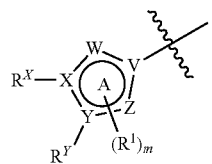

including any optional substituents, contains from 7 to 25 atoms other than hydrogen. More typically, the group contains from 8 to 17 atoms other than hydrogen. Most typically, the group contains from 9 to 13 atoms other than hydrogen.

In one embodiment of the first aspect of the invention, $R^2$ has the formula:

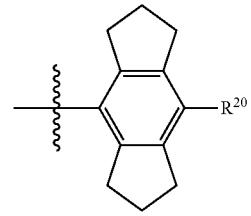

wherein $R^{20}$ is a halo, —OH, —$NO_2$, —$NH_2$, —$N_3$, —SH, —$SO_2H$, —$SO_2NH_2$, or a saturated or unsaturated hydrocarbyl group, wherein the hydrocarbyl group may be straight-chained or branched, or be or include cyclic groups, wherein the hydrocarbyl group may optionally be substituted, and wherein the hydrocarbyl group may optionally include one or more heteroatoms N, O or S in its carbon skeleton.

Typically, $R^{20}$ contains from 1 to 8 atoms other than hydrogen. More typically, $R^{20}$ contains from 1 to 6 atoms other than hydrogen. Most typically, $R^{20}$ contains from 1 to 4 atoms other than hydrogen.

In one embodiment, $R^{20}$ is a halo, —$NO_2$, —CN, or a saturated hydrocarbyl group, wherein the saturated hydrocarbyl group may be straight-chained or branched, wherein the saturated hydrocarbyl group may optionally be substituted with one or more groups independently selected from halo, —CN, —OH, —$NH_2$ and oxo (═O), and wherein the saturated hydrocarbyl group may optionally include one or two heteroatoms N or O in its carbon skeleton.

In a further embodiment, $R^{20}$ is a halo, —$NO_2$, —CN, —CHO, —$COR^{21}$, —COOH, —$COOR^{21}$, —$CONH_2$, —$CONHR^{21}$ or —$CON(R^{21})_2$ group, wherein each —$R^{21}$ is independently selected from a $C_1$-$C_6$ alkyl, $C_3$-$C_6$ cycloalkyl, phenyl, benzyl, —$R^{22}$ or —$CH_2R^{22}$ group, wherein $R^{22}$ is a 5- or 6-membered heteroaryl group, and wherein any —$R^{21}$ may optionally be substituted with one or more halo groups, or wherein any two —$R^{21}$ together with the nitrogen atom to which they are attached may form a 3- to 6-membered heterocyclic group, wherein the 3- to 6-membered heterocyclic group may optionally be substituted with one or more halo groups.

More typically, $R^{20}$ is a halo, —$NO_2$, —CN, —$COOR^{21}$, —$CONH_2$, —$CONHR^{21}$ or —$CON(R^{21})_2$ group, wherein each —$R^{21}$ is independently selected from a $C_1$-$C_4$ alkyl group, and wherein any —$R^{21}$ may optionally be substituted with one or more halo groups. More typically still, $R^{20}$ is a fluoro, chloro, bromo or —CN group. Most typically, $R^{20}$ is a bromo or —CN group.

In another embodiment of the first aspect of the invention, $R^2$ is a heteroaryl group substituted at the $\alpha$ and $\alpha'$ positions, wherein $R^2$ may optionally be further substituted. For the avoidance of doubt, it is noted that it is a ring atom of the heteroaryl group of $R^2$ that is directly attached to the nitrogen atom of the urea or thiourea group, not any substituent.

Typically, $R^2$ is a 5- or 6-membered heteroaryl group, wherein the heteroaryl group is substituted at the $\alpha$ and $\alpha'$ positions, and wherein $R^2$ may optionally be further substituted. Most typically, $R^2$ is a 6-membered heteroaryl group, wherein the heteroaryl group is substituted at the $\alpha$ and $\alpha'$ positions, and wherein $R^2$ may optionally be further substituted.

In one embodiment, the parent 5- or 6-membered heteroaryl group of $R^2$ may be selected from pyridinyl, pyridazinyl, pyrimidinyl, pyrrolyl, furanyl, thiophenyl, pyrazolyl, imidazolyl, isoxazolyl, isothiazolyl or triazolyl. Typically, the parent 5- or 6-membered heteroaryl group of $R^2$ may be selected from pyridinyl, pyridazinyl, pyrimidinyl, pyrrolyl, pyrazolyl, imidazolyl or triazolyl. Typically, the parent 5- or 6-membered heteroaryl group of $R^2$ may be selected from pyridinyl, pyridazinyl, pyrimidinyl or pyrazolyl.

As used herein, the nomenclature α, β, α', β' refers to the position of the atoms of a cyclic group, such as —$R^2$, relative to the point of attachment of the cyclic group to the remainder of the molecule. For example, where —$R^2$ is a 1,2,3,5,6,7-hexahydro-s-indacen-4-yl moiety, the α, β, α' and β' positions are as follows:

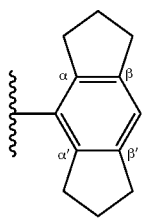 [SMILES: *c1c2c(cc3c1CCC3)CCC2]

As used herein, when assigning the nomenclature α, α', etc. to heteroaryl groups, no weight is given to the position of any ring heteroatoms. For example both of the following groups are to be considered to be α-substituted:

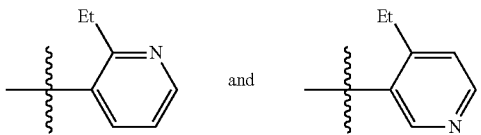 [SMILES: *c1cccnc1CC ; *c1cnccc1CC]

For the avoidance of doubt, where it is stated that a cyclic group, such as a heteroaryl group, is substituted at the α and/or α' positions, it is to be understood that one or more hydrogen atoms at the α and/or α' positions respectively are replaced by one or more substituents, such as any optional substituent as defined above. Unless stated otherwise, the term "substituted" does not include the replacement of one or more ring carbon atoms by one or more ring heteroatoms.

In any of the above embodiments, typical substituents at the α and/or α' positions of the parent heteroaryl group of $R^2$ comprise a carbon atom. For example, typical substituents at the α and/or α' positions may be independently selected from —$R^3$, —$OR^3$ and —$COR^3$ groups, wherein each $R^3$ is independently selected from a $C_1$-$C_6$ alkyl, $C_2$-$C_6$ alkenyl, $C_2$-$C_6$ alkynyl or $C_2$-$C_6$ cyclic group and wherein each $R^3$ is optionally further substituted with one or more halo groups. More typically, the substituents at the α and α' positions are independently selected from alkyl and cycloalkyl groups, such as $C_3$-$C_6$ branched alkyl and $C_3$-$C_6$ cycloalkyl groups, e.g. isopropyl, cyclopropyl, cyclohexyl or t-butyl groups, wherein the alkyl and cycloalkyl groups are optionally further substituted with one or more fluoro and/or chloro groups.

In one aspect of any of the above embodiments, each substituent at the α and α' positions comprises a carbon atom.

Other typical substituents at the α and/or α' positions of the parent heteroaryl group of $R^2$ may include cycloalkyl, cycloalkenyl, non-aromatic heterocyclic, aryl or heteroaryl rings which are fused to the parent heteroaryl group across the α,β and/or α',β' positions respectively. Such fused cyclic groups are described in greater detail below.

In one embodiment, $R^2$ is a fused heteroaryl group, wherein a cycloalkyl, cycloalkenyl, non-aromatic heterocyclic, aryl or heteroaryl ring is fused to the heteroaryl group across the α,β positions, wherein the heteroaryl group is also substituted at the α' position (for example with a substituent selected from —$R^3$, —$OR^3$ and —$COR^3$, wherein each $R^3$ is independently selected from a $C_1$-$C_6$ alkyl, $C_2$-$C_6$ alkenyl, $C_2$-$C_6$ alkynyl or $C_2$-$C_6$ cyclic group and wherein each $R^3$ is optionally further substituted with one or more halo groups), and wherein $R^2$ may optionally be further substituted. Typically in such an embodiment, $R^2$ is bicyclic or tricyclic.

More typically, $R^2$ is a fused 5- or 6-membered heteroaryl group, wherein the 5- or 6-membered heteroaryl group is fused to one or more cycloalkyl, cycloalkenyl, non-aromatic heterocyclic, aryl or heteroaryl rings, wherein $R^2$ may optionally be further substituted. Typically, a cycloalkyl, cycloalkenyl, non-aromatic heterocyclic, aryl or heteroaryl ring is fused to the 5- or 6-membered heteroaryl group across the α,β positions so as to form a 4- to 6-membered fused ring structure. Typically, the 5- or 6-membered heteroaryl group is also substituted at the α' position (for example with a substituent selected from —$R^3$, —$OR^3$ and —$COR^3$, wherein each $R^3$ is independently selected from a $C_1$-$C_6$ alkyl, $C_2$-$C_6$ alkenyl, $C_2$-$C_6$ alkynyl or $C_2$-$C_6$ cyclic group and wherein each $R^3$ is optionally further substituted with one or more halo groups). Typically in such an embodiment, $R^2$ is bicyclic or tricyclic.

In another embodiment, $R^2$ is a fused heteroaryl group, wherein a first cycloalkyl, cycloalkenyl, non-aromatic heterocyclic, aryl or heteroaryl ring is fused to the heteroaryl group across the α,β positions and a second cycloalkyl, cycloalkenyl, non-aromatic heterocyclic, aryl or heteroaryl ring is fused to the heteroaryl group across the α',β' positions, wherein $R^2$ may optionally be further substituted. Typically in such an embodiment, $R^2$ is tricyclic.

More typically, $R^2$ is a fused 5- or 6-membered heteroaryl group, wherein a first cycloalkyl, cycloalkenyl, non-aromatic heterocyclic, aryl or heteroaryl ring is fused to the 5- or 6-membered heteroaryl group across the α,β positions so as to form a first 4- to 6-membered fused ring structure, and a second cycloalkyl, cycloalkenyl, non-aromatic heterocyclic, aryl or heteroaryl ring is fused to the 5- or 6-membered heteroaryl group across the α',β' positions so as to form a second 4- to 6-membered fused ring structure, wherein $R^2$ may optionally be further substituted. Typically in such an embodiment, $R^2$ is tricyclic.

In one embodiment, —$R^2$ has a formula selected from:

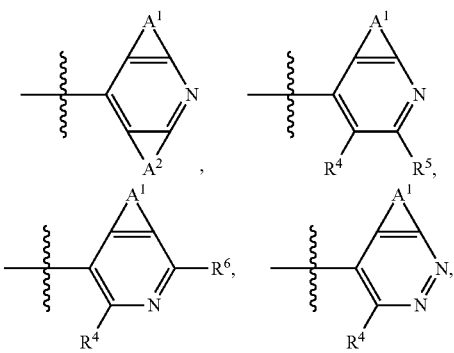

-continued

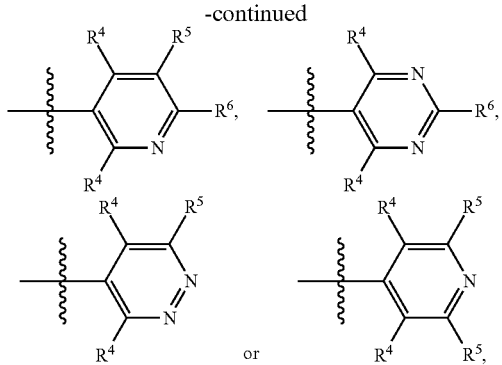

wherein:
$A^1$ and $A^2$ are each independently selected from an optionally substituted alkylene or alkenylene group, wherein one or more carbon atoms in the backbone of the alkylene or alkenylene group may optionally be replaced by one or more heteroatoms N, O or S;
each $R^4$ is independently selected from a $-R^{41}$, $-OR^{41}$ or $-COR^{41}$ group;
each $R^5$ is independently selected from hydrogen or a halo, $-R^{41}$, $-OR^{41}$ or $-COR^{41}$ group;
each $R^6$ is independently selected from hydrogen or a halo, $-NO_2$, $-CN$, $-CHO$, $-COR^{61}$, $-COOH$, $-COOR^{61}$, $-CONH_2$, $-CONHR^{61}$ or $-CON(R^{61})_2$ group;
each $R^{41}$ is independently selected from a $C_1$-$C_6$ alkyl, $C_2$-$C_6$ alkenyl, $C_2$-$C_6$ alkynyl or a 3- to 7-membered cyclic group, wherein each $R^{41}$ is optionally substituted; and
each $R^{61}$ is independently selected from a $C_1$-$C_6$ alkyl, $C_3$-$C_6$ cycloalkyl, phenyl, benzyl, $-R^{62}$ or $-CH_2R^{62}$ group, wherein $R^{62}$ is a 5- or 6-membered heteroaryl group, and wherein any $R^{61}$ may optionally be substituted with one or more halo groups, or wherein any two $R^{61}$ together with the nitrogen atom to which they are attached may form a 3- to 6-membered heterocyclic group, wherein the 3- to 6-membered heterocyclic group may optionally be substituted with one or more halo groups.

In one embodiment, $-R^2$ has a formula selected from:

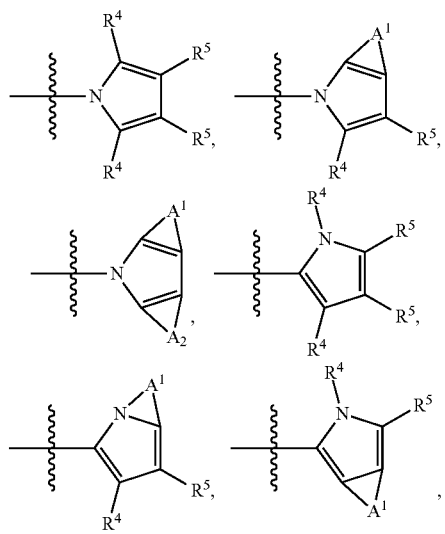

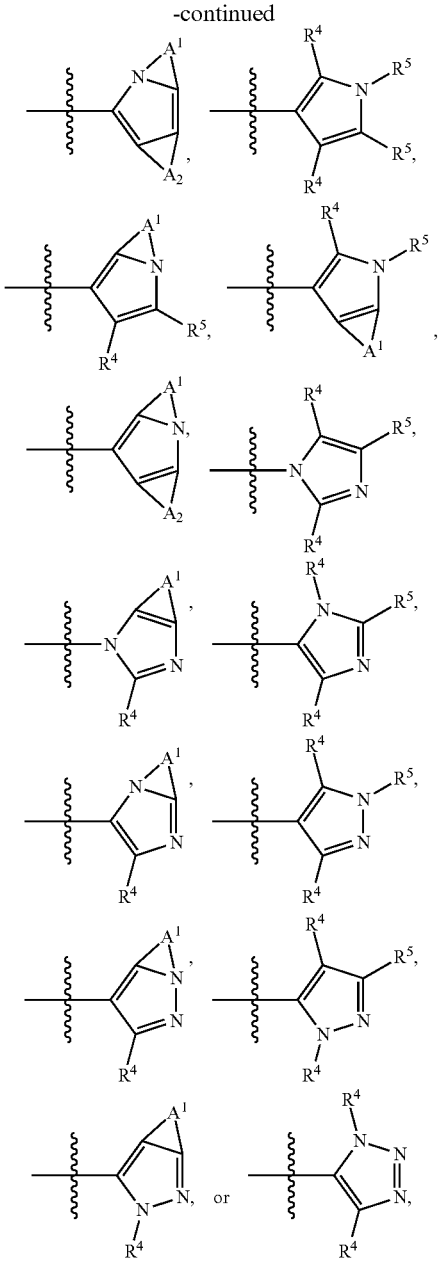

wherein:
$A^1$ and $A^2$ are each independently selected from an optionally substituted alkylene or alkenylene group, wherein one or more carbon atoms in the backbone of the alkylene or alkenylene group may optionally be replaced by one or more heteroatoms N, O or S;
each $R^4$ is independently selected from a $-R^{41}$, $-OR^{41}$ or $-COR^{41}$ group;
each $R^5$ is independently selected from hydrogen or a halo, $-R^{41}$, $-OR^{41}$ or $-COR^{41}$ group; and
each $R^{41}$ is independently selected from a $C_1$-$C_6$ alkyl, $C_2$-$C_6$ alkenyl, $C_2$-$C_6$ alkynyl or a 3- to 7-membered cyclic group, wherein each $R^{41}$ is optionally substituted;
provided that any $R^4$ or $R^5$ that is directly attached to a ring nitrogen atom is not halo or $-OR^{41}$.

In another embodiment, —R² has a formula selected from:

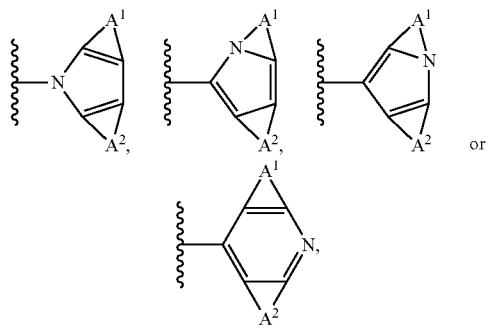

wherein A¹ and A² are each independently selected from an optionally substituted alkylene or alkenylene group, wherein one or more carbon atoms in the backbone of the alkylene or alkenylene group may optionally be replaced by one or more heteroatoms N, O or S.

Typically, in any of the above embodiments, any ring containing A¹ or A² is a 5- or 6-membered ring. Typically, A¹ and A² are each independently selected from an optionally substituted straight-chain alkylene group or an optionally substituted straight-chain alkenylene group, wherein one or two carbon atoms in the backbone of the alkylene or alkenylene group may optionally be replaced by one or two heteroatoms independently selected from nitrogen and oxygen. More typically, A¹ and A² are each independently selected from an optionally substituted straight chain alkylene group, wherein one or two carbon atoms in the backbone of the alkylene group may optionally be replaced by one or two heteroatoms independently selected from nitrogen and oxygen. More typically still, A¹ and A² are each independently selected from an optionally substituted straight-chain alkylene group, wherein one carbon atom in the backbone of the alkylene group may optionally be replaced by an oxygen atom. Typically, A¹ and A² are unsubstituted or substituted with one or more halo, —OH, —CN, —NO₂, —O(C₁-C₄ alkyl) or —O(C₁-C₄ haloalkyl) groups. More typically, A¹ and A² are unsubstituted or substituted with one or more fluoro and/or chloro groups. Where R² contains both A¹ and A² groups, A¹ and A² may be the same or different. Typically, A¹ and A² are the same.

Where R⁴¹ is a substituted C₁-C₆ alkyl, C₂-C₆ alkenyl or C₂-C₆ alkynyl group, typically the C₁-C₆ alkyl, C₂-C₆ alkenyl or C₂-C₆ alkynyl group is substituted with one or more halo, —OH, —CN, —NO₂, —O(C₁-C₄ alkyl) or —O(C₁-C₄ haloalkyl) groups. Where R⁴¹ is a substituted 3- to 7-membered cyclic group, typically the 3- to 7-membered cyclic group is substituted with one or more halo, —OH, —NH₂, —CN, —NO₂, —R⁴², —OR⁴², —NHR⁴² or —N(R⁴²)₂ groups, wherein each R⁴² is independently selected from a C₁-C₄ alkyl, C₂-C₄ alkenyl or C₂-C₄ alkynyl group all of which may optionally be halo-substituted.

Typically, each R⁴ is an —R⁴¹ group. More typically, each R⁴ is independently selected from a C₁-C₆ alkyl (in particular C₃-C₆ branched alkyl) or C₃-C₆ cycloalkyl group, wherein each R⁴ is optionally further substituted with one or more halo groups. Most typically, each R⁴ is independently selected from a C₁-C₄ alkyl group. Where a group R⁴ is present at both the α and α' positions, each R⁴ may be the same or different. Typically, each R⁴ is the same.

Typically, each R⁵ is independently selected from hydrogen or a halo group. More typically, each R⁵ is hydrogen.

Typically, R⁶ is a halo, —NO₂, —CN, —COOR⁶¹, —CONH₂, —CONHR⁶¹ or —CON(R⁶¹)₂ group, wherein each R⁶¹ is independently selected from a C₁-C₄ alkyl group, and wherein any R⁶¹ may optionally be substituted with one or more halo groups. More typically still, R⁶ is a fluoro, chloro, bromo or —CN group. Most typically, R⁶ is a bromo or —CN group.

More typically, R² has a formula selected from:

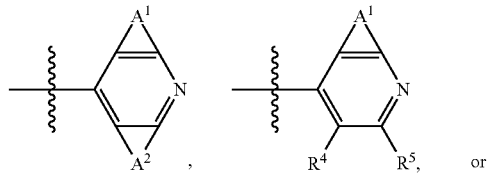

wherein:

A¹ and A² are each independently selected from a straight chain alkylene group, wherein one or two carbon atoms in the backbone of the alkylene group may optionally be replaced by one or two heteroatoms independently selected from nitrogen and oxygen, wherein the alkylene group may optionally be substituted with one or more halo, —OH, —CN, —O(C₁-C₄ alkyl) or —O(C₁-C₄ haloalkyl) groups, and wherein any ring containing A¹ or A² is a 5- or 6-membered ring;

each R⁴ is independently selected from a C₁-C₆ alkyl or C₃-C₆ cycloalkyl group, wherein the C₁-C₆ alkyl or C₃-C₆ cycloalkyl group may optionally be substituted with one or more halo, —OH, —CN, —O(C₁-C₄ alkyl) or —O(C₁-C₄ haloalkyl) groups; and each R⁵ is independently selected from hydrogen or a halo group.

In one embodiment, —R² has the formula:

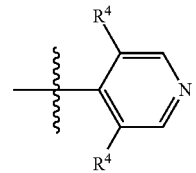

wherein each R⁴ is as defined herein. Typically, each R⁴ is independently selected from an —R⁴¹ group, wherein R⁴¹ is as defined herein. More typically, each R⁴ is independently selected from a C₁-C₄ alkyl group. Typically in such an embodiment, each R⁴ is the same.

In one embodiment, —R² has a formula selected from:

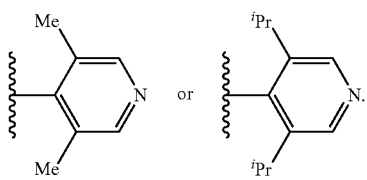 [SMILES: *c1c(C)cncc1C ; "or" ; *c1c(C(C)C)cncc1C(C)C]

In a further embodiment, —R² has a formula selected from:

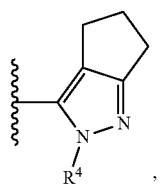

wherein R⁴ is as defined herein. Typically, R⁴ is a —R⁴¹ group, wherein R⁴¹ is as defined herein. In one aspect of such an embodiment, R⁴ is a $C_1$-$C_4$ alkyl group.

In another embodiment, —R² has a formula selected from:

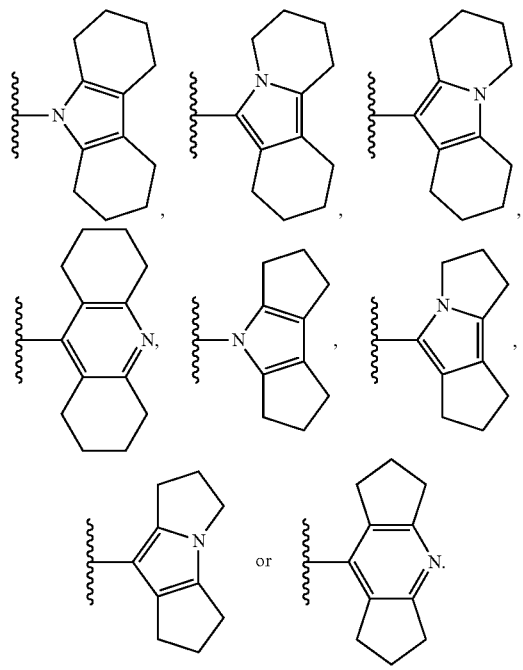

Yet other typical substituents at the α-position of the parent heteroaryl group of R² may include monovalent heterocyclic groups and monovalent aromatic groups, wherein a ring atom of the heterocyclic or aromatic group is directly attached via a single bond to the α-ring atom of the parent heteroaryl group, wherein the heterocyclic or aromatic group may optionally be substituted, and wherein the parent heteroaryl group may optionally be further substituted. Such R² groups are described in greater detail below.

In one embodiment, the α,α'-disubstituted parent heteroaryl group of R² is a 5- or 6-membered heteroaryl group, wherein the heteroaryl group may optionally be further substituted. In one embodiment, the α,α'-disubstituted heteroaryl group of R² is a pyridinyl, pyridazinyl, pyrimidinyl, pyrrolyl, furanyl, thiophenyl, pyrazolyl, imidazolyl, isoxazolyl, isothiazolyl or triazolyl group, all of which may optionally be further substituted. In one embodiment, α,α'-disubstituted parent heteroaryl group of R² is a pyridinyl group, which may optionally be further substituted. In another embodiment, the α,α'-disubstituted parent heteroaryl group of R² is a pyrazolyl group, which may optionally be further substituted.

In one embodiment, the α,α'-disubstituted parent heteroaryl group of R² is substituted at the α-position with a monovalent heterocyclic group or a monovalent aromatic group, wherein the heterocyclic or aromatic group may optionally be substituted, and wherein the parent heteroaryl group may optionally be further substituted. In one embodiment, the monovalent heterocyclic or aromatic group at the α-position is a phenyl or a 5- or 6-membered heterocyclic group, all of which may optionally be substituted. In one embodiment, the monovalent heterocyclic or aromatic group at the α-position is a phenyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, triazolyl, oxadiazolyl, azetinyl, azetidinyl, oxetanyl, thietanyl, pyrrolidinyl, tetrahydrofuranyl, tetrahydrothiophenyl, pyrazolidinyl, imidazolidinyl, 1,3-dioxolanyl, 1,2-oxathiolanyl, 1,3-oxathiolanyl, piperidinyl, tetrahydropyranyl, piperazinyl, 1,4-dioxanyl, thianyl, morpholinyl, thiomorpholinyl or 1-methyl-2-oxo-1,2-dihydropyridinyl group, all of which may optionally be substituted. In one embodiment, the monovalent heterocyclic or aromatic group at the α-position is a phenyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, triazolyl, oxadiazolyl, azetinyl, azetidinyl, oxetanyl, thietanyl, pyrrolidinyl, tetrahydrofuranyl, tetrahydrothiophenyl, pyrazolidinyl, imidazolidinyl, 1,3-dioxolanyl, 1,2-oxathiolanyl, 1,3-oxathiolanyl, piperidinyl, tetrahydropyranyl, thianyl, piperazinyl, 1,4-dioxanyl, morpholinyl or thiomorpholinyl group, all of which may optionally be substituted. In one embodiment, the monovalent heterocyclic or aromatic group at the α-position is a phenyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, piperidinyl or tetrahydropyranyl group, all of which may optionally be substituted. In one embodiment, the monovalent heterocyclic or aromatic group at the α-position is a phenyl, pyridinyl, pyridazinyl, pyrimidinyl, pyrazolyl, imidazolyl, isoxazolyl, thiazolyl, tetrahydropyranyl or 1-methyl-2-oxo-1,2-dihydropyridinyl group, all of which may optionally be substituted. In one embodiment, the monovalent heterocyclic or aromatic group at the α-position is a phenyl, pyridinyl, pyrimidinyl, pyrazolyl, imidazolyl, isoxazolyl, thiazolyl or tetrahydropyranyl group, all of which may optionally be substituted. In one embodiment, the monovalent heterocyclic or aromatic group at the α-position is a phenyl, pyridinyl, pyrimidinyl or pyrazolyl group, all of which may optionally be substituted. In one embodiment, the monovalent heterocyclic or aromatic group at the α-position is an unsubstituted phenyl, pyridinyl, pyrimidinyl or pyrazolyl group. In one embodiment, the monovalent heterocyclic group at the α-position is a pyridin-2-yl, pyridin-3-yl or pyridin-4-yl group, all of which may optionally be substituted. In one embodiment, the monovalent heterocyclic group at the α-position is an unsubstituted pyridin-3-yl group or an optionally substituted pyridin-4-yl group.

For any of these monovalent heterocyclic or aromatic groups at the α-position mentioned in the immediately preceding paragraph, the monovalent heterocyclic or aromatic group may optionally be substituted with one or two substituents independently selected from halo, —OH, —NH$_2$, —CN, —NO$_2$, —R$^{81}$, —OR$^{81}$, —NHR$^{81}$, —N(R$^{81}$)$_2$, —CONH$_2$, —CONHR$^{81}$, —CON(R$^{81}$)$_2$, —NHCOR$^{81}$, —NR$^{81}$COR$^{81}$, or —R$^{88}$—;

wherein each R$^{81}$ is independently selected from a C$_1$-C$_4$ alkyl, C$_2$-C$_4$ alkenyl, C$_2$-C$_4$ alkynyl, C$_3$-C$_6$ cycloalkyl or phenyl group, or a 4- to 6-membered heterocyclic group containing one or two ring heteroatoms N and/or O, or two R$^{81}$ together with the nitrogen atom to which they are attached may form a 4- to 6-membered heterocyclic group containing one or two ring heteroatoms N and/or O, wherein any R$^{81}$ may optionally be halo-substituted and/or substituted with one or two substituents independently selected from —OH, —NH$_2$, —OR$^{85}$, —NHR$^{85}$ or —N(R$^{85}$)$_2$;

wherein each R$^{88}$ is independently selected from a C$_1$-C$_8$ alkylene or C$_2$-C$_8$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —NH$_2$, —OR$^{85}$, —NHR$^{85}$ or —N(R$^{85}$)$_2$; and wherein each R$^{85}$ is independently selected from a C$_1$-C$_3$ alkyl or C$_1$-C$_3$ haloalkyl group.

Typically, any divalent group —R$^{88}$— forms a 4- to 6-membered fused ring.

In one embodiment, the monovalent heterocyclic or aromatic group at the α-position is a phenyl, pyridinyl, pyrimidinyl or pyrazolyl group, all of which may optionally be substituted with one or two substituents independently selected from halo, —OH, —NH$_2$, —CN, —NO$_2$, —R$^{81}$, —OR$^{81}$, —NHR$^{81}$ or —N(R$^{81}$)$_2$, wherein each R$^{81}$ is independently selected from a C$_1$-C$_4$ alkyl, C$_2$-C$_4$ alkenyl or C$_2$-C$_4$ alkynyl group all of which may optionally be halo-substituted. In one embodiment, the monovalent heterocyclic group at the α-position is a pyridin-2-yl, pyridin-3-yl or pyridin-4-yl group, all of which may optionally be substituted with one or two substituents independently selected from halo, —OH, —NH$_2$, —CN, —NO$_2$, —R$^{81}$, —OR$^{81}$, —NHR$^{81}$ or —N(R$^{81}$)$_2$, wherein each R$^{81}$ is independently selected from a C$_1$-C$_4$ alkyl, C$_2$-C$_4$ alkenyl or C$_2$-C$_4$ alkynyl group all of which may optionally be halo-substituted. In one embodiment, the monovalent heterocyclic group so at the α-position is an unsubstituted pyridin-3-yl group or a pyridin-4-yl group optionally substituted with one or two substituents independently selected from halo, —OH, —NH$_2$, —CN, —NO$_2$, —R$^{81}$, —OR$^{81}$, —NHR$^{81}$ or —N(R$^{81}$)$_2$, wherein each R$^{81}$ is independently selected from a C$_1$-C$_4$ alkyl, C$_2$-C$_4$ alkenyl or C$_2$-C$_4$ alkynyl group all of which may optionally be halo-substituted.

Where the α,α'-disubstituted parent heteroaryl group of R$^2$ is substituted at the α-position with a monovalent heterocyclic group or a monovalent aromatic group, typical substituents at the α' position may be independently selected from halo, —R$^{71}$, —OR$^{71}$ or —COR$^{71}$ groups, wherein each R$^{71}$ is independently selected from a C$_1$-C$_6$ alkyl, C$_2$-C$_6$ alkenyl, C$_2$-C$_6$ alkynyl or C$_2$-C$_6$ cyclic group and wherein each R$^{71}$ is optionally further substituted with one or more halo groups. More typically, substituents at the α' position may be independently selected from C$_1$-C$_6$ alkyl (in particular C$_3$-C$_6$ branched alkyl) or C$_3$-C$_6$ cycloalkyl groups, e.g. isopropyl, cyclopropyl, cyclohexyl or t-butyl groups, wherein the alkyl and cycloalkyl groups are optionally further substituted with one or more fluoro and/or chloro groups.

In one embodiment, —R$^2$ has the formula:

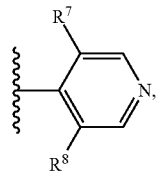

wherein R$^7$ is a C$_1$-C$_4$ alkyl group and R$^8$ is a 5- or 6-membered, optionally substituted heterocyclic or aromatic group. In one embodiment, the optional substituents on the heterocyclic or aromatic group are independently selected from halo, —OH, —NH$_2$, —CN, —NO$_2$, —R$^{82}$, —OR$^{82}$, —NHR$^{82}$ or —N(R$^{82}$)$_2$, wherein each R$^{82}$ is independently selected from a C$_1$-C$_4$ alkyl, C$_2$-C$_4$ alkenyl or C$_2$-C$_4$ alkynyl group all of which may optionally be halo-substituted.

Typically, —R$^2$ has the formula:

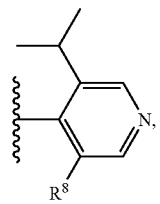

wherein R$^8$ is a 5- or 6-membered, optionally substituted heterocyclic or aromatic group. In one embodiment, the optional substituents on the heterocyclic or aromatic group are independently selected from halo, —OH, —NH$_2$, —CN, —NO$_2$, —R$^{82}$, —OR$^{82}$, —NHR$^{82}$ or —N(R$^{82}$)$_2$, wherein each R$^{82}$ is independently selected from a C$_1$-C$_4$ alkyl, C$_2$-C$_4$ alkenyl or C$_2$-C$_4$ alkynyl group all of which may optionally be halo-substituted.

In one embodiment, where the α,α'-disubstituted parent heteroaryl group of R$^2$ is substituted at the α-position with a monovalent heterocyclic group or a monovalent aromatic group, a cycloalkyl, cycloalkenyl, non-aromatic heterocyclic, aryl or heteroaryl ring is ortho-fused to the parent heteroaryl group of R$^2$ across the α',β' positions, wherein R$^2$ may optionally be further substituted.

In one embodiment, —R$^2$ has the formula:

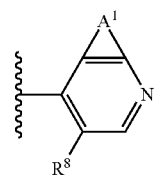

wherein A$^1$ is a straight chain alkylene group, wherein one or two carbon atoms in the backbone of the alkylene group may optionally be replaced by one or two heteroatoms independently selected from nitrogen and oxygen, wherein the alkylene group may optionally be substituted with one or more halo, —OH, —CN, —O(C$_1$-C$_4$ alkyl) or —O(C$_1$-C$_4$ haloalkyl) groups, and wherein the ring containing $A^1$ is a 5- or 6-membered ring, and $R^8$ is a 5- or 6-membered, optionally substituted heterocyclic or aromatic group. Typically, the optional substituents on the heterocyclic or aromatic group are independently selected from halo, —OH, —NH$_2$, —CN, —NO$_2$, —R$^{82}$, —OR$^{82}$, —NHR$^{82}$ or —N(R$^{82}$)$_2$, wherein each $R^{82}$ is independently selected from a $C_1$-$C_4$ alkyl, $C_2$-$C_4$ alkenyl or $C_2$-$C_4$ alkynyl group all of which may optionally be halo-substituted.

In another embodiment, —R$^2$ has a formula selected from:

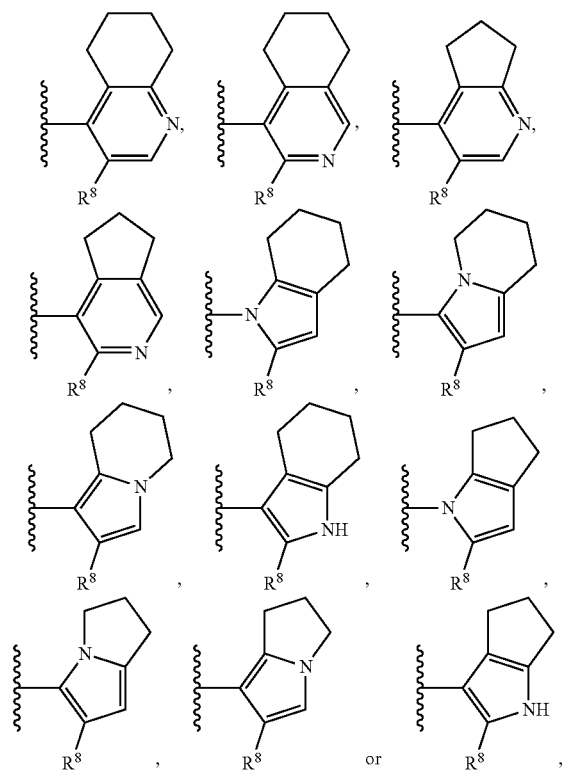

wherein $R^8$ is a 5- or 6-membered, optionally substituted heterocyclic or aromatic group. In one embodiment, the optional substituents on the heterocyclic or aromatic group are independently selected from halo, —OH, —NH$_2$, —CN, —NO$_2$, —R$^{82}$, —OR$^{82}$, —NHR$^{82}$ or —N(R$^{82}$)$_2$, wherein each $R^{82}$ is independently selected from a $C_1$-$C_4$ alkyl, $C_2$-$C_4$ alkenyl or $C_2$-$C_4$ alkynyl group all of which may optionally be halo-substituted.

In yet another embodiment, —R$^2$ has the formula:

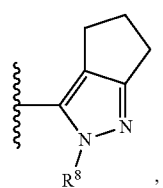

wherein $R^8$ is a 5- or 6-membered, optionally substituted heterocyclic or aromatic group. Typically, $R^8$ is an optionally substituted phenyl or 6-membered heteroaryl group (such as an optionally substituted pyridinyl, pyridazinyl, pyrimidinyl or pyrazinyl group). In one embodiment, the optional substituents on the heterocyclic or aromatic group are independently selected from halo, —OH, —NH$_2$, —CN, —NO$_2$, —R$^{82}$, —OR$^{82}$, —NHR$^{82}$ or —N(R$^{82}$)$_2$, wherein each $R^{82}$ is independently selected from a $C_1$-$C_4$ alkyl, $C_2$-$C_4$ alkenyl or $C_2$-$C_4$ alkynyl group all of which may optionally be halo-substituted. Typically the optional substituents on the heterocyclic or aromatic group are independently selected from halo, —OH, —CN, —NO$_2$, —R$^{82}$ or —OR$^{82}$, wherein each $R^{82}$ is independently selected from a $C_1$-$C_4$ alkyl or $C_1$-$C_4$ haloalkyl group. More typically, the optional substituents on the heterocyclic or aromatic group are independently selected from fluoro, chloro, —CN, methyl or —OMe, wherein any methyl (Me) group may optionally be substituted with one or more fluoro and/or chloro groups.

In one aspect of any of the above embodiments where $R^8$ is a 5- or 6-membered, optionally substituted heterocyclic or aromatic group, the heterocyclic or aromatic group may be substituted with one, two, three, four or five halo groups and/or with one or two non-halo groups (e.g. OH, —NH$_2$, —CN, —NO$_2$, —R$^{82}$, —OR$^{82}$, —NHR$^{82}$ or —N(R$^{82}$)$_2$). More typically, the heterocyclic or aromatic group may be substituted with one, two, three, four or five halo groups and/or with a single non-halo group (e.g. OH, —NH$_2$, —CN, —NO$_2$, —R$^{82}$, —OR$^{82}$, —NHR$^{82}$ or —N(R$^{82}$)$_2$).

In one aspect of any of the above embodiments, $R^2$ contains from 5 to 50 atoms other than hydrogen. More typically, $R^2$ contains from 7 to 40 atoms other than hydrogen. More typically, $R^2$ contains from 8 to 35 atoms other than hydrogen. Most typically, $R^2$ contains from 8 to 30 atoms other than hydrogen.

In one aspect of any of the above embodiments, $R^2$ contains from 5 to 30 atoms other than hydrogen or halogen. More typically, $R^2$ contains from 7 to 25 atoms other than hydrogen or halogen. More typically, $R^2$ contains from 8 to 20 atoms other than hydrogen or halogen. Most typically, $R^2$ contains from 8 to 16 atoms other than hydrogen or halogen.

Q is selected from O or S. In one embodiment of the first aspect of the invention, Q is O.

In one aspect of any of the above embodiments, the compound of formula (I) has a molecular weight of from 250 to 2000 Da. Typically, the compound of formula (I) has a molecular weight of from 300 to 900 Da. More typically, the compound of formula (I) has a molecular weight of from 350 to 600 Da.

A second aspect of the invention provides a compound selected from the group consisting of:

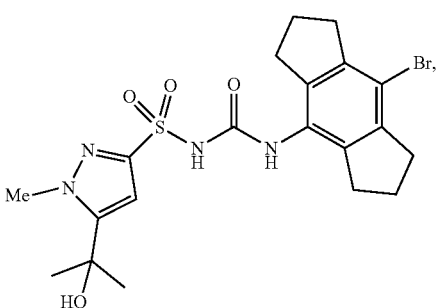

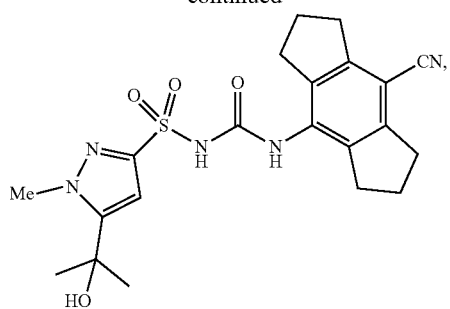
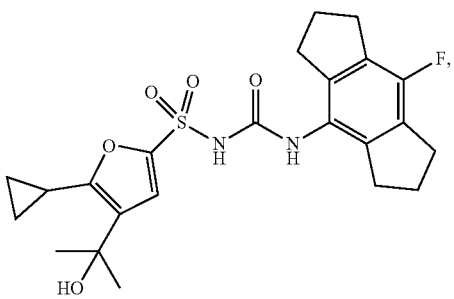
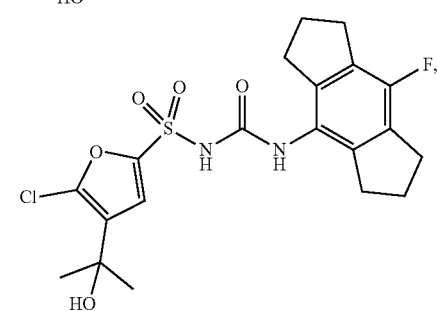
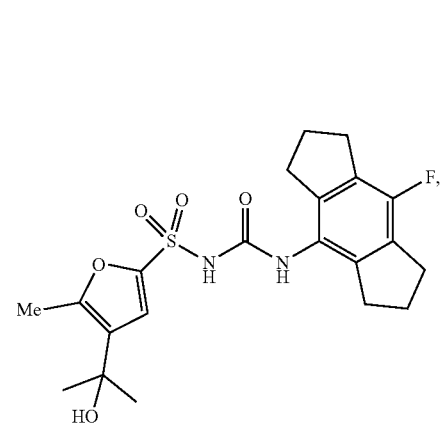
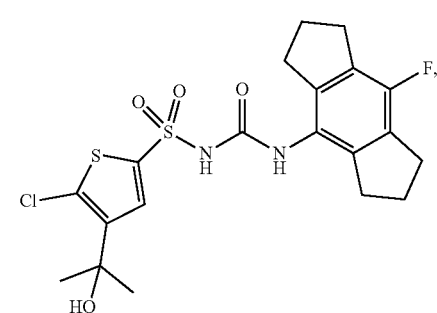
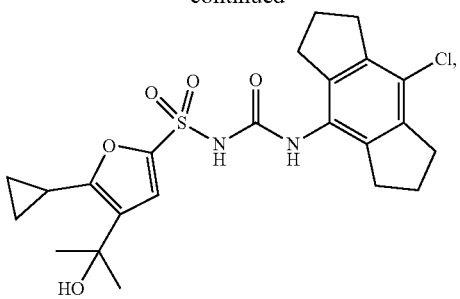
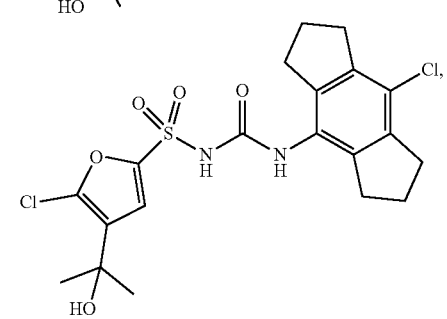
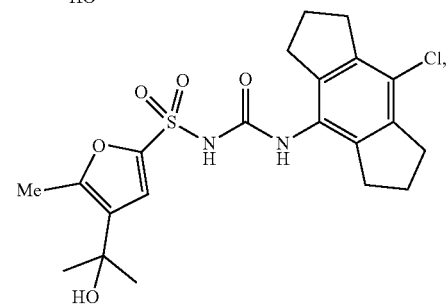
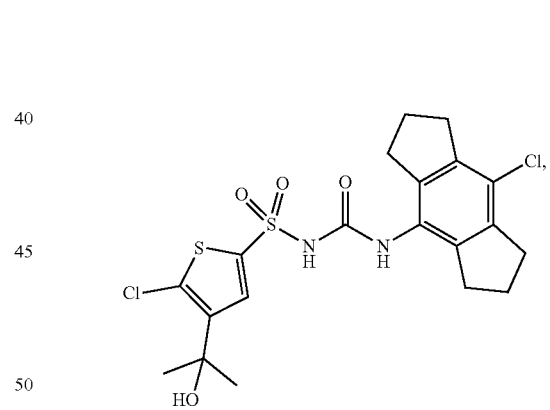
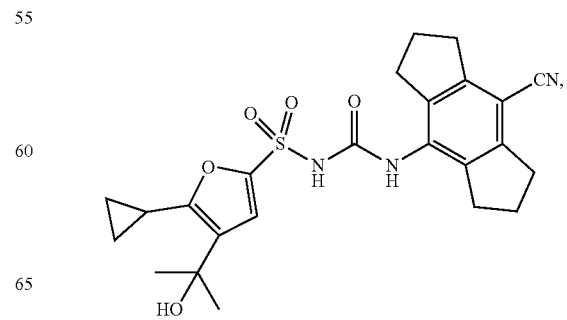

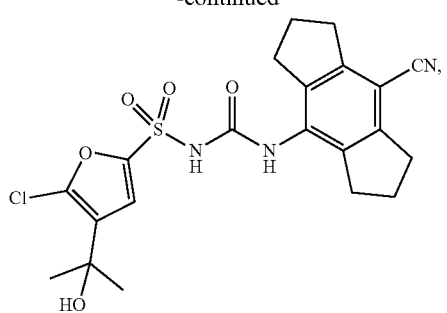
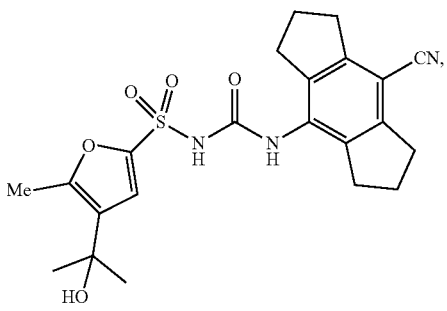
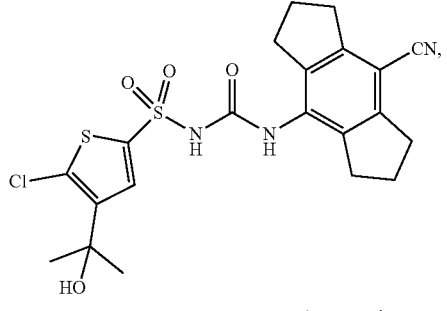
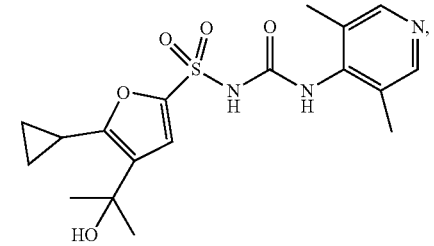
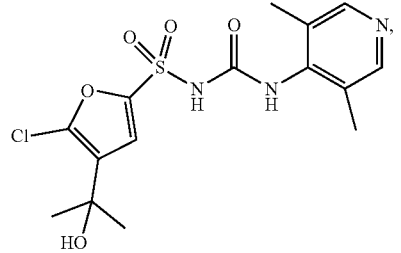
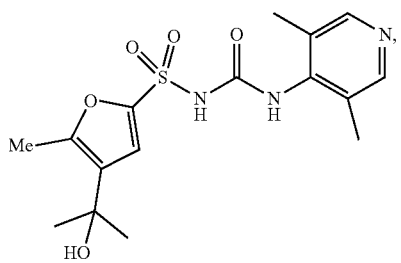
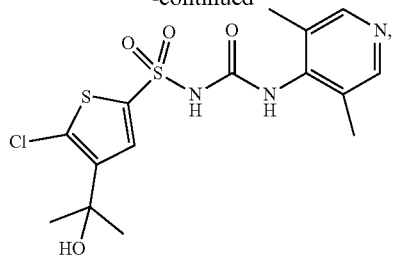
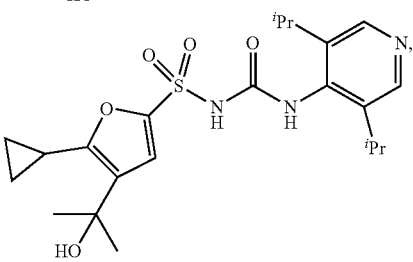
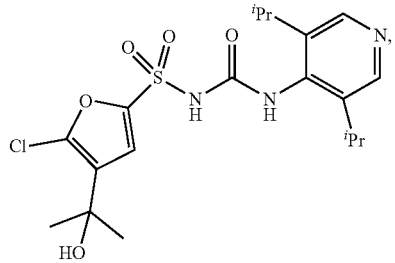
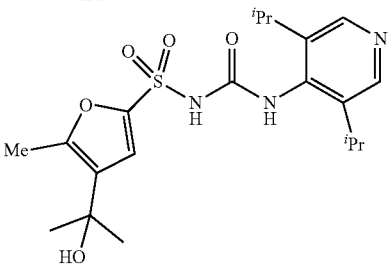
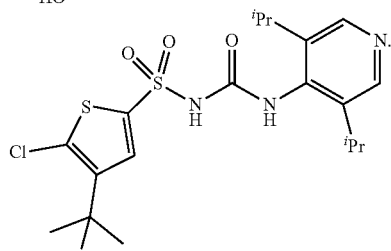

and

A third aspect of the invention provides a pharmaceutically acceptable salt, solvate or prodrug of any compound of the first or second aspect of the invention.

The compounds of the present invention can be used both in their free base form and their acid addition salt form. For the purposes of this invention, a "salt" of a compound of the present invention includes an acid addition salt. Acid addition salts are preferably pharmaceutically acceptable, non-toxic addition salts with suitable acids, including but not limited to inorganic acids such as hydrohalogenic acids (for example, hydrofluoric, hydrochloric, hydrobromic or hydroiodic acid) or other inorganic acids (for example, nitric, perchloric, sulfuric or phosphoric acid); or organic acids such as organic carboxylic acids (for example, propionic, butyric, glycolic, lactic, mandelic, citric, acetic, benzoic, salicylic, succinic, malic or hydroxysuccinic, tartaric, fumaric, maleic, hydroxymaleic, mucic or galactaric, gluconic, pantothenic or pamoic acid), organic sulfonic acids (for example, methanesulfonic, trifluoromethanesulfonic, ethanesulfonic, 2-hydroxyethanesulfonic, benzenesulfonic, toluene-p-sulfonic, naphthalene-2-sulfonic or camphorsulfonic acid) or amino acids (for example, ornithinic, glutamic or aspartic acid). The acid addition salt may be a mono-, di-, tri- or multi-acid addition salt. A preferred salt is a hydrohalogenic, sulfuric, phosphoric or organic acid addition salt. A preferred salt is a hydrochloric acid addition salt.

Where a compound of the invention includes a quaternary ammonium group, typically the compound is used in its salt form. The counter ion to the quaternary ammonium group may be any pharmaceutically acceptable, non-toxic counter ion. Examples of suitable counter ions include the conjugate bases of the protic acids discussed above in relation to acid-addition salts.

The compounds of the present invention can also be used both, in their free acid form and their salt form. For the purposes of this invention, a "salt" of a compound of the present invention includes one formed between a protic acid functionality (such as a carboxylic acid group) of a compound of the present invention and a suitable cation. Suitable cations include, but are not limited to lithium, sodium, potassium, magnesium, calcium and ammonium. The salt may be a mono-, di-, tri- or multi-salt. Preferably the salt is a mono- or di-lithium, sodium, potassium, magnesium, calcium or ammonium salt. More preferably the salt is a mono- or di-sodium salt or a mono- or di-potassium salt.

Preferably any salt is a pharmaceutically acceptable non-toxic salt. However, in addition to pharmaceutically acceptable salts, other salts are included in the present invention, since they have potential to serve as intermediates in the purification or preparation of other, for example, pharmaceutically acceptable salts, or are useful for identification, characterisation or purification of the free acid or base.

The compounds and/or salts of the present invention may be anhydrous or in the form of a hydrate (e.g. a hemihydrate, monohydrate, dihydrate or trihydrate) or other solvate. Such solvates may be formed with common organic solvents, including but not limited to, alcoholic solvents e.g. methanol, ethanol or isopropanol.

In some embodiments of the present invention, therapeutically inactive prodrugs are provided. Prodrugs are compounds which, when administered to a subject such as a human, are converted in whole or in part to a compound of the invention. In most embodiments, the prodrugs are pharmacologically inert chemical derivatives that can be converted in vivo to the active drug molecules to exert a therapeutic effect. Any of the compounds described herein can be administered as a prodrug to increase the activity, bioavailability, or stability of the compound or to otherwise alter the properties of the compound. Typical examples of prodrugs include compounds that have biologically labile protecting groups on a functional moiety of the active compound. Prodrugs include, but are not limited to, compounds that can be oxidized, reduced, aminated, deaminated, hydroxylated, dehydroxylated, hydrolyzed, dehydrolyzed, alkylated, dealkylated, acylated, deacylated, phosphorylated, and/or dephosphorylated to produce the active compound. The present invention also encompasses salts and solvates of such prodrugs as described above.

The compounds, salts, solvates and prodrugs of the present invention may contain at least one chiral centre. The compounds, salts, solvates and prodrugs may therefore exist in at least two isomeric forms. The present invention encompasses racemic mixtures of the compounds, salts, solvates and prodrugs of the present invention as well as enantiomerically enriched and substantially enantiomerically pure isomers. For the purposes of this invention, a "substantially enantiomerically pure" isomer of a compound comprises less than 5% of other isomers of the same compound, more typically less than 2%, and most typically less than 0.5% by weight.

The compounds, salts, solvates and prodrugs of the present invention may contain any stable isotope including, but not limited to $^{12}C$, $^{13}C$, $^{1}H$, $^{2}H$ (D), $^{14}N$, $^{15}N$, $^{16}O$, $^{17}O$, $^{18}O$, $^{19}F$ and $^{127}I$, and any radioisotope including, but not limited to $^{11}C$, $^{14}C$, $^{3}H$ (T), $^{13}N$, $^{15}O$, $^{18}F$, $^{123}I$, $^{124}I$, $^{125}I$ and $^{131}I$.

The compounds, salts, solvates and prodrugs of the present invention may be in any polymorphic or amorphous form.

A fourth aspect of the invention provides a pharmaceutical composition comprising a compound of the first or second aspect of the invention, or a pharmaceutically acceptable salt, solvate or prodrug of the third aspect of the invention, and a pharmaceutically acceptable excipient.

Conventional procedures for the selection and preparation of suitable pharmaceutical formulations are described in, for example, "Aulton's Pharmaceutics—The Design and Manufacture of Medicines", M. E. Aulton and K. M. G. Taylor, Churchill Livingstone Elsevier, 4$^{th}$ Ed., 2013.

Pharmaceutically acceptable excipients including adjuvants, diluents or carriers that may be used in the pharmaceutical compositions of the invention are those conventionally employed in the field of pharmaceutical formulation, and include, but are not limited to, sugars, sugar alcohols, starches, ion exchangers, alumina, aluminium stearate, lecithin, serum proteins such as human serum albumin, buffer substances such as phosphates, glycerine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinylpyrrolidone, cellulose-based substances, polyethylene glycol, sodium carboxymethylcellulose, polyacrylates, waxes, polyethylene-polyoxypropylene-block polymers, polyethylene glycol and wool fat.

In one embodiment, the pharmaceutical composition of the fourth aspect of the invention additionally comprises one or more further active agents.

In a further embodiment, the pharmaceutical composition of the fourth aspect of the invention may be provided as a part of a kit of parts, wherein the kit of parts comprises the pharmaceutical composition of the fourth aspect of the invention and one or more further pharmaceutical compositions, wherein the one or more further pharmaceutical compositions each comprise a pharmaceutically acceptable excipient and one or more further active agents.

A fifth aspect of the invention provides a compound of the first or second aspect of the invention, or a pharmaceutically acceptable salt, solvate or prodrug of the third aspect of the invention, or a pharmaceutical composition of the fourth aspect of the invention, for use in medicine, and/or for use in the treatment or prevention of a disease, disorder or condition. Typically, the use comprises the administration of the compound, salt, solvate, prodrug or pharmaceutical composition to a subject. In one embodiment, the use comprises the co-administration of one or more further active agents.

The term "treatment" as used herein refers equally to curative therapy, and ameliorating or palliative therapy. The term includes obtaining beneficial or desired physiological results, which may or may not be established clinically. Beneficial or desired clinical results include, but are not limited to, the alleviation of symptoms, the prevention of symptoms, the diminishment of extent of disease, the stabilisation (i.e., not worsening) of a condition, the delay or slowing of progression/worsening of a condition/symptoms, the amelioration or palliation of the condition/symptoms, and remission (whether partial or total), whether detectable or undetectable. The term "palliation", and variations thereof, as used herein, means that the extent and/or undesirable manifestations of a physiological condition or symptom are lessened and/or time course of the progression is slowed or lengthened, as compared to not administering a compound, salt, solvate, prodrug or pharmaceutical composition of the present invention. The term "prevention" as used herein in relation to a disease, disorder or condition, relates to prophylactic or preventative therapy, as well as therapy to reduce the risk of developing the disease, disorder or condition. The term "prevention" includes both the avoidance of occurrence of the disease, disorder or condition, and the delay in onset of the disease, disorder or condition. Any statistically significant (p≤0.05) avoidance of occurrence, delay in onset or reduction in risk as measured by a controlled clinical trial may be deemed a prevention of the disease, disorder or condition. Subjects amenable to prevention include those at heightened risk of a disease, disorder or condition as identified by genetic or biochemical markers. Typically, the genetic or biochemical markers are appropriate to the disease, disorder or condition under consideration and may include for example, inflammatory biomarkers such as C-reactive protein (CRP) and monocyte chemoattractant protein 1 (MCP-1) in the case of inflammation; total cholesterol, triglycerides, insulin resistance and C-peptide in the case of NAFLD and NASH; and more generally IL1β and IL18 in the case of a disease, disorder or condition responsive to NLRP3 inhibition.

A sixth aspect of the invention provides the use of a compound of the first or second aspect, or a pharmaceutically effective salt, solvate or prodrug of the third aspect, in the manufacture of a medicament for the treatment or prevention of a disease, disorder or condition. Typically, the treatment or prevention comprises the administration of the compound, salt, solvate, prodrug or medicament to a subject. In one embodiment, the treatment or prevention comprises the co-administration of one or more further active agents.

A seventh aspect of the invention provides a method of treatment or prevention of a disease, disorder or condition, the method comprising the step of administering an effective amount of a compound of the first or second aspect, or a pharmaceutically acceptable salt, solvate or prodrug of the third aspect, or a pharmaceutical composition of the fourth aspect, to thereby treat or prevent the disease, disorder or condition. In one embodiment, the method further comprises the step of co-administering an effective amount of one or more further active agents. Typically, the administration is to a subject in need thereof.

An eighth aspect of the invention provides a compound of the first or second aspect of the invention, or a pharmaceutically acceptable salt, solvate or prodrug of the third aspect of the invention, or a pharmaceutical composition of the fourth aspect of the invention, for use in the treatment or prevention of a disease, disorder or condition in an individual, wherein the individual has a germline or somatic non-silent mutation in NLRP3. The mutation may be, for example, a gain-of-function or other mutation resulting in increased NLRP3 activity. Typically, the use comprises the administration of the compound, salt, solvate, prodrug or pharmaceutical composition to the individual. In one embodiment, the use comprises the co-administration of one or more further active agents. The use may also comprise the diagnosis of an individual having a germline or somatic non-silent mutation in NLRP3, wherein the compound, salt, solvate, prodrug or pharmaceutical composition is administered to an individual on the basis of a positive diagnosis for the mutation. Typically, identification of the mutation in NLRP3 in the individual may be by any suitable genetic or biochemical means.

A ninth aspect of the invention provides the use of a compound of the first or second aspect, or a pharmaceutically effective salt, solvate or prodrug of the third aspect, in the manufacture of a medicament for the treatment or prevention of a disease, disorder or condition in an individual, wherein the individual has a germline or somatic non-silent mutation in NLRP3. The mutation may be, for example, a gain-of-function or other mutation resulting in increased NLRP3 activity. Typically, the treatment or prevention comprises the administration of the compound, salt, solvate, prodrug or medicament to the individual. In one embodiment, the treatment or prevention comprises the co-administration of one or more further active agents. The treatment or prevention may also comprise the diagnosis of an individual having a germline or somatic non-silent mutation in NLRP3, wherein the compound, salt, solvate, prodrug or medicament is administered to an individual on the basis of a positive diagnosis for the mutation. Typically, identification of the mutation in NLRP3 in the individual may be by any suitable genetic or biochemical means.

A tenth aspect of the invention provides a method of treatment or prevention of a disease, disorder or condition, the method comprising the steps of diagnosing of an individual having a germline or somatic non-silent mutation in NLRP3, and administering an effective amount of a compound of the first or second aspect, or a pharmaceutically acceptable salt, solvate or prodrug of the third aspect, or a pharmaceutical composition of the fourth aspect, to the positively diagnosed individual, to thereby treat or prevent the disease, disorder or condition. In one embodiment, the method further comprises the step of co-administering an effective amount of one or more further active agents. Typically, the administration is to a subject in need thereof.

In general embodiments, the disease, disorder or condition may be a disease, disorder or condition of the immune system, the cardiovascular system, the endocrine system, the gastrointestinal tract, the renal system, the hepatic system, the metabolic system, the respiratory system, the central nervous system, may be a cancer or other malignancy, and/or may be caused by or associated with a pathogen.

It will be appreciated that these general embodiments defined according to broad categories of diseases, disorders and conditions are not mutually exclusive. In this regard any particular disease, disorder or condition may be categorized according to more than one of the above general embodiments. A non-limiting example is type I so diabetes which is an autoimmune disease and a disease of the endocrine system.

In one embodiment of the fifth, sixth, seventh, eighth, ninth or tenth aspect of the invention, the disease, disorder or condition is responsive to NLRP3 inhibition. As used herein, the term "NLRP3 inhibition" refers to the complete or partial reduction in the level of activity of NLRP3 and includes, for example, the inhibition of active NLRP3 and/or the inhibition of activation of NLRP3.

There is evidence for a role of NLRP3-induced IL-1 and IL-18 in the inflammatory responses occurring in connection with, or as a result of, a multitude of different disorders (Menu et al., Clinical and Experimental Immunology, 166: 1-15, 2011; Strowig et al., Nature, 481:278-286, 2012).

NLRP3 has been implicated in a number of autoinflammatory diseases, including Familial Mediterranean fever (FMF), TNF receptor associated periodic syndrome (TRAPS), hyperimmunoglobulinemia D and periodic fever syndrome (HIDS), pyogenic arthritis, pyoderma gangrenosum and acne (PAPA), Sweet's syndrome, chronic nonbacterial osteomyelitis (CNO), and acne vulgaris (Cook et al., Eur. J. Immunol., 40: 595-653, 2010). In particular, NLRP3 mutations have been found to be responsible for a set of rare autoinflammatory diseases known as CAPS (Ozaki et al., J. Inflammation Research, 8:15-27, 2015; Schroder et al., Cell, 140: 821-832, 2010; and Menu et al., Clinical and Experimental Immunology, 166: 1-15, 2011). CAPS are heritable diseases characterized by recurrent fever and inflammation and are comprised of three autoinflammatory disorders that form a clinical continuum. These diseases, in order of increasing severity, are familial cold autoinflammatory syndrome (FCAS), Muckle-Wells syndrome (MWS), and chronic infantile cutaneous neurological articular syndrome (CINCA; also called neonatal-onset multisystem inflammatory disease, NOMID), and all have been shown to result from gain-of-function mutations in the NLRP3 gene, which leads to increased secretion of IL-1$\beta$.

A number of autoimmune diseases have been shown to involve NLRP3 including, in particular, multiple sclerosis, type-1 diabetes (T1D), psoriasis, rheumatoid arthritis (RA), Behcet's disease, Schnitzler syndrome, macrophage activation syndrome (Masters Clin. Immunol. 2013; Braddock et al. Nat. Rev. Drug Disc. 2004 3: 1-10; Inoue et al., Immunology 139: 11-18, Coll et al. Nat. Med. 2015 21(3):248-55; and Scott et al. Clin. Exp. Rheumatol 2016 34(1): 88-93), systemic lupus erythematosus (Lu et al. J Immunol. 2017 198(3): 1119-29), and systemic sclerosis (Artlett et al. Arthritis Rheum. 2011; 63(11): 3563-74). NLRP3 has also been shown to play a role in a number of lung diseases including chronic obstructive pulmonary disorder (COPD), asthma (including steroid-resistant asthma), asbestosis, and silicosis (De Nardo et al., Am. J. Pathol., 184: 42-54, 2014 and Kim et al. Am J Respir Crit Care Med. 2017 196(3): 283-97). NLRP3 has also been suggested to have a role in a number of central nervous system conditions, including Parkinson's disease (PD), Alzheimer's disease (AD), dementia, Huntington's disease, cerebral malaria, brain injury from pneumococcal meningitis (Walsh et al., Nature Reviews, 15: 84-97, 2014, and Dempsey et al. Brain. Behav. Immun. 2017 61: 306-316), intracranial aneurysms (Zhang et al. J. Stroke & Cerebrovascular Dis. 2015 24; 5: 972-979), and traumatic brain injury (Ismael et al. J Neurotrauma. 2018 Jan. 2). NRLP3 activity has also been shown to be involved in various metabolic diseases including type 2 diabetes (T2D), atherosclerosis, obesity, gout, pseudo-gout, metabolic syndrome (Wen et al., Nature Immunology, 13: 352-357, 2012; Duewell et al., Nature, 464: 1357-1361, 2010; Strowig et al., Nature, 481: 278-286, 2012), and non-alcoholic steatohepatitis (Mridha et al. J Hepatol. 2017 66(5): 1037-46). A role for NLRP3 via IL-1$\beta$ has also been suggested in atherosclerosis, myocardial infarction (van Hout et al. Eur. Heart J. 2017 38(11): 828-36), heart failure (Sano et al. J AM. Coll. Cardiol. 2018 71(8): 875-66), aortic aneurysm and dissection (Wu et al. Arterioscler. Thromb. Vasc. Biol. 2017 37(4): 694-706), and other cardiovascular events (Ridker et al., N Engl J Med., doi: 10.1056/NEJMoa1707914, 2017). Other diseases in which NLRP3 has been shown to be involved include: ocular diseases such as both wet and dry age-related macular degeneration (Doyle et al., Nature Medicine, 18: 791-798, 2012 and Tarallo et al. Cell 2012 149(4): 847-59), diabetic retinopathy (Loukovaara et al. Acta Ophthalmol. 2017; 95(8): 803-808) and optic nerve damage (Puyang et al. Sci Rep. 2016 Feb. 19; 6:20998); liver diseases including non-alcoholic steatohepatitis (NASH) (Henao-Meija et al., Nature, 482: 179-185, 2012); inflammatory reactions in the lung and skin (Primiano et al. J Immunol. 2016 197(6): 2421-33) including contact hypersensitivity (such as bullous pemphigoid (Fang et al. J Dermatol Sci. 2016; 83(2): 116-23)), atopic dermatitis (Niebuhr et al. Allergy 2014 69(8): 1058-67), Hidradenitis suppurativa (Alikhan et al. 2009 J Am Acad Dermatol 60(4): 539-61), acne vulgaris (Qin et al. J Invest. Dermatol. 2014 134(2): 381-88), and sarcoidosis (Jager et al. Am J Respir Crit Care Med 2015 191: A5816); inflammatory reactions in the joints (Braddock et al., Nat. Rev. Drug Disc., 3: 1-10, 2004); amyotrophic lateral sclerosis (Gugliandolo et al. Inflammation 2018 41(1): 93-103); cystic fibrosis (Iannitti et al. Nat. Commun. 2016 7: 10791); stroke (Walsh et al., Nature Reviews, 15: 84-97, 2014); chronic kidney disease (Granata et al. PLoS One 2015 10(3): e0122272); and inflammatory bowel diseases including ulcerative colitis and Crohn's disease (Braddock et al., Nat. Rev. Drug Disc., 3: 1-10, 2004, Neudecker et al. J Exp. Med. 2017 214(6): 1737-52, and Lazaridis et al. Dig. Dis. Sci. 2017 62(9): 2348-56). The NLRP3 inflammasome has been found to be activated in response to oxidative stress, and UVB irradiation (Schroder et al., Science, 327: 296-300, 2010). NLRP3 has also been shown to be involved in inflammatory hyperalgesia (Dolunay et al., Inflammation, 40: 366-386, 2017).

The inflammasome, and NLRP3 specifically, has also been proposed as a target for modulation by various pathogens including viruses such as DNA viruses (Amsler et al., Future Virol. (2013) 8(4), 357-370).

NLRP3 has also been implicated in the pathogenesis of many cancers (Menu et al., Clinical and Experimental Immunology 166: 1-15, 2011; and Masters Clin. Immunol. 2013). For example, several previous studies have suggested a role for IL-1$\beta$ in cancer invasiveness, growth and metastasis, and inhibition of IL-1$\beta$ with canakinumab has been shown to reduce the incidence of lung cancer and total cancer mortality in a randomised, double-blind, placebo-controlled trial (Ridker et al. Lancet, S0140-6736(17)32247-X, 2017). Inhibition of the NLRP3 inflammasome or IL-1$\beta$ has also been shown to inhibit the proliferation and migration of lung cancer cells in vitro (Wang et al., Oncol Rep., 2016; 35(4): 2053-64). A role for the NLRP3 inflammasome has been suggested in myelodysplastic syndromes (Basiorka et al., Blood, 2016 Dec. 22; 128(25): 2960-2975) and also in the carcinogenesis of various other cancers including glioma (Li et al., Am. J. Cancer Res., 2015; 5(1): 442-449), inflammation-induced tumours (Allen et al. J Exp Med. 2010; 207(5): 1045-56 and Hu et al. PNAS. 2010; 107(50): 21635-40), multiple myeloma (Li et al. Hematology 2016 21(3): 144-51), and squamous cell carcinoma of the head and neck (Huang et al., J. Exp. Clin. Cancer Res., 2017 2; 36(1): 116). Activation of the NLRP3 inflammasome has also been shown to mediate chemoresistance of tumour cells to 5-Fluorouracil (Feng et al., J. Exp. Clin. Cancer Res., 2017 21; 36(1): 81), and activation of NLRP3 inflammasome in peripheral nerve contributes to chemotherapy-induced neuropathic pain (Jia et al., Mol Pain., 2017; 13: 1-11).

NLRP3 has also been shown to be required for the efficient control of viral, bacterial, fungal, and helminth pathogen infections (Strowig et al., Nature, 481:278-286, 2012).

Accordingly, examples of diseases, disorders or conditions which may be responsive to NLRP3 inhibition and which may be treated or prevented in accordance with the fifth, sixth, seventh, eighth, ninth or tenth aspect of the present invention include:

(i) inflammation, including inflammation occurring as a result of an inflammatory disorder, e.g. an autoinflammatory disease, inflammation occurring as a symptom of a non-inflammatory disorder, inflammation occurring as a result of infection, or inflammation secondary to trauma, injury or autoimmunity;

(ii) auto-immune diseases such as acute disseminated encephalitis, Addison's disease, ankylosing spondylitis, antiphospholipid antibody syndrome (APS), anti-synthetase syndrome, aplastic anemia, autoimmune adrenalitis, autoimmune hepatitis, autoimmune oophoritis, autoimmune polyglandular failure, autoimmune thyroiditis, Coeliac disease, Crohn's disease, type 1 diabetes (T1D), Goodpasture's syndrome, Graves' disease, Guillain-Barre syndrome (GBS), Hashimoto's disease, idiopathic thrombocytopenic purpura, Kawasaki's disease, lupus erythematosus including systemic lupus erythematosus (SLE), multiple sclerosis (MS) including primary progressive multiple sclerosis (PPMS), secondary progressive multiple sclerosis (SPMS) and relapsing remitting multiple sclerosis (RRMS), myasthenia gravis, opsoclonus myoclonus syndrome (OMS), optic neuritis, Ord's thyroiditis, pemphigus, pernicious anaemia, polyarthritis, primary biliary cirrhosis, rheumatoid arthritis (RA), psoriatic arthritis, juvenile idiopathic arthritis or Still's disease, refractory gouty arthritis, Reiter's syndrome, Sjögren's syndrome, systemic sclerosis a systemic connective tissue disorder, Takayasu's arteritis, temporal arteritis, warm autoimmune hemolytic anemia, Wegener's granulomatosis, alopecia universalis, Behçet's disease, Chagas' disease, dysautonomia, endometriosis, hidradenitis suppurativa (HS), interstitial cystitis, neuromyotonia, psoriasis, sarcoidosis, scleroderma, ulcerative colitis, Schnitzler syndrome, macrophage activation syndrome, Blau syndrome, vitiligo or vulvodynia;

(iii) cancer including lung cancer, pancreatic cancer, gastric cancer, myelodysplastic syndrome, leukaemia including acute lymphocytic leukaemia (ALL) and acute myeloid leukaemia (AML), adrenal cancer, anal cancer, basal and squamous cell skin cancer, bile duct cancer, bladder cancer, bone cancer, brain and spinal cord tumours, breast cancer, cervical cancer, chronic lymphocytic leukaemia (CLL), chronic myeloid leukaemia (CML), chronic myelomonocytic leukaemia (CMML), colorectal cancer, endometrial cancer, esophagus cancer, Ewing family of tumours, eye cancer, gallbladder cancer, gastrointestinal carcinoid tumours, gastrointestinal stromal tumour (GIST), gestational trophoblastic disease, glioma, Hodgkin lymphoma, Kaposi sarcoma, kidney cancer, laryngeal and hypopharyngeal cancer, liver cancer, lung carcinoid tumour, lymphoma including cutaneous T cell lymphoma, malignant mesothelioma, melanoma skin cancer, Merkel cell skin cancer, multiple myeloma, nasal cavity and paranasal sinuses cancer, nasopharyngeal cancer, neuroblastoma, non-Hodgkin lymphoma, non-small cell lung cancer, oral cavity and oropharyngeal cancer, osteosarcoma, ovarian cancer, penile cancer, pituitary tumours, prostate cancer, retinoblastoma, rhabdomyosarcoma, salivary gland cancer, skin cancer, small cell lung cancer, small intestine cancer, soft tissue sarcoma, stomach cancer, testicular cancer, thymus cancer, thyroid cancer including anaplastic thyroid cancer, uterine sarcoma, vaginal cancer, vulvar cancer, Waldenstrom macroglobulinemia, and Wilms tumour;

(iv) infections including viral infections (e.g. from influenza virus, human immunodeficiency virus (HIV), alphavirus (such as Chikungunya and Ross River virus), flaviviruses (such as Dengue virus and Zika virus), herpes viruses (such as Epstein Barr Virus, cytomegalovirus, Varicella-zoster virus, and KSHV), poxviruses (such as vaccinia virus (Modified vaccinia virus Ankara) and Myxoma virus), adenoviruses (such as Adenovirus 5), or papillomavirus), bacterial infections (e.g. from *Staphylococcus aureus, Helicobacter pylori, Bacillus anthracis, Bordatella pertussis, Burkholderia pseudomallei, Corynebacterium diptheriae, Clostridium tetani, Clostridium botulinum, Streptococcus pneumoniae, Streptococcus pyogenes, Listeria monocytogenes, Hemophilus influenzae, Pasteurella multicida, Shigella dysenteriae, Mycobacterium tuberculosis, Mycobacterium leprae, Mycoplasma pneumoniae, Mycoplasma hominis, Neisseria meningitidis, Neisseria gonorrhoeae, Rickettsia rickettsii, Legionella pneumophila, Klebsiella pneumoniae, Pseudomonas aeruginosa, Propionibacterium acnes, Treponema pallidum, Chlamydia trachomatis, Vibrio cholerae, Salmonella typhimurium, Salmonella typhi, Borrelia burgdorferi* or *Yersinia pestis*), fungal infections (e.g. from *Candida* or *Aspergillus* species), protozoan infections (e.g. from *Plasmodium, Babesia, Giardia, Entamoeba, Leishmania* or Trypanosomes), helminth infections (e.g. from *Schistosoma*, roundworms, tapeworms or flukes) and prion infections;

(v) central nervous system diseases such as Parkinson's disease, Alzheimer's disease, dementia, motor neuron disease, Huntington's disease, cerebral malaria, brain injury from pneumococcal meningitis, intracranial aneurysms, traumatic brain injury, and amyotrophic lateral sclerosis;

(vi) metabolic diseases such as type 2 diabetes (T2D), atherosclerosis, obesity, gout, and pseudo-gout;

(vii) cardiovascular diseases such as hypertension, ischaemia, reperfusion injury including post-MI ischemic reperfusion injury, stroke including ischemic stroke, transient ischemic attack, myocardial infarction including recurrent myocardial infarction, heart failure including congestive heart failure and heart failure with preserved ejection fraction, embolism, aneurysms including abdominal aortic aneurysm, and pericarditis including Dressler's syndrome;

(viii) respiratory diseases including chronic obstructive pulmonary disorder (COPD), asthma such as allergic asthma and steroid-resistant asthma, asbestosis, silicosis, nanoparticle induced inflammation, cystic fibrosis and idiopathic pulmonary fibrosis;

(ix) liver diseases including non-alcoholic fatty liver disease (NAFLD), and non-alcoholic steatohepatitis (NASH) including advanced fibrosis stages F3 and F4, alcoholic fatty liver disease (AFLD), and alcoholic steatohepatitis (ASH);

(x) renal diseases including chronic kidney disease, oxalate nephropathy, nephrocalcinosis, glomerulonephritis, and diabetic nephropathy;

(xi) ocular diseases including those of the ocular epithelium, age-related macular degeneration (AMD) (dry and wet), uveitis, corneal infection, diabetic retinopathy, optic nerve damage, dry eye, and glaucoma;

(xii) skin diseases including dermatitis such as contact dermatitis and atopic dermatitis, contact hypersensitivity, sunburn, skin lesions, hidradenitis suppurativa (HS), other cyst-causing skin diseases, and acne conglobata;

(xiii) lymphatic conditions such as lymphangitis and Castleman's disease;

(xiv) psychological disorders such as depression and psychological stress;

(xv) graft versus host disease;

(xvi) allodynia including mechanical allodynia; and (xvii) any disease where an individual has been determined to carry a germline or somatic non-silent mutation in NLRP3.

In one embodiment, the disease, disorder or condition is selected from:
(i) inflammation;
(ii) an auto-immune disease;
(iii) cancer;
(iv) an infection;
(v) a central nervous system disease;
(vi) a metabolic disease;
(vii) a cardiovascular disease;
(viii) a respiratory disease;
(ix) a liver disease;
(x) a renal disease;
(xi) an ocular disease;
(xii) a skin disease;
(xiii) a lymphatic condition;
(xiv) a psychological disorder;
(xv) graft versus host disease; and
(xvi) any disease where an individual has been determined to carry a germline or somatic non-silent mutation in NLRP3.

In another embodiment, the disease, disorder or condition is selected from:
(i) cancer;
(ii) an infection;
(iii) a central nervous system disease;
(iv) a cardiovascular disease;
(v) a liver disease;
(vi) an ocular diseases; or
(vii) a skin disease.

More typically, the disease, disorder or condition is selected from:
(i) cancer;
(ii) an infection;
(iii) a central nervous system disease; or
(iv) a cardiovascular disease.

In one embodiment, the disease, disorder or condition is selected from:
(i) acne conglobata;
(ii) atopic dermatitis;
(iii) Alzheimer's disease;
(iv) amyotrophic lateral sclerosis;
(v) age-related macular degeneration (AMD);
(vi) anaplastic thyroid cancer;
(vii) cryopyrin-associated periodic syndromes (CAPS);
(viii) contact dermatitis;
(ix) cystic fibrosis;
(x) congestive heart failure;
(xi) chronic kidney disease;
(xii) Crohn's disease;
(xiii) familial cold autoinflammatory syndrome (FCAS);
(xiv) Huntington's disease;
(xv) heart failure;
(xvi) heart failure with preserved ejection fraction;
(xvii) ischemic reperfusion injury;
(xviii) juvenile idiopathic arthritis;
(xix) myocardial infarction;
(xx) macrophage activation syndrome;
(xxi) myelodysplastic syndrome;
(xxii) multiple myeloma;
(xxiii) motor neuron disease;
(xxiv) multiple sclerosis;
(xxv) Muckle-Wells syndrome;
(xxvi) non-alcoholic steatohepatitis (NASH);
(xxvii) neonatal-onset multisystem inflammatory disease (NOMID);
(xxviii) Parkinson's disease;
(xxix) systemic juvenile idiopathic arthritis;
(xxx) systemic lupus erythematosus;
(xxxi) traumatic brain injury;
(xxxii) transient ischemic attack; and
(xxxiii) ulcerative colitis.

In a further typical embodiment of the invention, the disease, disorder or condition is inflammation. Examples of inflammation that may be treated or prevented in accordance with the fifth, sixth, seventh, eighth, ninth or tenth aspect of the present invention include inflammatory responses occurring in connection with, or as a result of:

(i) a skin condition such as contact hypersensitivity, bullous pemphigoid, sunburn, psoriasis, atopical dermatitis, contact dermatitis, allergic contact dermatitis, seborrhoetic dermatitis, lichen planus, scleroderma, pemphigus, epidermolysis bullosa, urticaria, erythemas, or alopecia;

(ii) a joint condition such as osteoarthritis, systemic juvenile idiopathic arthritis, adult-onset Still's disease, relapsing polychondritis, rheumatoid arthritis, juvenile chronic arthritis, gout, or a seronegative spondyloarthropathy (e.g. ankylosing spondylitis, psoriatic arthritis or Reiter's disease);

(iii) a muscular condition such as polymyositis or myasthenia gravis;

(iv) a gastrointestinal tract condition such as inflammatory bowel disease (including Crohn's disease and ulcerative colitis), gastric ulcer, coeliac disease, proctitis, pancreatitis, eosinopilic gastro-enteritis, mastocytosis, antiphospholipid syndrome, or a food-related allergy which may have effects remote from the gut (e.g., migraine, rhinitis or eczema);

(v) a respiratory system condition such as chronic obstructive pulmonary disease (COPD), asthma (including bronchial, allergic, intrinsic, extrinsic or dust asthma, and particularly chronic or inveterate asthma, such as late asthma and airways hyper-responsiveness), bronchitis, rhinitis (including acute rhinitis, allergic rhinitis, atrophic rhinitis, chronic rhinitis, rhinitis caseosa, hypertrophic rhinitis, rhinitis pumlenta, rhinitis sicca, rhinitis medicamentosa, membranous rhinitis, seasonal rhinitis e.g. hay fever, and vasomotor rhinitis), sinusitis, idiopathic pulmonary fibrosis (IPF), sarcoidosis, farmer's lung, silicosis, asbestosis, adult respiratory distress syndrome, hypersensitivity pneumonitis, or idiopathic interstitial pneumonia;

(vi) a vascular condition such as atherosclerosis, Behcet's disease, vasculitides, or wegener's granulomatosis;

(vii) an autoimmune condition such as systemic lupus erythematosus, Sjogren's syndrome, systemic sclerosis, Hashimoto's thyroiditis, type I diabetes, idiopathic thrombocytopenia purpura, or Graves disease;

(viii) an ocular condition such as uveitis, allergic conjunctivitis, or vernal conjunctivitis;

(ix) a nervous condition such as multiple sclerosis or encephalomyelitis;

(x) an infection or infection-related condition, such as Acquired Immunodeficiency Syndrome (AIDS), acute or chronic bacterial infection, acute or chronic parasitic infection, acute or chronic viral infection, acute or chronic fungal infection, meningitis, hepatitis (A, B or C, or other viral hepatitis), peritonitis, pneumonia, epiglottitis, malaria, dengue hemorrhagic fever, leishmaniasis, streptococcal myositis, *Mycobacterium tuberculosis, Mycobacterium avium intracellulare, Pneumocystis carinii* pneumonia, orchitis/epidydimitis, *Legionella*, Lyme disease, influenza A, epstein-barr virus, viral encephalitis/aseptic meningitis, or pelvic inflammatory disease;

(xi) a renal condition such as mesangial proliferative glomerulonephritis, nephrotic so syndrome, nephritis, glomerular nephritis, acute renal failure, uremia, or nephritic syndrome;

(xii) a lymphatic condition such as Castleman's disease;

(xiii) a condition of, or involving, the immune system, such as hyper IgE syndrome, lepromatous leprosy, familial hemophagocytic lymphohistiocytosis, or graft versus host disease;

(xiv) a hepatic condition such as chronic active hepatitis, non-alcoholic steatohepatitis (NASH), alcohol-induced hepatitis, non-alcoholic fatty liver disease (NAFLD), alcoholic fatty liver disease (AFLD), alcoholic steatohepatitis (ASH) or primary biliary cirrhosis;

(xv) a cancer, including those cancers listed above;

(xvi) a burn, wound, trauma, haemorrhage or stroke;

(xvii) radiation exposure; and/or (xviii) obesity; and/or (xix) pain such as inflammatory hyperalgesia.

In one embodiment of the fifth, sixth, seventh, eighth, ninth or tenth aspect of the present invention, the disease, disorder or condition is an autoinflammatory disease such as cryopyrin-associated periodic syndromes (CAPS), Muckle-Wells syndrome (MWS), familial cold autoinflammatory syndrome (FCAS), familial Mediterranean fever (FMF), neonatal onset multisystem inflammatory disease (NOMID), Tumour Necrosis Factor (TNF) Receptor-Associated Periodic Syndrome (TRAPS), hyperimmunoglobulinemia D and periodic fever syndrome (HIDS), deficiency of interleukin 1 receptor antagonist (DIRA), Majeed syndrome, pyogenic arthritis, pyoderma gangrenosum and acne syndrome (PAPA), adult-onset Still's disease (AOSD), haploinsufficiency of A20 (HA20), pediatric granulomatous arthritis (PGA), PLCG2-associated antibody deficiency and immune dysregulation (PLAID), PLCG2-associated autoinflammatory, antibody deficiency and immune dysregulation (APLAID), or sideroblastic anaemia with B-cell immunodeficiency, periodic fevers and developmental delay (SIFD).

Examples of diseases, disorders or conditions which may be responsive to NLRP3 inhibition and which may be treated or prevented in accordance with the fifth, sixth, seventh, eighth, ninth or tenth aspect of the present invention are listed above. Some of these diseases, disorders or conditions are substantially or entirely mediated by NLRP3 inflammasome activity, and NLRP3-induced IL-1β and/or IL-18. As a result, such diseases, disorders or conditions may be particularly responsive to NLRP3 inhibition and may be particularly suitable for treatment or prevention in accordance with the fifth, sixth, seventh, eighth, ninth or tenth aspect of the present invention. Examples of such diseases, disorders or conditions include cryopyrin-associated periodic syndromes (CAPS), Muckle-Wells syndrome (MWS), familial cold autoinflammatory syndrome (FCAS), neonatal onset multisystem inflammatory disease (NOMID), familial Mediterranean fever (FMF), pyogenic arthritis, pyoderma gangrenosum and acne syndrome (PAPA), hyperimmunoglobulinemia D and periodic fever syndrome (HIDS), Tumour Necrosis Factor (TNF) Receptor-Associated Periodic Syndrome (TRAPS), systemic juvenile idiopathic arthritis, adult-onset Still's disease (AOSD), relapsing polychondritis, Schnitzler's syndrome, Sweet's syndrome, Behcet's disease, anti-synthetase syndrome, deficiency of interleukin 1 receptor antagonist (DIRA), and haploinsufficiency of A20 (HA20).

Moreover, some of the diseases, disorders or conditions mentioned above arise due to mutations in NLRP3, in particular, resulting in increased NLRP3 activity. As a result, such diseases, disorders or conditions may be particularly responsive to NLRP3 inhibition and may be particularly suitable for treatment or prevention in accordance with the fifth, sixth, seventh, eighth, ninth or tenth aspect of the present invention. Examples of such diseases, disorders or conditions include cryopyrin-associated periodic syndromes (CAPS), Muckle-Wells syndrome (MWS), familial cold autoinflammatory syndrome (FCAS), and neonatal onset multisystem inflammatory disease (NOMID).

An eleventh aspect of the invention provides a method of inhibiting NLRP3, the method comprising the use of a compound of the first or second aspect of the invention, or a pharmaceutically acceptable salt, solvate or prodrug of the third aspect of the invention, or a pharmaceutical composition of the fourth aspect of the invention, to inhibit NLRP3.

In one embodiment of the eleventh aspect of the present invention, the method comprises the use of a compound of the first or second aspect of the invention, or a pharmaceutically acceptable salt, solvate or prodrug of the third aspect of the invention, or a pharmaceutical composition of the fourth aspect of the invention, in combination with one or more further active agents.

In one embodiment of the eleventh aspect of the present invention, the method is performed ex vivo or in vitro, for example in order to analyse the effect on cells of NLRP3 inhibition.

In another embodiment of the eleventh aspect of the present invention, the method is performed in vivo. For example, the method may comprise the step of administering an effective amount of a compound of the first or second aspect, or a pharmaceutically acceptable salt, solvate or prodrug of the third aspect, or a pharmaceutical composition of the fourth aspect, to thereby inhibit NLRP3. In one embodiment, the method further comprises the step of co-administering an effective amount of one or more further active agents. Typically, the administration is to a subject in need thereof.

Alternately, the method of the eleventh aspect of the invention may be a method of inhibiting NLRP3 in a non-human animal subject, the method comprising the steps of administering the compound, salt, solvate, prodrug or pharmaceutical composition to the non-human animal subject and optionally subsequently mutilating or sacrificing the non-human animal subject. Typically, such a method further comprises the step of analysing one or more tissue or fluid samples from the optionally mutilated or sacrificed non-human animal subject. In one embodiment, the method further comprises the step of co-administering an effective amount of one or more further active agents.

A twelfth aspect of the invention provides a compound of the first or second aspect of the invention, or a pharmaceutically acceptable salt, solvate or prodrug of the third aspect of the invention, or a pharmaceutical composition of the fourth aspect of the invention, for use in the inhibition of NLRP3. Typically, the use comprises the administration of the compound, salt, solvate, prodrug or pharmaceutical composition to a subject. In one embodiment, the compound, salt, solvate, prodrug or pharmaceutical composition is co-administered with one or more further active agents.

A thirteenth aspect of the invention provides the use of a compound of the first or second aspect of the invention, or a pharmaceutically effective salt, solvate or prodrug of the third aspect of the invention, in the manufacture of a medicament for the inhibition of NLRP3. Typically, the inhibition comprises the administration of the compound, salt, solvate, prodrug or medicament to a subject. In one embodiment, the compound, salt, solvate, prodrug or medicament is co-administered with one or more further active agents.

In any embodiment of any of the fifth to thirteenth aspects of the present invention that comprises the use or co-administration of one or more further active agents, the one or more further active agents may comprise for example one, two or three different further active agents.

The one or more further active agents may be used or administered prior to, simultaneously with, sequentially with or subsequent to each other and/or to the compound of the first or second aspect of the invention, the pharmaceutically acceptable salt, solvate or prodrug of the third aspect of the invention, or the pharmaceutical composition of the fourth aspect of the invention. Where the one or more further active agents are administered simultaneously with the compound of the first or second aspect of the invention, or the pharmaceutically acceptable salt, solvate or prodrug of the third aspect of the invention, a pharmaceutical composition of the fourth aspect of the invention may be administered wherein the pharmaceutical composition additionally comprises the one or more further active agents.

In one embodiment of any of the fifth to thirteenth aspects of the present invention that comprises the use or co-administration of one or more further active agents, the one or more further active agents are selected from:
(i) chemotherapeutic agents;
(ii) antibodies;
(iii) alkylating agents;
(iv) anti-metabolites;
(v) anti-angiogenic agents;
(vi) plant alkaloids and/or terpenoids;
(vii) topoisomerase inhibitors;
(viii) mTOR inhibitors;
(ix) stilbenoids;
(x) STING agonists;
(xi) cancer vaccines;
(xii) immunomodulatory agents;
(xiii) antibiotics;
(xiv) anti-fungal agents;
(xv) anti-helminthic agents; and/or
(xvi) other active agents.

It will be appreciated that these general embodiments defined according to broad categories of active agents are not mutually exclusive. In this regard any particular active agent may be categorized according to more than one of the above general embodiments. A non-limiting example is urelumab which is an antibody that is an immunomodulatory agent for the treatment of cancer.

In some embodiments, the one or more chemotherapeutic agents are selected from abiraterone acetate, altretamine, amsacrine, anhydrovinblastine, auristatin, azathioprine, adriamycin, bexarotene, bicalutamide, BMS 184476, bleomycin, N,N-dimethyl-L-valyl-L-valyl-N-methyl-L-valyl-L-prolyl-L-proline-t-butylamide, cisplatin, carboplatin, carboplatin cyclophosphamide, chlorambucil, cachectin, cemadotin, cyclophosphamide, carmustine, cryptophycin, cytarabine, docetaxel, doxetaxel, doxorubicin, dacarbazine (DTIC), dactinomycin, daunorubicin, decitabine, dolastatin, etoposide, etoposide phosphate, enzalutamide (MDV3100), 5-fluorouracil, fludarabine, flutamide, gemcitabine, hydroxyurea and hydroxyureataxanes, idarubicin, ifosfamide, irinotecan, leucovorin, lonidamine, lomustine (CCNU), larotaxel (RPR109881), mechlorethamine, mercaptopurine, methotrexate, mitomycin C, mitoxantrone, melphalan, mivobulin, 3',4'-didehydro-4'-deoxy-8'-norvincaleukoblastine, nilutamide, oxaliplatin, onapristone, prednimustine, procarbazine, paclitaxel, platinum-containing anti-cancer agents, 2,3,4,5,6-pentafluoro-N-(3-fluoro-4-methoxyphenyl)benzene sulphonamide, prednimustine, procarbazine, rhizoxin, sertenef, streptozocin, stramustine phosphate, tretinoin, tasonermin, taxol, topotecan, tamoxifen, teniposide, taxane, tegafur/uracil, vincristine, vinblastine, vinorelbine, vindesine, vindesine sulfate, and/or vinflunine.

Alternatively or in addition, the one or more chemotherapeutic agents may be selected from CD59 complement fragment, fibronectin fragment, gro-beta (CXCL2), heparinases, heparin hexasaccharide fragment, human chorionic gonadotropin (hCG), interferon alpha, interferon beta, interferon gamma, interferon inducible protein (IP-10), interleukin-12, kringle 5 (plasminogen fragment), metalloproteinase inhibitors (TIMPs), 2-methoxyestradiol, placental ribonuclease inhibitor, plasminogen activator inhibitor, platelet factor-4 (PF4), prolactin 16 kD fragment, proliferin-related protein (PRP), various retinoids, tetrahydrocortisol-S, thrombospondin-1 (TSP-1), transforming growth factor-beta (TGF-β), vasculostatin, vasostatin (calreticulin fragment), and/or cytokines (including interleukins, such as interleukin-2 (IL-2), or IL-10).

In some embodiments, the one or more antibodies may comprise one or more monoclonal antibodies. In some embodiments, the one or more antibodies are selected from abciximab, adalimumab, alemtuzumab, atlizumab, basiliximab, belimumab, bevacizumab, bretuximab vedotin, canakinumab, cetuximab, ceertolizumab pegol, daclizumab, denosumab, eculizumab, efalizumab, gemtuzumab, golimumab, ibritumomab tiuxetan, infliximab, ipilimumab, muromonab-CD3, natalizumab, ofatumumab, omalizumab, palivizumab, panitumuab, ranibizumab, rituximab, tocilizumab, tositumomab, and/or trastuzumab.

In some embodiments, the one or more alkylating agents may comprise an agent capable of alkylating nucleophilic functional groups under conditions present in cells, including, for example, cancer cells. In some embodiments, the one or more alkylating agents are selected from cisplatin, carboplatin, mechlorethamine, cyclophosphamide, chlorambucil, ifosfamide and/or oxaliplatin. In some embodiments, the alkylating agent may function by impairing cell function by forming covalent bonds with amino, carboxyl, sulfhydryl, and/or phosphate groups in biologically important molecules. In some embodiments, the alkylating agent may function by modifying a cell's DNA.

In some embodiments, the one or more anti-metabolites may comprise an agent capable of affecting or preventing RNA or DNA synthesis. In some embodiments, the one or more anti-metabolites are selected from azathioprine and/or mercaptopurine.

In some embodiments, the one or more anti-angiogenic agents are selected from endostatin, angiogenin inhibitors, angiostatin, angioarrestin, angiostatin (plasminogen fragment), basement-membrane collagen-derived anti-angiogenic factors (tumstatin, canstatin, or arrestin), anti-angiogenic antithrombin III, and/or cartilage-derived inhibitor (CDI).

In some embodiments, the one or more plant alkaloids and/or terpenoids may prevent microtubule function. In some embodiments, the one or more plant alkaloids and/or terpenoids are selected from a *Vinca* alkaloid, a podophyllotoxin and/or a taxane. In some embodiments, the one or more *Vinca* alkaloids may be derived from the Madagascar periwinkle, *Catharanthus roseus* (formerly known as *Vinca rosea*), and may be selected from vincristine, vinblastine, vinorelbine and/or vindesine. In some embodiments, the one or more taxanes are selected from taxol, paclitaxel, docetaxel and/or ortataxel. In some embodiments, the one or more podophyllotoxins are selected from an etoposide and/or teniposide.

In some embodiments, the one or more topoisomerase inhibitors are selected from a type I topoisomerase inhibitor and/or a type II topoisomerase inhibitor, and may interfere with transcription and/or replication of DNA by interfering with DNA supercoiling. In some embodiments, the one or more type I topoisomerase inhibitors may comprise a camptothecin, which may be selected from exatecan, irinotecan, lurtotecan, topotecan, BNP 1350, CKD 602, DB 67 (AR67) and/or ST 1481. In some embodiments, the one or more type II topoisomerase inhibitors may comprise an epipodophyllotoxin, which may be selected from an amsacrine, etoposid, etoposide phosphate and/or teniposide.

In some embodiments, the one or more mTOR (mammalian target of rapamycin, also known as the mechanistic target of rapamycin) inhibitors are selected from rapamycin, everolimus, temsirolimus and/or deforolimus.

In some embodiments, the one or more stilbenoids are selected from resveratrol, piceatannol, pinosylvin, pterostilbene, alpha-viniferin, ampelopsin A, ampelopsin E, diptoindonesin C, diptoindonesin F, epsilon-vinferin, flexuosol A, gnetin H, hemsleyanol D, hopeaphenol, trans-diptoindonesin B, astringin, piceid and/or diptoindonesin A.

In some embodiments, the one or more STING (Stimulator of interferon genes, also known as transmembrane protein (TMEM) 173) agonists may comprise cyclic di-nucleotides, such as cAMP, cGMP, and cGAMP, and/or modified cyclic di-nucleotides that may include one or more of the following modification features: 2'-O/3'-O linkage, phosphorothioate linkage, adenine and/or guanine analogue, and/or 2'-OH modification (e.g. protection of the 2'-OH with a methyl group or replacement of the 2'-OH by —F or —N$_3$).

In some embodiments, the one or more cancer vaccines are selected from an HPV vaccine, a hepatitis B vaccine, Oncophage, and/or Provenge.

In some embodiments, the one or more immunomodulatory agents may comprise an immune checkpoint inhibitor. The immune checkpoint inhibitor may target an immune checkpoint receptor, or combination of receptors comprising, for example, CTLA-4, PD-1, PD-L1, PD-L2, T cell immunoglobulin and mucin 3 (TIM3 or HAVCR2), galectin 9, phosphatidylserine, lymphocyte activation gene 3 protein (LAG3), MHC class I, MHC class II, 4-1BB, 4-1BBL, OX40, OX40L, GITR, GITRL, CD27, CD70, TNFRSF25, TL1A, CD40, CD40L, HVEM, LIGHT, BTLA, CD160, CD80, CD244, CD48, ICOS, ICOSL, B7-H3, B7-H4, VISTA, TMIGD2, HHLA2, TMIGD2, a butyrophilin (including BTNL2), a Siglec family member, TIGIT, PVR, a killer-cell immunoglobulin-like receptor, an ILT, a leukocyte immunoglobulin-like receptor, NKG2D, NKG2A, MICA, MICB, CD28, CD86, SIRPA, CD47, VEGF, neuropilin, CD30, CD39, CD73, CXCR4, and/or CXCL12.

In some embodiments, the immune checkpoint inhibitor is selected from urelumab, PF-05082566, MEDI6469, TRX518, varlilumab, CP-870893, pembrolizumab (PD1), nivolumab (PD1), atezolizumab (formerly MPDL3280A) (PD-L1), MEDI4736 (PD-L1), avelumab (PD-L1), PDR001 (PD1), BMS-986016, MGA271, lirilumab, IPH2201, emactuzumab, INCB024360, galunisertib, ulocuplumab, BKT140, bavituximab, CC-90002, bevacizumab, and/or MNRP1685A.

In some embodiments, the one or more antibiotics are selected from amikacin, gentamicin, kanamycin, neomycin, netilmicin, tobramycin, paromomycin, streptomycin, spectinomycin, geldanamycin, herbimycin, rifaximin, loracarbef, ertapenem, doripenem, imipenem, cilastatin, meropenem, cefadroxil, cefazolin, cefalotin, cefalothin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, dalbavancin, oritavancin, clindamycin, lincomycin, daptomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin, ticarcillin, calvulanate, ampicillin, subbactam, tazobactam, ticarcillin, clavulanate, bacitracin, colistin, polymyxin B, ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethoxazole, sulfanamide, sulfasalazine, sulfisoxazole, trimethoprim-sulfamethoxazole, sulfonamideochrysoidine, demeclocycline, minocycline, oytetracycline, tetracycline, clofazimine, dapsone, dapreomycin, cycloserine, ethambutol, ethionamide, isoniazid, pyrazinamide, rifampicin, rifabutin, rifapentine, streptomycin, arsphenamine, chloramphenicol, fosfomycin, fusidic acid, metronidazole, mupirocin, platensimycin, quinupristin, dalopristin, thiamphenicol, tigecycyline, tinidazole, trimethoprim, and/or teixobactin.

In some embodiments, the one or more antibiotics may comprise one or more cytotoxic antibiotics. In some embodiments, the one or more cytotoxic antibiotics are selected from an actinomycin, an anthracenedione, an anthracycline, thalidomide, dichloroacetic acid, nicotinic acid, 2-deoxyglucose, and/or chlofazimine. In some embodiments, the one or more actinomycins are selected from actinomycin D, bacitracin, colistin (polymyxin E) and/or polymyxin B. In some embodiments, the one or more antracenediones are selected from mitoxantrone and/or pixantrone. In some embodiments, the one or more anthracyclines are selected from bleomycin, doxorubicin (Adriamycin), daunorubicin (daunomycin), epirubicin, idarubicin, mitomycin, plicamycin and/or valrubicin.

In some embodiments, the one or more anti-fungal agents are selected from bifonazole, butoconazole, clotrimazole, econazole, ketoconazole, luliconazole, miconazole, omoconazole, oxiconazole, sertaconazole, sulconazole, tioconazole, albaconazole, efinaconazole, epoziconazole, fluconazole, isavuconazole, itraconazole, posaconazole, propiconazole, ravusconazole, terconazole, voriconazole, abafungin, amorolfin, butenafine, naftifine, terbinafine, anidulafungin, caspofungin, micafungin, benzoic acid, ciclopirox, flucytosine, 5-fluorocytosine, griseofulvin, haloprogin, tolnaflate, undecylenic acid, and/or balsam of Peru.

In some embodiments, the one or more anti-helminthic agents are selected from benzimidazoles (including albendazole, mebendazole, thiabendazole, fenbendazole, triclabendazole, and flubendazole), abamectin, diethylcarbamazine, ivermectin, suramin, pyrantel pamoate, levamisole, salicylanilides (including niclosamide and oxyclozanide), and/or nitazoxanide.

In some embodiments, other active agents are selected from growth inhibitory agents, anti-inflammatory agents (including nonsteroidal anti-inflammatory agents), anti-psoriatic agents (including anthralin and its derivatives), vitamins and vitamin-derivatives (including retinoinds, and VDR receptor ligands), corticosteroids, ion channel blockers (including potassium channel blockers), immune system regulators (including cyclosporin, FK 506, and glucocorticoids), lutenizing hormone releasing hormone agonists (such as leprolidine, goserelin, triptorelin, histrelin, bicalutamide, flutamide and/or nilutamide), and/or hormones (including estrogen).

Unless stated otherwise, in any of the fifth to thirteenth aspects of the invention, the subject may be any human or other animal. Typically, the subject is a mammal, more typically a human or a domesticated mammal such as a cow, pig, lamb, sheep, goat, horse, cat, dog, rabbit, mouse etc. Most typically, the subject is a human.

Any of the medicaments employed in the present invention can be administered by oral, parenteral (including intravenous, subcutaneous, intramuscular, intradermal, intratracheal, intraperitoneal, intraarticular, intracranial and epidural), airway (aerosol), rectal, vaginal, ocular or topical (including transdermal, buccal, mucosal, sublingual and topical ocular) administration.

Typically, the mode of administration selected is that most appropriate to the disorder, disease or condition to be treated or prevented. Where one or more further active agents are administered, the mode of administration may be the same as or different to the mode of administration of the compound, salt, solvate, prodrug or pharmaceutical composition of the invention.

For oral administration, the compounds, salts, solvates or prodrugs of the present invention will generally be provided in the form of tablets, capsules, hard or soft gelatine capsules, caplets, troches or lozenges, as a powder or granules, or as an aqueous solution, suspension or dispersion.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose. Corn starch and alginic acid are suitable disintegrating agents. Binding agents may include starch and gelatine. The lubricating agent, if present, may be magnesium stearate, stearic acid or talc. If desired, the tablets may be coated with a material, such as glyceryl monostearate or glyceryl distearate, to delay absorption in the gastrointestinal tract. Tablets may also be effervescent and/or dissolving tablets.

Capsules for oral use include hard gelatine capsules in which the active ingredient is mixed with a solid diluent, and soft gelatine capsules wherein the active ingredient is mixed with water or an oil such as peanut oil, liquid paraffin or olive oil.

Powders or granules for oral use may be provided in sachets or tubs. Aqueous solutions, suspensions or dispersions may be prepared by the addition of water to powders, granules or tablets.

Any form suitable for oral administration may optionally include sweetening agents such as sugar, flavouring agents, colouring agents and/or preservatives.

Formulations for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

For parenteral use, the compounds, salts, solvates or prodrugs of the present invention will generally be provided in a sterile aqueous solution or suspension, buffered to an appropriate pH and isotonicity. Suitable aqueous vehicles include Ringer's solution and isotonic sodium chloride or glucose. Aqueous suspensions according to the invention may include suspending agents such as cellulose derivatives, sodium alginate, polyvinylpyrrolidone and gum tragacanth, and a wetting agent such as lecithin. Suitable preservatives for aqueous suspensions include ethyl and n-propyl p-hydroxybenzoate. The compounds of the invention may also be presented as liposome formulations.

For ocular administration, the compounds, salts, solvates or prodrugs of the invention will generally be provided in a form suitable for topical administration, e.g. as eye drops. Suitable forms may include ophthalmic solutions, gel-forming solutions, sterile powders for reconstitution, ophthalmic suspensions, ophthalmic ointments, ophthalmic emulsions, ophthalmic gels and ocular inserts. Alternatively, the compounds, salts, solvates or prodrugs of the invention may be provided in a form suitable for other types of ocular administration, for example as intraocular preparations (including as irrigating solutions, as intraocular, intravitreal or juxtascleral injection formulations, or as intravitreal implants), as packs or corneal shields, as intracameral, subconjunctival or retrobulbar injection formulations, or as iontophoresis formulations.

For transdermal and other topical administration, the compounds, salts, solvates or prodrugs of the invention will generally be provided in the form of ointments, cataplasms (poultices), pastes, powders, dressings, creams, plasters or patches.

Suitable suspensions and solutions can be used in inhalers for airway (aerosol) administration.

The dose of the compounds, salts, solvates or prodrugs of the present invention will, of course, vary with the disorder, disease or condition to be treated or prevented. In general, a suitable dose will be in the range of 0.01 to 500 mg per kilogram body weight of the recipient per day. The desired dose may be presented at an appropriate interval such as once every other day, once a day, twice a day, three times a day or four times a day. The desired dose may be administered in unit dosage form, for example, containing 1 mg to 50 g of active ingredient per unit dosage form.

For the avoidance of doubt, insofar as is practicable any embodiment of a given aspect of the present invention may occur in combination with any other embodiment of the same aspect of the present invention. In addition, insofar as is practicable it is to be understood that any preferred, typical or optional embodiment of any aspect of the present invention should also be considered as a preferred, typical or optional embodiment of any other aspect of the present invention.

By way of example, combinations of aspects and embodiments that are typical of the present invention include the following.

In a first combination, a compound of the first aspect of the invention is provided wherein:
Q is O;
ring A is monocyclic;
$R^2$ has the formula:

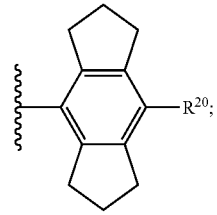

and
$R^{20}$ is a halo, —$NO_2$, —CN, or a saturated hydrocarbyl group, wherein the saturated hydrocarbyl group may be straight-chained or branched, wherein the saturated hydrocarbyl group may optionally be substituted with one or more groups independently selected from halo, —CN, —OH, —$NH_2$ and oxo (=O), and wherein the saturated hydrocarbyl group may optionally include one or two heteroatoms N or O in its carbon skeleton, provided that $R^{20}$ contains from 1 to 8 atoms other than hydrogen.

In a second combination, a compound of the first aspect of the invention is provided wherein:
Q is O;
ring A is monocyclic; and
$R^2$ is a 5- or 6-membered heteroaryl group, wherein the heteroaryl group is substituted at the α and α' positions, and wherein $R^2$ may optionally be further substituted.

In a third combination, a compound of the first aspect of the invention is provided wherein the compound is a compound of formula (Ia), and wherein:
Q is O;
$R^X$ is selected from a halo, $C_1$-$C_6$ alkyl, $C_1$-$C_6$ haloalkyl $C_3$-$C_6$ cycloalkyl or $C_3$-$C_6$ halocycloalkyl group;
$R^Y$ is selected from a $C_1$-$C_6$ alkyl or a $C_3$-$C_6$ cycloalkyl group, wherein the $C_1$-$C_6$ alkyl or $C_3$-$C_6$ cycloalkyl group may optionally be substituted with one or more substituents independently selected from halo, —CN and —OH;
$R^2$ has the formula:

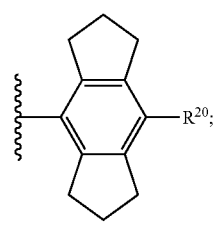

and
$R^{20}$ is a halo, —$NO_2$, —CN, —$COOR^{21}$, —$CONH_2$, —$CONHR^{21}$ or —$CON(R^{21})_2$ group, wherein each $R^{21}$ is independently selected from a $C_1$-$C_4$ alkyl group, and wherein any $R^{21}$ may optionally be substituted with one or more halo groups.

In a fourth combination, a compound of the first aspect of the invention is provided wherein the compound is a compound of formula (Ia), and wherein:
Q is O;
$R^X$ is selected from a halo, $C_1$-$C_6$ alkyl, $C_1$-$C_6$ haloalkyl $C_3$-$C_6$ cycloalkyl or $C_3$-$C_6$ halocycloalkyl group;
$R^Y$ is selected from a $C_1$-$C_6$ alkyl or a $C_3$-$C_6$ cycloalkyl group, wherein the $C_1$-$C_6$ alkyl or $C_3$-$C_6$ cycloalkyl group may optionally be substituted with one or more substituents independently selected from halo, —CN and —OH;
$R^2$ has a formula selected from:

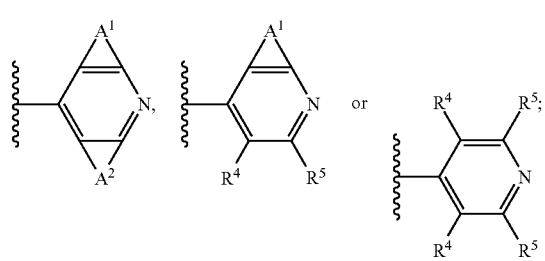

$A^1$ and $A^2$ are each independently selected from a straight chain alkylene group, wherein one or two carbon atoms in the backbone of the alkylene group may optionally be replaced by one or two heteroatoms independently selected from nitrogen and oxygen, wherein the alkylene group may optionally be substituted with one or more halo, —OH, —CN, —O($C_1$-$C_4$ alkyl) or —O($C_1$-$C_4$ haloalkyl) groups, and wherein any ring containing $A^1$ or $A^2$ is a 5- or 6-membered ring;
each $R^4$ is independently selected from a $C_1$-$C_6$ alkyl or $C_3$-$C_6$ cycloalkyl group, wherein the $C_1$-$C_6$ alkyl or $C_3$-$C_6$ cycloalkyl group may optionally be substituted with one or more halo, —OH, —CN, —O($C_1$-$C_4$ alkyl) or —O($C_1$-$C_4$ haloalkyl) groups; and
each $R^5$ is independently selected from hydrogen or a halo group.

EXAMPLES—COMPOUND SYNTHESIS

All solvents, reagents and compounds were purchased and used without further purification unless stated otherwise.

Abbreviations

2-MeTHF 2-methyltetrahydrofuran
$Ac_2O$ acetic anhydride
AcOH acetic acid
aq aqueous
Boc tert-butyloxycarbonyl
br broad
Cbz carboxybenzyl
CDI 1,1-carbonyl-diimidazole
conc concentrated
d doublet
DABCO 1,4-diazabicyclo[2.2.2]octane
DCE 1,2-dichloroethane, also called ethylene dichloride
DCM dichloromethane
DIPEA N,N-diisopropylethylamine, also called Hunig's base
DMA dimethylacetamide DMAP 4-dimethylaminopyridine, also called N,N-dimethylpyridin-4-amine
DME dimethoxyethane
DMF N,N-dimethylformamide
DMSO dimethyl sulfoxide
eq or equiv equivalent
(ES+) electrospray ionization, positive mode
Et ethyl
EtOAc ethyl acetate
EtOH ethanol
h hour(s)
HATU 1-[bis(dimethylamino)methylene]-1H-1,2,3-triazolo[4,5-b]pyridinium 3-oxid hexafluorophosphate
HPLC high performance liquid chromatography
LC liquid chromatography
m multiplet
m-CPBA 3-chloroperoxybenzoic acid
Me methyl
MeCN acetonitrile
MeOH methanol
(M+H)+ protonated molecular ion
MHz megahertz
min minute(s)
MS mass spectrometry
Ms mesyl, also called methanesulfonyl
MsCl mesyl chloride, also called methanesulfonyl chloride
MTBE methyl tert-butyl ether, also called tert-butyl methyl ether
m/z mass-to-charge ratio
NaOtBu sodium tert-butoxide
NBS 1-bromopyrrolidine-2,5-dione, also called N-bromosuccinimide
NCS 1-chloropyrrolidine-2,5-dione, also called N-chlorosuccinimide
NMP N-methylpyrrolidine
NMR nuclear magnetic resonance (spectroscopy)
Pd(dba)$_3$ tris(dibenzylideneacetone) dipalladium(0)
Pd(dppf)Cl$_2$ [1,1'-bis(diphenylphosphino)ferrocene] dichloropalladium(II)
PE petroleum ether
Ph phenyl
PMB p-methoxybenzyl, also called 4-methoxybenzyl
prep-HPLC preparative high performance liquid chromatography
prep-TLC preparative thin layer chromatography
PTSA p-toluenesulfonic acid
q quartet
RP reversed phase
RT room temperature
s singlet
Sept septuplet
sat saturated
SCX solid supported cation exchange (resin)
t triplet
T3P propylphosphonic anhydride
TBME tert-butyl methyl ether, also called methyl tert-butyl ether
TEA triethylamine
TFA 2,2,2-trifluoroacetic acid
THF tetrahydrofuran
TLC thin layer chromatography
wt % weight percent or percent by weight Experimental Methods Nuclear Magnetic Resonance NMR spectra were recorded at 300, 400 or 500 MHz. Spectra were measured at 298 K, unless indicated otherwise, and were referenced relative to the solvent resonance. The chemical shifts are reported in parts per million. Spectra were recorded using one of the following machines:

a Bruker Avance III spectrometer at 400 MHz fitted with a BBO 5 mm liquid probe, a Bruker 400 MHz spectrometers using ICON-NMR, under TopSpin program control, a Bruker Avance III HD spectrometer at 500 MHz, equipped with a Bruker 5 mm SmartProbe™, an Agilent VNMRS 300 instrument fitted with a 7.05 Tesla magnet from Oxford instruments, indirect detection probe and direct drive console including PFG module, or an Agilent MercuryPlus 300 instrument fitted with a 7.05 Tesla magnet from Oxford instruments, 4 nuclei auto-switchable probe and Mercury plus console.

LC-MS

LC-MS Methods: Using SHIMADZU LCMS-2020, Agilent 1200 LC/G1956A MSD and Agilent 1200\G6110A, Agilent 1200 LC & Agilent 6110 MSD. Mobile Phase: A: 0.025% NH$_3$.H$_2$O in water (v/v); B: acetonitrile. Column: Kinetex EVO C18 2.1×30 mm, 5 µm.

Reversed Phase HPLC Conditions for the LCMS Analytical Methods

Methods 1a and 1b: Waters Xselect CSH C18 XP column (4.6×30 mm, 2.5 µm) at 40° C.; flow rate 2.5-4.5 mL min$^{-1}$ eluted with a H$_2$O-MeCN gradient containing either 0.1% v/v formic acid (Method 1a) or 10 mM NH$_4$HCO$_3$ in water (Method 1b) over 4 min employing UV detection at 254 nm. Gradient information: 0-3.00 min, ramped from 95% water-5% acetonitrile to 5% water-95% acetonitrile; 3.00-3.01 min, held at 5% water-95% acetonitrile, flow rate increased to 4.5 mL min$^{-1}$; 3.01-3.50 min, held at 5% water-95% acetonitrile; 3.50-3.60 min, returned to 95% water-5% acetonitrile, flow rate reduced to 3.50 mL min$^{-1}$; 3.60-3.90 min, held at 95% water-5% acetonitrile; 3.90-4.00 min, held at 95% water-5% acetonitrile, flow rate reduced to 2.5 mL min$^{-1}$.

Method 1c: Agilent 1290 series with UV detector and HP 6130 MSD mass detector using Waters XBridge BEH C18 XP column (2.1×50 mm, 2.5 µm) at 35° C.; flow rate 0.6 mL/min; mobile phase A: ammonium acetate (10 mM); water/MeOH/acetonitrile (900:60:40); mobile phase B: ammonium acetate (10 mM); water/MeOH/acetonitrile (100:540:360); over 4 min employing UV detection at 215 and 238 nm. Gradient information: 0-0.5 min, held at 80% A-20% B; 0.5-2.0 min, ramped from 80% A-20% B to 100% B.

Reversed Phase HPLC Conditions for the UPLC Analytical Methods

Methods 2a and 2b: Waters BEH C18 (2.1×30 mm, 1.7 µm) at 40° C.; flow rate 0.77 mL min$^{-1}$ eluted with a H$_2$O-MeCN gradient containing either 0.1% v/v formic acid (Method 2a) or 10 mM NH$_4$HCO$_3$ in water (Method 2b) over 3 min employing UV detection at 254 nm. Gradient information: 0-0.11 min, held at 95% water-5% acetonitrile, flow rate 0.77 mL min$^{-1}$; 0.11-2.15 min, ramped from 95% water-5% acetonitrile to 5% water-95% acetonitrile; 2.15-2.49 min, held at 5% water-95% acetonitrile, flow rate 0.77 mL min$^{-1}$; 2.49-2.56 min, returned to 95% water-5% acetonitrile; 2.56-3.00 min, held at 95% water-5% acetonitrile, flow rate reduced to 0.77 mL min$^{-1}$.

Preparative Reversed Phase HPLC General Methods

Method 1 (acidic preparation): Waters X-Select CSH column C18, 5 µm (19×50 mm), flow rate 28 mL min$^{-1}$ eluting with a H$_2$O-MeCN gradient containing 0.1% v/v formic acid over 6.5 min using UV detection at 254 nm. Gradient information: 0.0-0.2 min, 20% MeCN; 0.2-5.5 min, ramped from 20% MeCN to 40% MeCN; 5.5-5.6 min, ramped from 40% MeCN to 95% MeCN; 5.6-6.5 min, held at 95% MeCN.

Method 2 (basic preparation): Waters X-Bridge Prep column C18, 5 μm (19×50 mm), flow rate 28 mL min⁻¹ eluting with a 10 mM NH₄HCO₃-MeCN gradient over 6.5 min using UV detection at 254 nm. Gradient information: 0.0-0.2 min, 10% MeCN; 0.2-5.5 min, ramped from 10% MeCN to 40% MeCN; 5.5-5.6 min, ramped from 40% MeCN to 95% MeCN; 5.6-6.5 min, held at 95% MeCN.

Method 3: Phenomenex Gemini column, 10 μm (150×25 mm), flow rate=25 mL/min eluting with a water-acetonitrile gradient containing 0.04% NH₃ at pH 10 over 9 minutes using UV detection at 220 and 254 nm. Gradient information: 0-9 minutes, ramped from 8% to 35% acetonitrile; 9-9.2 minutes, ramped from 35% to 100% acetonitrile; 9.2-15.2 minutes, held at 100% acetonitrile.

Method 4: Revelis C18 reversed-phase 12 g cartridge [carbon loading 18%; surface area 568 m²/g; pore diameter 65 Angstrom; pH (5% slurry) 5.1; average particle size 40 μm], flow rate=30 mL/min eluting with a water-methanol gradient over 35 minutes using UV detection at 215, 235, 254 and 280 nm. Gradient information: 0-5 minutes, held at 0% methanol; 5-30 minutes, ramped from 0% to 70% methanol; 30-30.1 minutes, ramped from 70% to 100% methanol; 30.1-35 minutes, held at 100% methanol.

Synthesis of Intermediates

Intermediate A1: 8-Isocyanato-1,2,3,5,6,7-hexahydro-s-indacene-4-carbonitrile

Step A:
8-Bromo-1,2,3,5,6,7-hexahydro-s-indacen-4-amine

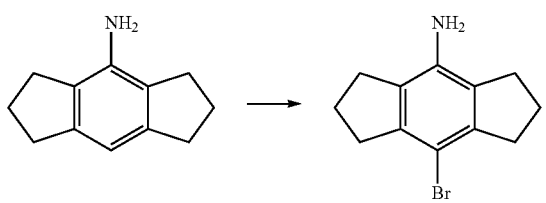 [SMILES: Nc1c2c(cc3c1CCC3)CCC2 ; Nc1c2c(c(Br)c3c1CCC3)CCC2]

To a solution of 1,2,3,5,6,7-hexahydro-s-indacen-4-amine (0.5 g, 2.89 mmol) in DCM (10 mL) at 0° C. was added NBS (0.514 g, 2.89 mmol). The solution was gradually warmed to room temperature and stirred for 12 hours. The reaction mixture was diluted with aq Na₂S₂O₃ (25 mL) and extracted with DCM (2×20 ml). The combined organic extracts were washed with water (10 mL) and saturated brine (20 mL), dried (MgSO₄), filtered and concentrated in vacuo to afford a brown solid. The crude product was purified by chromatography on silica gel (12 g column, 0-10% EtOAc/isohexane) to afford the title compound (579 mg, 79%) as a brown solid.

¹H NMR (DMSO-d6) δ 4.71 (s, 2H), 2.80-2.63 (m, 8H), 2.08-1.91 (m, 4H).

LCMS; m/z 252/254 (M+H)⁺ (ES⁺).

Step B: 8-Amino-1,2,3,5,6,7-hexahydro-s-indacene-4-carbonitrile

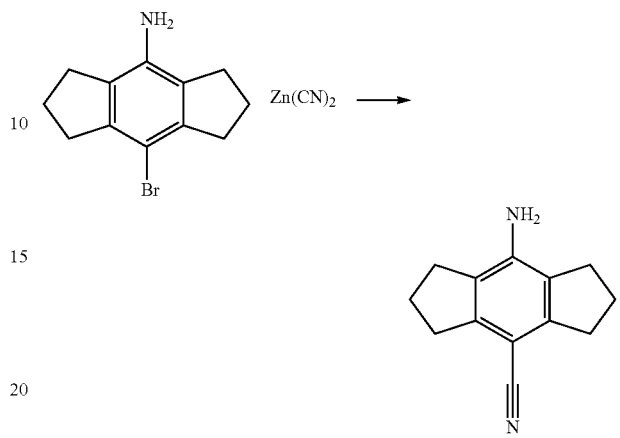

A solution of 8-bromo-1,2,3,5,6,7-hexahydro-s-indacen-4-amine (579 mg, 2.296 mmol) and dicyanozinc (283 mg, 2.411 mmol) in DMA (10 mL) was degassed for 10 minutes with nitrogen. Then Pd(PPh₃)₄ (265 mg, 0.230 mmol) was added and the reaction mixture was heated to 100° C. under N₂ for 18 hours. The reaction mixture was allowed to cool to room temperature and then filtered over Celite® eluting with EtOAc (30 mL). The filtrate was washed with sat aq NaHCO₃ (2×10 mL), water (2×10 mL) and brine (2×10 mL), dried over Na₂SO₄, filtered and concentrated under reduced pressure. The residue was purified by chromatography on silica gel (24 g column 0-40% EtOAc/isohexane) to afford the title compound (96 mg, 20%) as colourless solid.

¹H NMR (DMSO-d6) δ 5.68 (s, 2H), 2.85 (t, J=7.5 Hz, 4H), 2.64 (t, J=7.4 Hz, 4H), 2.15-1.96 (m, 4H).

LCMS; m/z 199.1 (M+H)⁺ (ES⁺).

Step C: 8-Isocyanato-1,2,3,5,6,7-hexahydro-s-indacene-4-carbonitrile

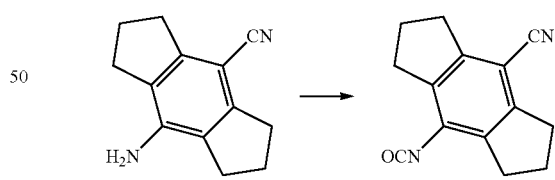

Triphosgene (95 mg, 0.320 mmol) was added to a mixture of 8-amino-1,2,3,5,6,7-hexahydro-s-indacene-4-carbonitrile (96 mg, 0.484 mmol) and triethylamine (0.202 ml, 1.453 mmol) in THF (5.5 ml) and heated at reflux for 2 hours. The mixture was concentrated in vacuo and dried azeotropically with toluene (3×1 ml). The residue was taken up in toluene and filtered through a plug of silica, washing with toluene, and the filtrate was concentrated to afford the title compound (101 mg, 87%) as a colourless solid. A sample was quenched with morpholine in DMSO and was analysed.

LCMS m/z 312.1 (M+H)⁺ (ES⁺).

Intermediate A2: 4-Bromo-8-isocyanato-1,2,3,5,6,7-hexahydro-s-indacene

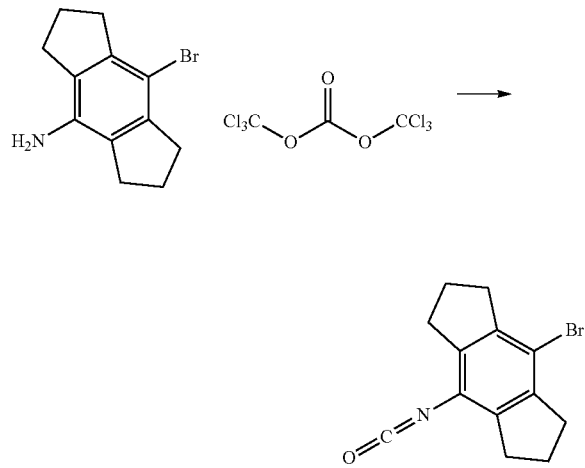

Prepared according to the general procedure of 8-isocyanato-1,2,3,5,6,7-hexahydro-s-indacene-4-carbonitrile (Intermediate A1) from 8-bromo-1,2,3,5,6,7-hexahydro-s-indacen-4-amine (Intermediate A1, Step A) to afford the title compound (197 mg, 97%) as a colourless solid. A sample was quenched with morpholine in DMSO and was analysed.

LCMS m/z 365/367 (M+H)$^+$ (ES$^+$).

Intermediate P1: 5-(2-Hydroxypropan-2-yl)-1-methyl-1H-pyrazole-3-sulfonamide

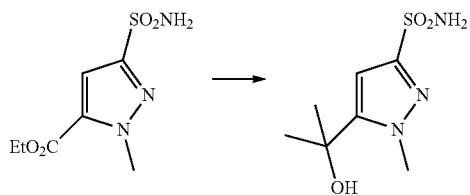

MeMgCl (3 M in THF, 10.72 mL, 32.2 mmol) was added dropwise over 30 minutes to a stirred ice cold solution of ethyl 1-methyl-3-sulfamoyl-1H-pyrazole-5-carboxylate (1.5 g, 6.43 mmol) in THF (50 mL). Further THF (20 mL) was added to improve stirring, followed by the dropwise addition of further MeMgCl (3 M in THF, 2.14 mL, 6.43 mmol). The reaction was allowed to warm to room temperature and stirred for a further 20 hours. Then the reaction was cooled to 0° C., quenched with sat aq NH$_4$Cl (30 mL) and extracted with EtOAc (4×30 mL). The combined organic extracts were washed with brine (30 mL), dried (MgSO$_4$), filtered and evaporated in vacuo. The residue was purified by chromatography on silica gel (220 g column, 0-20% EtOAc/iso-hexane) to afford the title compound (1.1 g, 77%) as a colourless gum.

$^1$H NMR (DMSO-d$_6$) δ 7.32 (s, 2H), 6.40 (s, 1H), 5.46 (s, 1H), 4.01 (s, 3H), 1.50 (s, 6H).

LCMS m/z 220.0 (M+H)$^+$ (ES$^+$).

PREPARATION OF EXAMPLES

Example 1: N-((8-Cyano-1,2,3,5,6,7-hexahydro-s-indacen-4-yl)carbamoyl)-5-(2-hydroxypropan-2-yl)-1-methyl-1H-pyrazole-3-sulfonamide

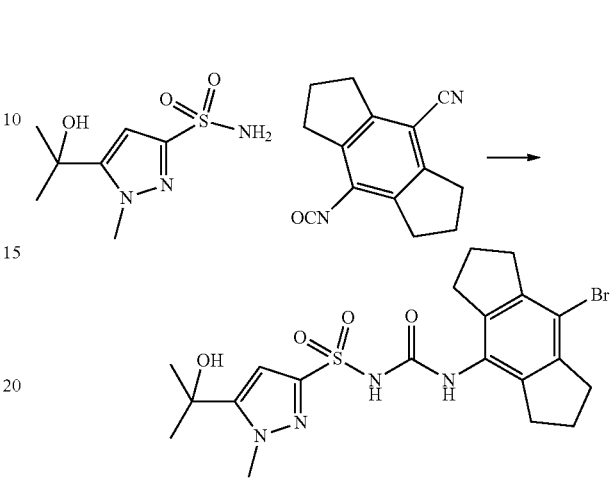

5-(2-Hydroxypropan-2-yl)-1-methyl-1H-pyrazole-3-sulfonamide (Intermediate P1) (33 mg, 0.151 mmol) was dissolved in THF (2 mL) and 60% wt sodium hydride (7 mg, 0.175 mmol) was added and stirred at room temperature for 30 minutes to give a white suspension. 8-Isocyanato-1,2,3,5,6,7-hexahydro-s-indacene-4-carbonitrile (Intermediate A1) (37 mg, 0.165 mmol) in THF (2 mL) was added and stirred at room temperature for 4 hours. The reaction mixture was diluted with water (2 mL), concentrated, then redissolved in water (1.5 mL) washed with TBME (2×3 mL) and the aqueous phase was filtered through a syringe filter. The crude product was purified by chromatography on RP Flash C18 (12 g column, 5-50% MeCN/10 mM ammonium bicarbonate) to afford the title compound (40 mg, 58%) as a colourless solid.

$^1$H NMR (DMSO-d6) δ 10.99 (s, 1H), 8.43 (s, 1H), 6.57 (s, 1H), 5.53 (s, 1H), 4.04 (s, 3H), 2.96 (t, J=7.5 Hz, 4H), 2.70 (t, J=7.4 Hz, 4H), 2.06 (p, J=7.3 Hz, 4H), 1.50 (s, 6H).

LCMS; m/z 444.5 (M+H)$^+$ (ES$^+$).

Example 2: N-((8-Bromo-1,2,3,5,6,7-hexahydro-s-indacen-4-yl)carbamoyl)-5-(2-hydroxypropan-2-yl)-1-methyl-1H-pyrazole-3-sulfonamide

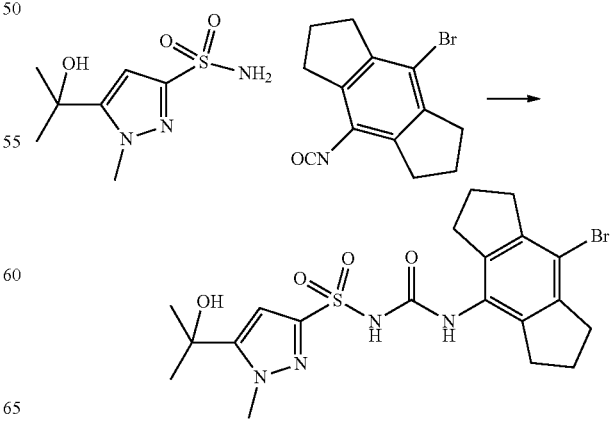

5-(2-Hydroxypropan-2-yl)-1-methyl-1H-pyrazole-3-sulfonamide (Intermediate P1) (44 mg, 0.201 mmol) was dissolved in THF (2 ml) and sodium hydride (10 mg, 0.250 mmol) was added and stirred at room temperature for 30 minutes to give a white suspension. 4-Bromo-8-isocyanato-1,2,3,5,6,7-hexahydro-s-indacene (Intermediate A2) (62 mg, 0.223 mmol) in THF (2 ml, 24.66 mmol) was added and stirred at room temperature for 2 hours. The reaction mixture was diluted with water (2 ml) and then concentrated and the crude product was purified by chromatography on RP Flash C18 (12 g column, 5-40% MeCN/10 mM ammonium bicarbonate) to afford the title compound (53 mg, 46%) as a colourless solid.

$^1$H NMR (DMSO-d6) δ 10.85 (s, 1H), 8.08 (s, 1H), 6.55 (s, 1H), 5.50 (s, 1H), 4.03 (s, 3H), 2.82 (t, J=7.4 Hz, 4H), 2.75 (t, J=7.3 Hz, 4H), 2.06-1.91 (m, 4H), 1.49 (s, 6H).

LCMS; m/z 497/499 (M+H)$^+$ (ES$^+$).

Other compounds of the invention may be synthesised by methods analogous to those outlined above.

Examples—Biological Studies

NLRP3 and Pyroptosis

It is well established that the activation of NLRP3 leads to cell pyroptosis and this feature plays an important part in the manifestation of clinical disease (Yan-gang Liu et al., Cell Death & Disease, 2017, 8(2), e2579; Alexander Wree et al., Hepatology, 2014, 59(3), 898-910; Alex Baldwin et al., Journal of Medicinal Chemistry, 2016, 59(5), 1691-1710; Ema Ozaki et al., Journal of Inflammation Research, 2015, 8, 15-27; Zhen Xie & Gang Zhao, Neuroimmunology Neuroinflammation, 2014, 1(2), 60-65; Mattia Cocco et al., Journal of Medicinal Chemistry, 2014, 57(24), 10366-10382; T. Satoh et al., Cell Death & Disease, 2013, 4, e644). Therefore, it is anticipated that inhibitors of NLRP3 will block pyroptosis, as well as the release of pro-inflammatory cytokines (e.g. IL-1β) from the cell.

THP-1 Cells: Culture and Preparation

THP-1 cells (ATCC #TIB-202) were grown in RPMI containing L-glutamine (Gibco #11835) supplemented with 1 mM sodium pyruvate (Sigma #S8636) and penicillin (100 units/ml)/streptomycin (0.1 mg/ml) (Sigma #P4333) in 10% Fetal Bovine Serum (FBS) (Sigma #F0804). The cells were routinely passaged and grown to confluency (~10$^6$ cells/ml). On the day of the experiment, THP-1 cells were harvested and resuspended into RPMI medium (without FBS). The cells were then counted and viability (>90%) checked by Trypan blue (Sigma #T8154). Appropriate dilutions were made to give a concentration of 625,000 cells/ml. To this diluted cell solution was added LPS (Sigma #L4524) to give a 1 μg/ml Final Assay Concentration (FAC). 40 μl of the final preparation was aliquoted into each well of a 96-well plate. The plate thus prepared was used for compound screening.

THP-1 Cells Pyroptosis Assay

The following method step-by-step assay was followed for compound screening.

1. Seed THP-1 cells (25,000 cells/well) containing 1.0 μg/ml LPS in 40 μl of RPMI medium (without FBS) in 96-well, black walled, clear bottom cell culture plates coated with poly-D-lysine (VWR #734-0317)
2. Add 5 μl compound (8 points half-log dilution, with 10 μM top dose) or vehicle (DMSO 0.1% FAC) to the appropriate wells
3. Incubate for 3 hrs at 37° C. in 5% CO$_2$
4. Add 5 μl nigericin (Sigma #N7143) (FAC 5 μM) to all wells
5. Incubate for 1 hr at 37° C. and 5% CO$_2$
6. At the end of the incubation period, spin plates at 300×g for 3 mins and remove supernatant
7. Then add 50 μl of resazurin (Sigma #R7017) (FAC 100 μM resazurin in RPMI medium without FBS) and incubate plates for a further 1-2 hrs at 37° C. and 5% CO$_2$
8. Plates were read in an Envision reader at Ex 560 nm and Em 590 nm
9. IC$_{50}$ data is fitted to a non-linear regression equation (log inhibitor vs response-variable slope 4-parameters)

96-Well Plate Map

|   | 1 | 2 | 3 | 4 | 5 | 6 | 7 | 8 | 9 | 10 | 11 | 12 |
|---|---|---|---|---|---|---|---|---|---|---|---|---|
| A | High | Comp 1 | Comp 2 | Comp 3 | Comp 4 | Comp 5 | Comp 6 | Comp 7 | Comp 8 | Comp 9 | Comp 10 | Low |
| B | High | Comp 1 | Comp 2 | Comp 3 | Comp 4 | Comp 5 | Comp 6 | Comp 7 | Comp 8 | Comp 9 | Comp 10 | Low |
| C | High | Comp 1 | Comp 2 | Comp 3 | Comp 4 | Comp 5 | Comp 6 | Comp 7 | Comp 8 | Comp 9 | Comp 10 | Low |
| D | High | Comp 1 | Comp 2 | Comp 3 | Comp 4 | Comp 5 | Comp 6 | Comp 7 | Comp 8 | Comp 9 | Comp 10 | Low |
| E | High | Comp 1 | Comp 2 | Comp 3 | Comp 4 | Comp 5 | Comp 6 | Comp 7 | Comp 8 | Comp 9 | Comp 10 | Low |
| F | High | Comp 1 | Comp 2 | Comp 3 | Comp 4 | Comp 5 | Comp 6 | Comp 7 | Comp 8 | Comp 9 | Comp 10 | Low |
| G | High | Comp 1 | Comp 2 | Comp 3 | Comp 4 | Comp 5 | Comp 6 | Comp 7 | Comp 8 | Comp 9 | Comp 10 | Low |
| H | High | Comp 1 | Comp 2 | Comp 3 | Comp 4 | Comp 5 | Comp 6 | Comp 7 | Comp 8 | Comp 9 | Comp 10 | Low |

High MCC950 (10 uM)
Low Drug free control
Compound 8-point half-log dilution

The results of the pyroptosis assay performed are summarised in Table 1 below as THP IC$_{50}$.

Human Whole Blood IL1β Release Assay

For systemic delivery, the ability to inhibit NLRP3 when the compounds are present within the bloodstream is of great importance. For this reason, the NLRP3 inhibitory activity of a number of compounds in human whole blood was investigated in accordance with the following protocol.

Human whole blood in Li-heparin tubes was obtained from healthy donors from a volunteer donor panel.

1. Plate out 80 μl of whole blood containing 1 μg/ml of LPS in 96-well, clear bottom cell culture plate (Corning #3585)
2. Add 10 μl compound (8 points half-log dilution with IoM top dose) or vehicle (DMSO 0.1% FAC) to the appropriate wells
3. Incubate for 3 hrs at 37° C., 5% CO$_2$
4. Add 10 μl nigericin (Sigma #N7143) (10 μM FAC) to all wells
5. Incubate for 1 hr at 37° C., 5% CO$_2$
6. At the end of the incubation period, spin plates at 300×g for 5 mins to pellet cells and remove 20 μl of supernatant and add to 96-well v-bottom plates for IL-1β analysis (note: these plates containing the supernatants can be stored at −80° C. to be analysed at a later date)
7. IL-1β was measured according to the manufacturer protocol (Perkin Elmer-AlphaLisa IL-1 Kit AL220F-5000)

8. IC$_{50}$ data is fitted to a non-linear regression equation (log inhibitor vs response-variable slope 4-parameters)

The results of the human whole blood assay are summarised in Table 1 below as HWB IC$_{50}$.

TABLE 1

NLRP$_3$ inhibitory activity

| Example No | Structure | THP IC$_{50}$ | HWB IC$_{50}$ |
|---|---|---|---|
| 1 | 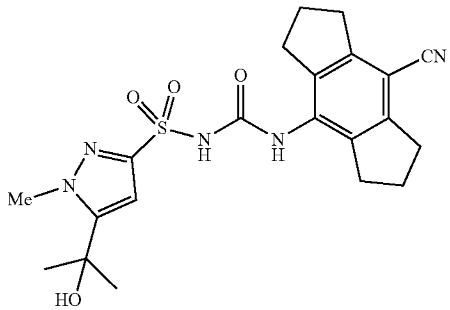 [SMILES: Cn1nc(S(=O)(=O)NC(=O)Nc2c3c(c(C#N)c4c2CCC4)CCC3)cc1C(C)(C)O] | +++ | ND |
| 2 | 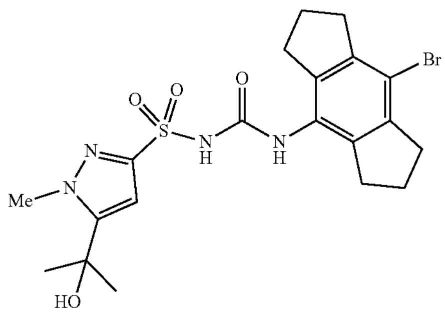 [SMILES: Cn1nc(S(=O)(=O)NC(=O)Nc2c3c(c(Br)c4c2CCC4)CCC3)cc1C(C)(C)O] | ++++ | + |

[THP IC$_{50}$ (≤0.16 μM = ++++, ≤0.64 μM = +++, ≤2.56 μM = ++, ≤10 μM = +, not determined = ND)].

As is evident from the results presented in Table 1, surprisingly in spite of the structural differences versus the prior art compounds, the compounds of the invention show high levels of NLRP3 inhibitory activity in the pyroptosis assay and in the human whole blood assay.

It will be understood that the present invention has been described above by way of example only. The examples are not intended to limit the scope of the invention. Various modifications and embodiments can be made without departing from the scope and spirit of the invention, which is defined by the following claims only.

The invention claimed is:
1. A compound of formula (I):

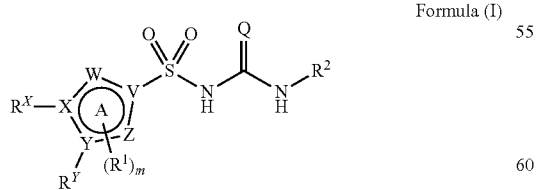

Formula (I)

or a pharmaceutically acceptable salt or solvate thereof, wherein:
Q is selected from O or S;
V, X and Y are each independently selected from C and N, and W and Z are each independently selected from N, O, S, NH and CH, provided that at least one of V, W, X, Y and Z is N, O, S or NH;
R$^X$ and R$^Y$ are each independently a halo, —OH, —NO$_2$, —NH$_2$, —N$_3$, —SH, —SO$_2$H, —SO$_2$NH, or a saturated or unsaturated hydrocarbyl group, wherein the hydrocarbyl group may be straight-chained or branched, or be or include cyclic groups, wherein the hydrocarbyl group may optionally be substituted, and wherein the hydrocarbyl group may optionally include one or more heteroatoms N, O or S in its carbon skeleton;
optionally R$^X$ and R$^Y$ together with the atoms X and Y to which they are attached may form a 4- to 12-membered saturated or unsaturated cyclic group fused to ring A, wherein the cyclic group fused to ring A may optionally be substituted;
m is 0, 1 or 2;
each R$^1$ is independently a halo, —OH, —NO$_2$, —NH$_2$, —N$_3$, —SH, —SO$_2$H, —SO$_2$NH, or a saturated or unsaturated hydrocarbyl group, wherein the hydrocarbyl group may be straight-chained or branched, or be or include cyclic groups, wherein the hydrocarbyl group may optionally be substituted, and wherein the hydrocarbyl group may optionally include one or more heteroatoms N, O or S in its carbon skeleton;
optionally R$^X$ and any R$^1$ attached to W may together with the atoms W and X to which they are attached form a 4- to 12-membered saturated or unsaturated cyclic group fused to ring A, wherein the cyclic group fused to ring A may optionally be substituted;
optionally R$^Y$ and any R$^1$ attached to Z may together with the atoms Y and Z to which they are attached form a 4- to 12-membered saturated or unsaturated cyclic group fused to ring A, wherein the cyclic group fused to ring A may optionally be substituted; and $R^2$ is selected from:

(i) a group having the formula:

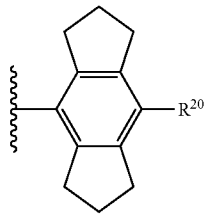

wherein $R^{20}$ is a halo, —OH, —NO$_2$, —NH$_2$, —N$_3$, —SH, —SO$_2$H, —SO$_2$NH, or a saturated or unsaturated hydrocarbyl group, wherein the hydrocarbyl group may be straight-chained or branched, or be or include cyclic groups, wherein the hydrocarbyl group may optionally be substituted, and wherein the hydrocarbyl group may optionally include one or more heteroatoms N, O or S in its carbon skeleton; or (ii) a heteroaryl group substituted at the α and α' positions, wherein $R^2$ may optionally be further substituted.

2. The compound or pharmaceutically acceptable salt or solvate thereof, as claimed in claim 1, wherein ring A is monocyclic.

3. The compound or pharmaceutically acceptable salt or solvate thereof, as claimed in claim 1, wherein at least one of W and Z is O or S.

4. The compound or pharmaceutically acceptable salt or solvate thereof, as claimed in claim 1, wherein any monovalent $R^X$ or $R^Y$ contains from 1 to 8 atoms other than hydrogen.

5. The compound or pharmaceutically acceptable salt- or solvate thereof, as claimed in claim 1, wherein $R^X$ and $R^Y$ are each independently a halo group or a saturated hydrocarbyl group, wherein the saturated hydrocarbyl group may be straight-chained or branched, or be or include cyclic groups, wherein the saturated hydrocarbyl group may optionally be substituted with one or more groups independently selected from halo, —CN, —OH, —NH$_2$ and oxo (=O), and wherein the saturated hydrocarbyl group may optionally include one or two heteroatoms independently selected from N and O in its carbon skeleton.

6. The compound or pharmaceutically acceptable salt or solvate thereof, as claimed in claim 1, wherein each $R^1$ is independently selected from halo; —CN; —NO$_2$; —N$_3$; —R$^β$; —OH; —OR$^β$; —R$^α$-halo; —R$^α$—CN; —R$^α$—NO$_2$; —R$^α$—N$_3$; —R$^α$—R$^β$; —R$^α$—OH; —R$^α$—OR$^β$; —SH; —SR$^β$; —SOR$^β$; —SO$_2$H; —SO$_2$R$^β$; —SO$_2$NH$_2$; —SO$_2$NHR$^β$; —SO$_2$N(R$^β$)$_2$; —R$^α$—SH; —R$^α$—SR$^β$; —R$^α$—SOR$^β$; —R$^α$—SO$_2$H; —R$^α$—SO$_2$R$^β$; —R$^α$—SO$_2$NH$_2$; —R$^α$—SO$_2$NHR$^β$; —R$^α$—SO$_2$N(R$^β$)$_2$; —NH$_2$; —NHR$^β$; —N(R$^β$)$_2$; —R$^α$—NH$_2$; —R$^α$—NHR$^β$; —R$^α$-N(R$^β$)$_2$; —CHO; —COR$^β$; —COOH; —COOR$^β$; —OCOR$^β$; —R$^α$-CHO; —R$^α$—COR$^β$; —R$^α$—COOH; —R$^α$—COOR$^β$; or —R$^α$—OCOR$^β$;

wherein each —R$^α$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —R$^3$ groups; and wherein each —R$^β$ is independently selected from a C$_1$-C$_6$ alkyl, C$_2$-C$_6$ alkenyl, C$_2$-C$_6$ alkynyl or C$_2$-C$_6$ cyclic group, and wherein any —R$^β$ may optionally be substituted with one or more C$_1$-C$_4$ alkyl, C$_1$-C$_4$ haloalkyl, C$_3$-C$_7$ cycloalkyl, —O(C$_1$-C$_4$ alkyl), —O(C$_1$-C$_4$ haloalkyl), —O(C$_3$-C$_7$ cycloalkyl), halo, —OH, —NH$_2$, —CN, —C≡CH, oxo (=O), or 4- to 6-membered heterocyclic group.

7. The compound or pharmaceutically acceptable salt or solvate thereof, as claimed in claim 1, wherein $R^2$ has the formula:

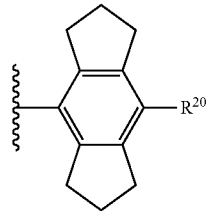

wherein $R^{20}$ is as defined in claim 1.

8. The compound or pharmaceutically acceptable salt or solvate thereof, as claimed in claim 7, wherein $R^{20}$ is a fluoro, chloro, bromo or —CN group.

9. The compound or pharmaceutically acceptable salt or solvate thereof, as claimed in claim 1, wherein $R^2$ is a heteroaryl group substituted at the α and α' positions, wherein $R^2$ may optionally be further substituted.

10. The compound or pharmaceutically acceptable salt or solvate thereof, as claimed in claim 9, wherein $R^2$ has a formula selected from:

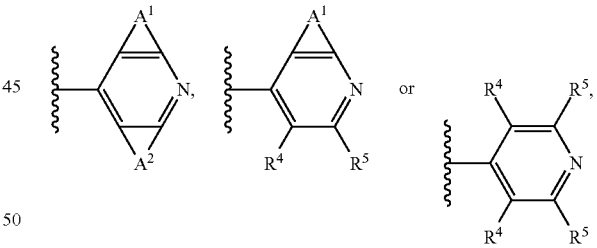

wherein:

$A^1$ and $A^2$ are each independently selected from a straight chain alkylene group, wherein one or two carbon atoms in the backbone of the alkylene group may optionally be replaced by one or two heteroatoms independently selected from nitrogen and oxygen, wherein the alkylene group may optionally be substituted with one or more halo,-OH, —CN, —O(C$_1$-C$_4$ alkyl) or —O(C$_1$-C$_4$ haloalkyl) groups, and wherein any ring containing $A^1$ or $A^2$ is a 5- or 6-membered ring;

each $R^4$ is independently selected from a C$_1$-C$_6$ alkyl or C$_3$-C$_6$ cycloalkyl group, wherein the C$_1$-C$_6$ alkyl or C$_3$-C$_6$ cycloalkyl group may optionally be substituted with one or more halo, —OH, —CN, —O(C$_1$-C$_4$ alkyl) or —O(C$_1$-C$_4$ haloalkyl) groups; and each $R^5$ is independently selected from hydrogen or a halo group.

11. The compound or pharmaceutically acceptable salt or solvate thereof, as claimed in claim 9, wherein $R^2$ has the formula:

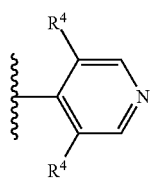

wherein each $R^4$ is independently selected from a $C_1$-$C_4$ alkyl group.

12. The compound or pharmaceutically acceptable salt or solvate thereof, as claimed in claim 1, wherein Q is O.

13. The compound or pharmaceutically acceptable salt or solvate thereof, as claimed in claim 1, which is (a) a compound selected from the group consisting of:

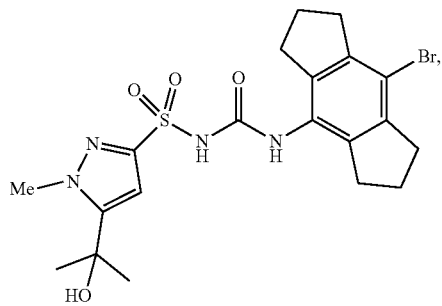

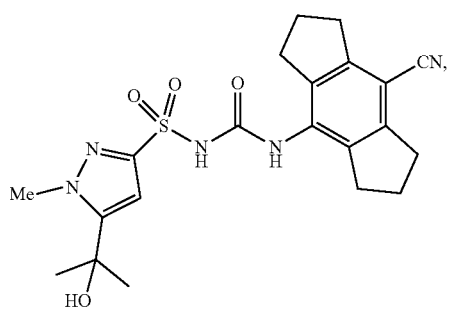

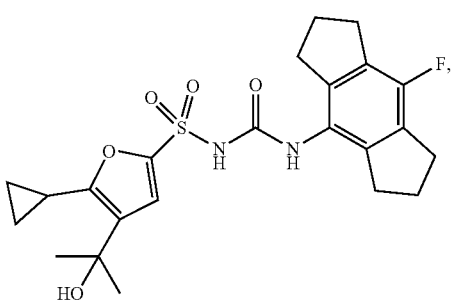

-continued

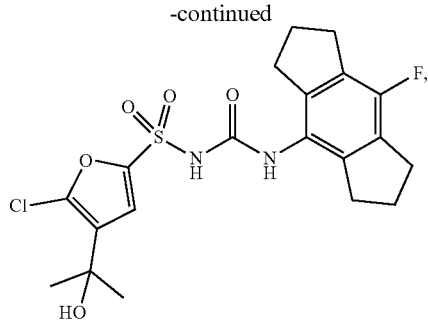

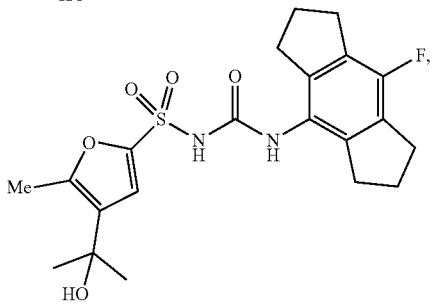

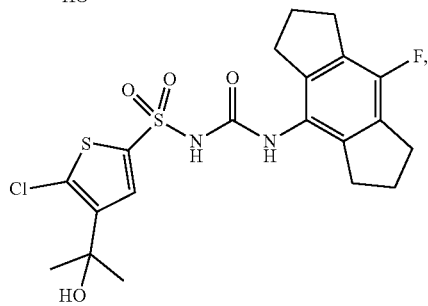

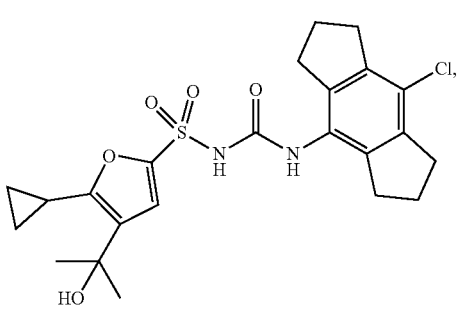

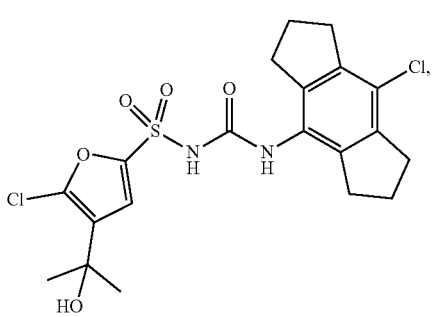

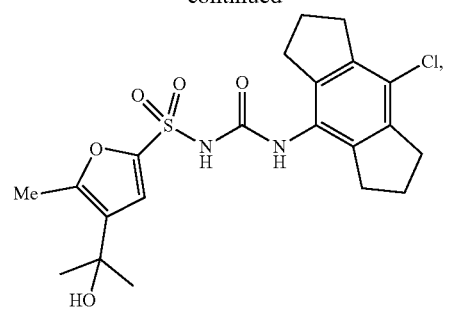
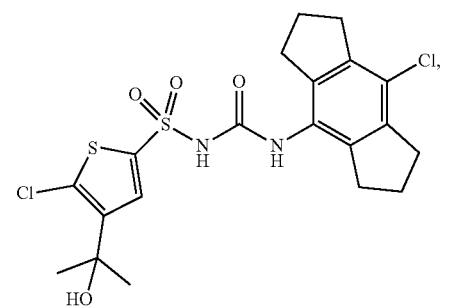
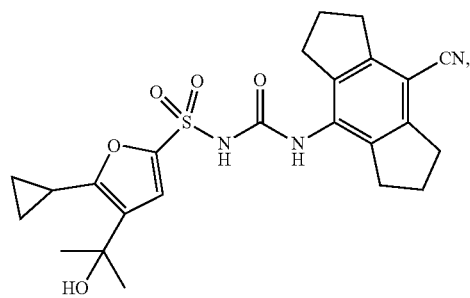
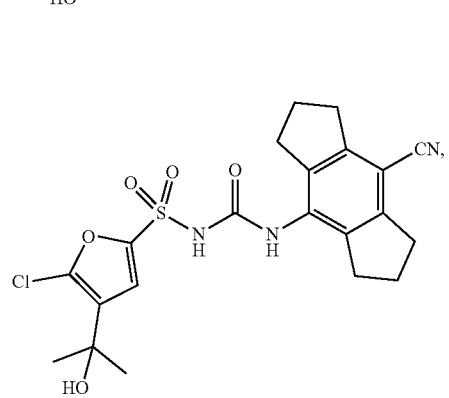
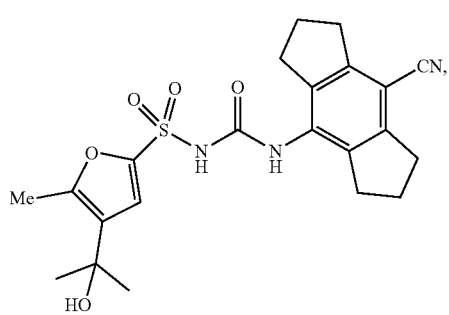
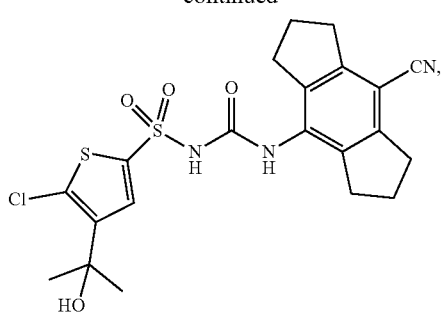
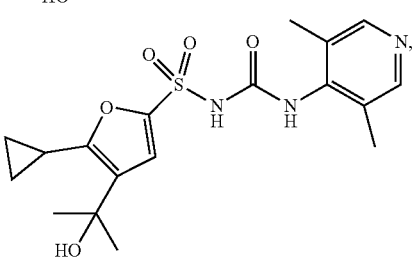
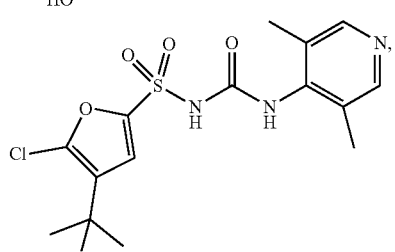
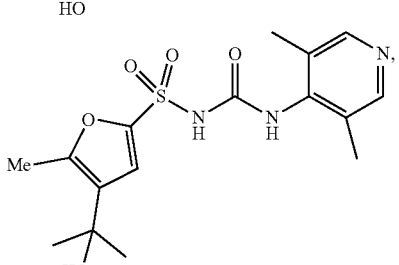
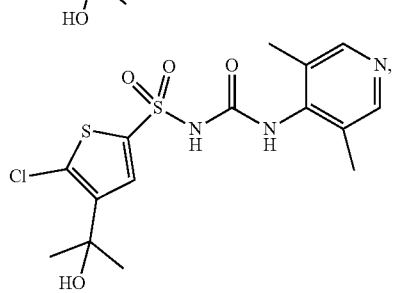
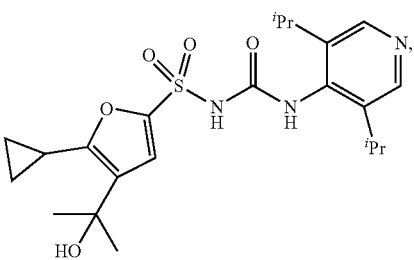

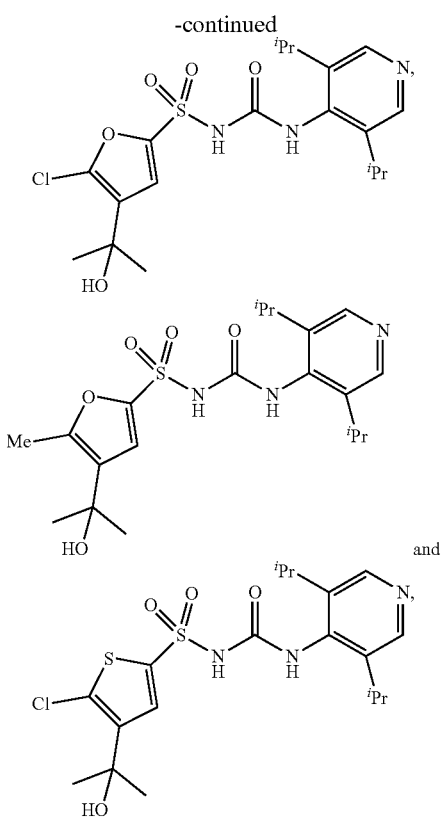

or (b) a pharmaceutically acceptable salt or solvate of the selected compound.

14. A pharmaceutical composition comprising the compound or the pharmaceutically acceptable salt or solvate thereof, as claimed in claim 1, and a pharmaceutically acceptable excipient.

15. A method of treating by ameliorative or palliative therapy, or of delaying onset or reducing risk of a disease, disorder or condition in a subject, the method comprising the step of administering an effective amount of the compound or the pharmaceutically acceptable salt or solvate thereof, as claimed in claim 1, to the subject, thereby treating by ameliorative or palliative therapy, or delaying onset or reducing risk of the disease, disorder or condition, wherein the disease, disorder or condition is responsive to NLRP3 inhibition.

16. The method as claimed in claim 15, wherein the disease, disorder or condition is selected from:
 (i) inflammation;
 (ii) an auto-immune disease;
 (iii) cancer;
 (iv) an infection;
 (v) a central nervous system disease;
 (vi) a metabolic disease;
 (vii) a cardiovascular disease;
 (viii) a respiratory disease;
 (ix) a liver disease;
 (x) a renal disease;
 (xi) an ocular disease;
 (xii) a skin disease;
 (xiii) a lymphatic condition;
 (xiv) a psychological disorder;
 (xv) graft versus host disease;
 (xvi) allodynia; and
 (xvii) any disease where an individual has been determined to carry a germline or somatic non-silent mutation in NLRP3.

17. The method as claimed in claim 15, wherein the disease, disorder or condition is selected from:
 (i) cryopyrin-associated periodic syndromes (CAPS);
 (ii) Muckle-Wells syndrome (MWS);
 (iii) familial cold autoinflammatory syndrome (FCAS);
 (iv) neonatal onset multisystem inflammatory disease (NOMID);
 (v) familial Mediterranean fever (FMF);
 (vi) pyogenic arthritis, pyoderma gangrenosum and acne syndrome (PAPA);
 (vii) hyperimmunoglobulinemia D and periodic fever syndrome (HIDS);
 (viii) Tumour Necrosis Factor (TNF) Receptor-Associated Periodic Syndrome (TRAPS);
 (ix) systemic juvenile idiopathic arthritis;
 (x) adult-onset Still's disease (AOSD);
 (xi) relapsing polychondritis;
 (xii) Schnitzler's syndrome;
 (xiii) Sweet's syndrome;
 (xiv) Behcet's disease;
 (xv) anti-synthetase syndrome;
 (xvi) deficiency of interleukin 1 receptor antagonist (DIRA); and
 (xvii) haploinsufficiency of A20 (HA2o).

18. A method of inhibiting NLRP3 in a subject, the method comprising administering the compound or the pharmaceutically acceptable salt or solvate thereof, as claimed in claim 1, to the subject thereby inhibiting NLRP3.

19. A method of analysing inhibition of NLRP3 or an effect of inhibition of NLRP3 by a compound, comprising contacting a cell or non-human animal with the compound or the pharmaceutically acceptable salt or solvate thereof, as claimed in claim 1, and analysing inhibition of NLRP3 or an effect of inhibition of NLRP3 in the cell or non-human animal by the compound.

20. The method as claimed in claim 15, wherein the compound or the pharmaceutically acceptable salt or solvate thereof is administered as a pharmaceutical composition further comprising a pharmaceutically acceptable excipient.

21. A prodrug of the compound as claimed in claim 1, or a pharmaceutically acceptable salt or solvate thereof.

22. A method of treating by ameliorative or palliative therapy, or of delaying onset or reducing risk of a disease, disorder or condition in a subject, the method comprising the step of administering an effective amount of the prodrug or the pharmaceutically acceptable salt or solvate thereof, as claimed in claim 21, to the subject, thereby treating by ameliorative or palliative therapy, or delaying onset or reducing risk of the disease, disorder or condition, wherein the disease, disorder or condition is responsive to NLRP3 inhibition.

* * * * *